United States Patent
Cosa et al.

(10) Patent No.: US 9,969,755 B2
(45) Date of Patent: May 15, 2018

(54) PHOTODYNAMIC THERAPY PHOTOSENSITIZERS

(71) Applicant: The Royal Institution for the Advancement of Learning/McGill University, Montreal (CA)

(72) Inventors: Gonzalo Cosa, Montreal (CA); Andres M. Durantini, Montreal (CA); Lana E. Greene, Montreal (CA); Richard Lincoln, Montreal (CA)

(73) Assignee: THE ROYAL INSTITUTION FOR THE ADVANCEMENT OF LEARNING/MCGILL UNIVERSITY, Montreal (CA)

( * ) Notice: Subject to any disclaimer, the term of this patent is extended or adjusted under 35 U.S.C. 154(b) by 0 days. days.

(21) Appl. No.: 15/404,763

(22) Filed: Jan. 12, 2017

(65) Prior Publication Data
US 2017/0197993 A1    Jul. 13, 2017

Related U.S. Application Data

(60) Provisional application No. 62/277,556, filed on Jan. 12, 2016.

(51) Int. Cl.
| | |
|---|---|
| *C07F 5/02* | (2006.01) |
| *A61K 41/00* | (2006.01) |
| *A61N 5/06* | (2006.01) |
| *A61N 5/067* | (2006.01) |

(52) U.S. Cl.
CPC .......... C07F 5/022 (2013.01); A61K 41/0019 (2013.01); A61K 41/0057 (2013.01); A61N 5/062 (2013.01); *A61N 2005/067* (2013.01)

(58) Field of Classification Search
CPC ....................................................... C07F 5/022
See application file for complete search history.

(56) References Cited

PUBLICATIONS

Cancer and Metastasis Reviews (1998), 17(1), 91-106.*
Science (1999), vol. 286, 531-537.*
Cancer [online], [retrieved on Jul. 6, 2007]. Retrieved from the internet, URL http://www.nlm.nih.gov/medlineplus/cancer.html>.*
Montalban, A. G.; Meunier, H. G.; Ostler, R. B.; Barrett, A. G. M.; Hoffman, B. M.; Rumbles, G., J. Phys. Chem. A 1999, 103, 4352.
Mukai, K.; Daifuku, K.; Okabe, K.; Tanigaki, T.; Inoue, K., J. Org. Chem. 1991, 56, 4188.
Nepomnyashchii, A. B.; Broring, M.; Ahrens, J.; Bard, A. J., Synthesis, Photophysical, Electrochemical, and Electrogenerated Chemiluminescence Studies. Multiple Sequential Electron Transfers in BODIPY Monomers, Dimers, Trimers, and Polymer, J. Am. Chem. Soc. 2011, 133, 8633.
Nepomnyashchii, A. B.; Bard, A. J., Electrochemistry and Electrogenerated Chemiluminescence of BODIPY Dyes, Acc. Chem. Res. 2012, 45, 1844.
Niethammer, P.; Grabher, C.; Look, A. T.; Mitchison, T. J., Nature 2009, 459, 996.
Niki, E.; Noguchi, N., Acc. Chem. Res. 2004, 37, 45.
Ogilby, P. R., Chem. Soc. Rev. 2010, 39, 3181.
Oleynik, P. R.; Ishihara, Y.; Cosa, G., J. Am. Chem. Soc. 2007, 129, 1842.
Porter, N. A., Acc. Chem. Res. 1986, 19, 262.
Rapozzi, V.; Miculan, M.; Xodo, L. E., Cancer Biol. Ther. 2009, 8, 1318.
Rehm, D.; Weller, A. Isr. J. Chem. 1970, 8, 259.
Schumacker, P. T., Reactive oxygen species in cancer cells: Live by the sword, die by the sword, Cancer Cell 2006, 10, 175.
Schumacker, P. T., Reactive Oxygen Species in Cancer: A Dance with the Devil, Cancer Cell 2015, 27, 156.
Schweitzer, C.; Schmidt, R., Chem. Rev. 2003, 103, 1685.
Shahidi, F.; Zhong, Y., Chem. Soc. Rev. 2010, 39, 4067.
Szatrowski, T. P.; Nathan, C. F., Cancer Res. 1991, 51, 794.
Thapaliya, E R.; Swaminathan, S.; Captain, B.; Raymo, F. M., J. Am. Chem. Soc. 2014, 136, 13798.
Trachootham, D.; Zhou, Y.; Zhang, H.; Demizu, Y.; Chen, Z.; Pelicano, H.; Chiao, P. J.; Achanta, G.; Arlinghaus, R. B.; Liu, J.; Huang, P., Cancer Cell 2006, 10, 241.
Turro, N. J.; Ramamurthy, V.; Scaiano, J. C., Modern Molecular Photochemistry of Organic Molecules; University Science Books, 2012.
Ulrich, G.; Ziessel, R.; Harriman, A., Angew. Chem. Int. Ed. Engl. 2008, 47, 1184.
Wilkinson, F.; Helman, W. P.; Ross, A. B., J. Phys. Chem. Ref. Data 1993, 22, 113.
Wood, T. E.; Thompson, A., Chem. Rev. 2007, 107, 1831.
Wu, W.; Guo, H.; Wu, W.; Ji, S.; Zhao, J., J. Org. Chem. 2011, 76, 7056.

(Continued)

*Primary Examiner* — Shawquia Jackson
(74) *Attorney, Agent, or Firm* — Isabelle Pelletier

(57) ABSTRACT

A compound of formula (I) useful as a photosensitizer in photodynamic therapy is provided. There is also provided a photosensitizing composition for use in photodynamic therapy comprising this compound. Finally, there are provided a method of killing cells under oxidative stress conditions and a method for the selective delivery of singlet oxygen ($^1O_2$) to cells having an increased reactive oxygen species (ROS) concentration, these methods comprising the steps of contacting such cells with a compound of formula (I), and exposing the cells to light.

(I)

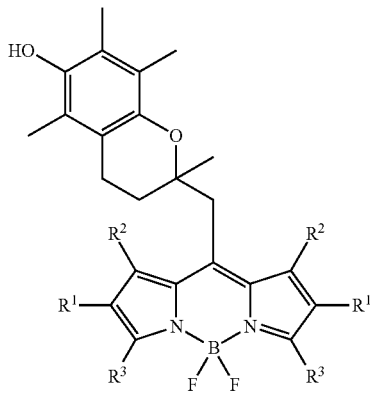

14 Claims, 30 Drawing Sheets

(56) References Cited

PUBLICATIONS

Yin, H.; Xu, L.; Porter, N. A., Chem. Rev. 2011, 111, 5944.
Yogo, T.; Urano, Y.; Ishitsuka, Y.; Maniwa, F.; Nagano, T., Highly Efficient and Photostable Photosensitizer Based on BODIPY Chromophore, J. Am. Chem. Soc. 2005, 127, 12162.
Yogo, T.; Urano, Y.; Mizushima, A.; Sunahara, H.; Inoue, T.; Hirose, K.; Iino, M.; Kikuchi, K.; Nagano, T., Selective photoinactivation of protein function through environment-sensitive switching of singlet oxygen generation by photosensitizer, Proc. Natl. Acad. Sci. U. S. A. 2008, 105, 28.
Zhang, X. F.; Yang, X., J. Phys. Chem. B 2013, 117, 5533.
Zheng, G.; Chen, J.; Stefflova, K.; Jarvi, M.; Li, H.; Wilson, B. C., Proc. Natl. Acad. Sci. U. S. A. 2007, 104, 8989.
Adarsh, N.; Avirah, R. R.; Ramaiah, D. Org. Lett. 2010, 12, 5720.
Agostinis, P.; Berg, K.; Cengel, K. A.; Foster, T. H.; Girotti, A. W.; Gollnick, S. O.; Hahn, S. M.; Hamblin, M. R.; Juzeniene, A.; Kessel, D.; Korbelik, M.; Moan, J.; Mroz, P.; Nowis, D.; Piette, J.; Wilson, B. C.; Golab, J., C.A. Cancer J. Clin. 2011, 61, 250.
Auf Dem Keller, U.; Kumin, A.; Braun, S.; Werner, S., J. Investig. Dermatol. Symp. Proc. 2006, 11, 106.
Bartusik, D.; Minnis, M.; Ghosh, G.; Greer, A., J. Org. Chem. 2013, 78, 8537.
Bonnett, R., Photosensitizers of the Porphyrin and Phthalocyanine Series for Photodynamic Therapy, Chem. Soc. Rev. 1995, 24, 19.
Bonnett, R., Chemical aspects of photodynamic therapy; CRC Press, 2000.
Bressler, N. M.; Bressler, S. B. Invest. Ophthalmol. Vis. Sci. 2000, 41, 624.
Bryan, N.; Ahswin, H.; Smart, N.; Bayon, Y.; Wohlert, S.; Hunt, J. A., Eur. Cell. Mater. 2012, 24, 249.
Burton, G. W.; Ingold, K. U., Acc. Chem. Res. 1986, 19, 194.
Chen, J.; Stefflova, K.; Niedre, M. J.; Wilson, B. C.; Chance, B.; Glickson, J. D.; Zheng, G., J. Am. Chem. Soc. 2004, 126, 11450.
Cosa, G.; Scaiano, J. C., Photochem. Photobiol. 2004, 80, 159.
Dolmans, D. E.; Fukumura, D.; Jain, R. K., Nat. Rev. Cancer 2003, 3, 380.
Dwyer, D. J.; Belenky, P. A.; Yang, J. H.; MacDonald, I. C.; Martell, J. D.; Takahashi, N.; Chan, C. T. Y.; Lobritz, M. A.; Braff, D.; Schwarz, E. G.; Ye, J. D.; Pati, M.; Vercruysse, M.; Ralifo, P. S.; Allison, K. R.; Khalil, A. S.; Ting, A. Y.; Walker, G. C.; Collins, J. J., Proc. Natl. Acad. Sc. U. S. A. 2014, 111, E2100.
Fahrenholtz, S. R.; Doleiden, F. H.; Trozzolo, A. M.; Lamola, A. A., Photochem. Photobiol. 1974, 20, 505.
Foote, C. S., Photosensitized Oxygenations and the Role of Singlet Oxygen, Acc. Chem. Res. 1968, 1, 104.
Foote, C. S.; Ching, T.-Y.; Geller, G. G., Chemistry of Singlet Oxygen—XVIII. Rates of Reaction and Quenching of (Y-Tocopherol and Singlet Oxygen, Photochem. Photobiol. 1974, 20, 511.
Fragata, M.; Bellemare, F., Chem. Phys. Lipids 1980, 27, 93.
Franco, C.; Olmsted III, J., Talanta 1990, 37, 905.
Fukuzawa, K.; Matsuura, K.; Tokumura, A.; Suzuki, A.; Terao, J., Kinetics and dynamics of singlet oxygen scavenging by α-tocopherol in phospholipid model membranes, Free Radic. Biol. Med. 1997, 22, 923.
Fukuzawa, K.; Inokami, Y.; Tokumura, A.; Terao, J.; Suzuki, A., Rate Constants for Quenching Singlet Oxygen and Activities for Inhibiting Lipid Peroxidation of Carotenoids and α-Tocopherol in Liposomes Lipids 1998, 33, 751.
Galletta, M.; Campagna, S.; Quesada, M.; Ulrich, G.; Ziessel, R., Chem. Commun. (Camb.) 2005, 4222.
Girotti, A. W., J. Lipid Res. 1998, 39, 1529.
Godin, R.; Liu, H. W.; Smith, L.; Cosa, G., Langmuir 2014, 30, 11138.
Gomes, A.; Fernandes, E.; Lima, J. L. J., Biochem. Biophys. Methods 2005, 65, 45.
Gorman, A. A.; Gould, I. R.; Hamblett, I.; Standen, M. C., J. Am. Chem. Soc. 1984, 106, 6956.
Gorrini, C.; Harris, I. S.; Mak, T. W., Nat. Rev. Drug Discov. 2013, 12, 931.
Guo, S.; Ma, L. H.; Zhao, J. Z.; Kucukoz, B.; Karatay, A.; Hayvali, M.; Yaglioglu, H. G.; Elmali, A., Chem. Sci. 2014, 5, 489.
Gustafson, T. P.; Metzel, G. A.; Kutateladze, A. G., Photochem. Photobiol. Sci. 2012, 11, 564.
Hamblin, M. R.; Hasan, T., Photochem. Photobiol. Sci. 2004, 3, 436.
Horrobin, D. F., New Approaches to Cancer Treatment: Unsaturated Lipids and Photodynamic Therapy; Churchill Communications Europe, 1994.
Huang, L.; Yang, W.; Zhao, J., J. Org. Chem. 2014, 79, 10240.
Imlay, J. A.; Chin, S. M.; Linn, S., Science 1988, 240, 640.
Jiao, L.; Pang, W.; Zhou, J.; Wei, Y.; Mu, X.; Bai, G.; Hao, E., J. Org. Chem. 2011, 76, 9988.
Johnson, I. D.; Kang, H. C.; Haugland, R. P., Anal. Biochem. 1991, 198, 228.
Kamkaew, A.; Lim, S. H.; Lee, H. B.; Kiew, L V.; Chung, L. Y.; Burgess, K., Chem. Soc. Rev. 2013, 42, 77.
Kasha, M., J. Chem. Phys. 1952, 20, 71.
Khatchadourian, A.; Krumova, K.; Boridy, S.; Ngo, A. T.; Maysinger, D.; Cosa, G., Biochemistry 2009, 48, 5658.
Krumova, K.; Oleynik, P.; Karam, P.; Cosa, G., Phenol-Based Lipophilic Fluorescent Antioxidant Indicators: A Rational Approach, J. Org. Chem. 2009, 74, 3641.
Krumova, K.; Cosa, G., Bodipy Dyes with Tunable Redox Potentials and Functional Groups for Further Tethering: Preparation, Electrochemical, and Spectroscopic Characterization, J. Am. Chem. Soc. 2010, 132, 17560.
Krumova, K.; Friedland, S.; Cosa, G., How Lipid Unsaturation, Peroxyl Radical Partitioning, and Chromanol Lipophilic Tail Affect the Antioxidant Activity of α-Tocopherol: Direct Visualization via High-Throughput Fluorescence Studies Conducted with Fluorogenic α-Tocopherol Analogues, J. Am. Chem. Soc. 2012, 134, 10102.
Krumova, K.; Cosa, G., Fluorogenic probes for imaging reactive oxygen species, Photochemistry: vol. 41 2013, 41, 279.
Krumova, K.; Greene, L. E.; Cosa, G., Fluorogenic α-Tocopherol Analogue for Monitoring the Antioxidant Status within the Inner Mitochondrial Membrane of Live Cells, J. Am. Chem. Soc. 2013, 135, 17135.
Lai, Y. C.; Chang, C. C., J. Mater. Chem. C 2014, 2, 1576.
Lincoln, R.; Greene, L. E.; Krumova, K.; Ding, Z.; Cosa, G., J. Phys. Chem. A 2014, 118, 10622.
López Arbeloa, F.; Banuelos, J.; Martinez, V.; Arbeloa, T.; López Arbeloa, I., Int. Rev. Phys. Chem. 2005, 24, 339.
Lou, P. J.; Jones, L.; Hopper, C., Technol. Cancer Res. Treat. 2003, 2, 311.
Loudet, A.; Burgess, K., Chem. Rev. 2007, 107, 4891.
Lovell, J. F.; Liu, T. W.; Chen, J.; Zheng, G., Chem. Rev. 2010, 110, 2839.
Lu, Z. T.; Zhang, X. G.; Wu, Z. M.; Zhai, T. T.; Xue, Y. A.; Mei, L.; Li, C. X., RSC Adv. 2014, 4, 19495.
Ma, J.; Yuan, X. L.; Kucukoz, B.; Li, S. F.; Zhang, C. S.; Majumdar, P.; Karatay, A.; Li, X. H.; Yaglioglu, H. G.; Elmali, A.; Zhao, J. Z.; Hayvali, M., J. Mater. Chem. C 2014, 2, 3900.

* cited by examiner (A)

(B)

(C)

(D)

(E)

(F)

PHOTODYNAMIC THERAPY PHOTOSENSITIZERS

CROSS REFERENCE TO RELATED APPLICATIONS

This application claims benefit, under 35 U.S.C. § 119(e), of U.S. provisional application Ser. No. 62/277,556, filed on Jan. 12, 2016. All documents above are incorporated herein in their entirety by reference.

FIELD OF THE INVENTION

The present invention relates to photodynamic therapy photosensitizers. More specifically, the present invention is concerned with such photosensitizers comprising a halogen-substituted boron-dipyrromethene (BODIPY) dye photosensitizer segment linked to the chromanol ring of α-tocopherol as a trap segment.

BACKGROUND OF THE INVENTION

Photodynamic therapy (PDT) is a methodology used for the treatment of cancer and other ailments. Also sometimes called photochemotherapy, it is a form of phototherapy using nontoxic light-sensitive compounds (photosensitizers) that are exposed selectively to light, whereupon they become toxic to targeted malignant and other diseased cells (phototoxicity). PDT has proven ability to kill microbial cells, including bacteria, fungi and viruses. PDT is popularly used in treating acne. It is used clinically to treat a wide range of medical conditions, including wet age-related macular degeneration and malignant cancers, and is recognised as a treatment strategy which is both minimally invasive and minimally toxic.

Most modern PDT applications involve three key components: a photosensitizer, a light source and tissue oxygen. The combination of these three components leads to the chemical destruction of any tissues which have both selectively taken up the photosensitizer and have been locally exposed to light. The wavelength of the light source needs to be appropriate for exciting the photosensitizer. A number of photo-chemical and/or photo-physical processes are prone to take place when chromophore (i.e. photosensitizer) molecules are promoted to a higher electronic energy or excited state following absorption of the electromagnetic radiation (typically UV or visible light). Among those processes, the excited chromophores may i) transfer their excess energy to an "acceptor" molecule (typically weakly absorbing), e.g. an oxidant such as a peroxide, which in turn may undergo a chemical bond scission to form alkoxyl radicals. The sensitizer may also ii) react directly with other substrates via e.g. electron transfer, forming radical ions. When the above sensitization pathways occur in the presence of oxygen, the previous reactions give rise to Type I photosensitization. The sensitizer may further iii) directly interact with oxygen, either by energy transfer to form singlet oxygen ($^1O_2$), or by electron transfer to form superoxide radical anion ($O_2.^-$) or hydrogen peroxide ($H_2O_2$, a 2 electron process). In the latter case the reaction is referred to as a Type II photosensitization (see FIG. 1).

PDT thus requires for the interaction of light, an active photosensitizer and molecular oxygen. In type II involving formation of singlet oxygen, following excitation of the photosensitizer, rapid intersystem crossing (ISC) takes place from its singlet excited state to the triplet excited state. The triplet excited state next acts as an energy donor to ground state molecular oxygen ($^3O_2$) yielding $^1O_2$ generated in situ.

In order to minimize undesired side effects, including damage to healthy tissue during PDT treatment, photosensitization of $^1O_2$ must be controlled at different levels. Conventionally, in order to achieve the selective destruction of the target area using PDT while leaving normal tissues untouched, either the photosensitizer is applied locally to the target area, or photosensitive targets are locally excited with light. For instance, in the treatment of skin conditions, including acne, psoriasis, and also skin cancers, the photosensitizer can be applied topically and locally excited by a light source. In the local treatment of internal tissues and cancers, after photosensitizers have been administered intravenously, light can be delivered to the target area using endoscopes and fiber optic catheters. Thus, the specific targeting of the photosensitizer to ailing over healthy tissue and the precise delivery of the exciting light exclusively to the desired tissue constitute two levels of spatiotemporal control.

Most recently, the chemical activation of a photosensitizer specifically in the targeted tissue has emerged as an effective third level of control. This method exploits differences in the proteome or metabolome of an ailing tissue over the healthy tissue. An enzyme or a chemical agent prevailing in the targeted tissue may site-specifically activate an otherwise dormant chromophore into a potent photosensitizer. Activation/unmasking of the otherwise dormant photosensitizer will occur upon e.g. the enzymatic hydrolysis of the quencher segment.

Photosensitizers can also target many viral and microbial species, including HIV and MRSA. Using PDT, pathogens present in samples of blood and bone marrow can be decontaminated before the samples are used further for transfusions or transplants. PDT can also eradicate a wide variety of pathogens of the skin and of the oral cavities. Given the seriousness that drug resistant pathogens have now become, there is increasing research into PDT as a new antimicrobial therapy.

SUMMARY OF THE INVENTION

In accordance with the present invention, there is provided:

1. A compound of formula (I):

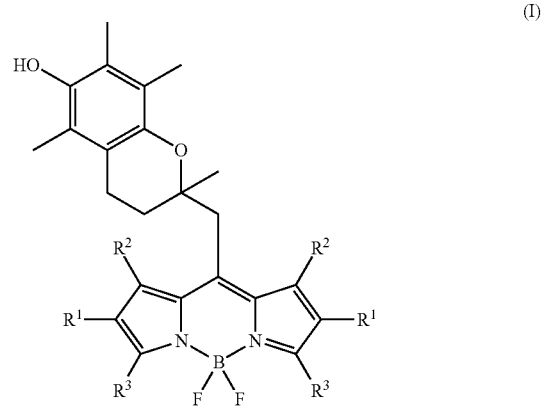

wherein:
R¹ are the same and represent —Br or —I,
R² are the same or different and represent —H or an alkyl group, and
R³ are the same or different and represent an alkyl group or a haloalkyl group.
2. The compound of item 1, wherein both R¹ groups are —Br.
3. The compound of item 1, wherein both R¹ groups are —I.
4. The compound of any one of items 1 to 3, wherein both R² groups are the same.
5. The compound of any one of items 1 to 4, wherein both $R_2$ group are an alkyl group, preferably methyl.
6. The compound of any one of items 1 to 4, wherein both R² groups are —H.
7. The compound of any one of items 1 to 3, wherein the R² groups are different from one another.
8. The compound of any one of items 1 to 7, wherein both R³ groups are the same.
9. The compound of any one of items 1 to 8, wherein both R³ group are an alkyl group, preferably methyl.
10. The compound of any one of items 1 to 7, wherein the R³ groups are different from one another.
11. The compound of item 1 being

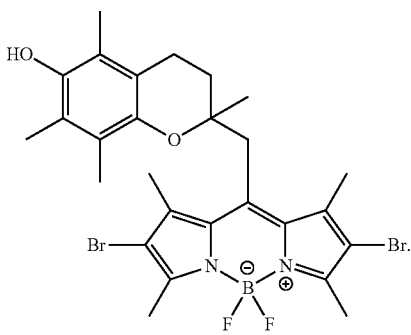 [SMILES: CC1=C(Br)C(C)=[N+]2C1=C(CC1(C)CCc3c(C)c(O)c(C)c(C)c3O1)c1c(C)c(Br)c(C)n1[B-]2(F)F]

12. The compound of any one of items 1 to 11 for use as a photosensitizer in photodynamic therapy.
13. Use of the compound of any one of items 1 to 11 as a photosensitizer in photodynamic therapy.
14. A photosensitizing composition for use in photodynamic therapy, the composition comprising the compound of any one of items 1 to 11, optionally together with biological acceptable carrier.
15. The photosensitizing composition of item 14 being for topical administration.
16. The photosensitizing composition of item 14 being for systemic administration.
17. The photosensitizing composition of item 14 or 15 being a cosmeceutical composition.
18. The photosensitizing composition of any one of items 14 to 16 being a pharmaceutical composition.
19. The compound, use or composition of any one of items 12 to 18, wherein the photodynamic therapy is for the treatment of a bacterial infection in a wound.
20. The compound, use or composition of any one of items 12 to 18, wherein the photodynamic therapy is for the treatment of skin conditions, such as psoriasis, vitiligo and acne.
21. The compound, use or composition of any one of items 12 to 18, wherein the photodynamic therapy is for the treatment of drug resistant bacteria.
22. The compound, use or composition of any one of items 12 to 18, wherein the photodynamic therapy is for the treatment of cancer.
23. A method for the selective delivery of singlet oxygen ($^1O_2$) to cells having an increased reactive oxygen species (ROS) concentration, the method comprising the steps of:
a) contacting said cells having an increased ROS concentration with a compound of any one of items 1 to 11, thereby allowing the reactive oxygen species to locally activate said compound, and
b) exposing the activated compound to light, thereby producing and selectively delivering singlet oxygen to the cells having an increased ROS concentration.
24. The method of item 23, wherein the delivery of singlet oxygen results in the inactivation or destruction of the cells having an increased ROS concentration.
25. The method of item 23 or 24, wherein in step a), the cells having an increased ROS concentration are present together with other cells that do not have an increased ROS concentration and the compound is also contacted with said other cells, the contact between the compound and said other cells resulting in the compound locally remaining dormant, step a) thus resulting in the selective local activation of the compound only in the cells having an increased ROS concentration.
26. The method of any one of items 23 to 25, wherein the step a) comprises the administration of the compound to a subject.
27. The method of item 26, wherein said administration is local.
28. The method of item 26, wherein said administration is topical.
29. The method of item 26, wherein said administration is systemic.
30. The method of any one of items 23 to 29, wherein said cells having an increased ROS concentration are cancer cells.
31. The method of any one of items 23 to 29, wherein said cells having an increased ROS concentration are infected cells.
32. The method of item 31, wherein said cells are infected by a bacterium, a virus, a parasite or a fungus.
33. The method of any one of items 23 to 29, wherein said cells having an increased ROS concentration are bacterial cells.
34. The method of item 33, wherein said bacterial cells are infecting a tissue in a subject.
35. The method of item 33 or 34, wherein said bacterial cells are drug resistant bacteria treated with a bactericidal treatment.
36. The method of any one of items 23 to 29, wherein said cells having an increased ROS concentration are skin cells affected by a skin condition.
37. The method of item 36, wherein said skin condition is vitiligo.
38. The method of item 36, wherein said skin condition is acne.
39. The method of item 36, wherein said skin condition is psoriasis.
40. A method for killing cells under oxidative stress conditions, the method comprising the steps of:
a) contacting said cells with a compound of any one of items 1 to 11, and
b) exposing the cells to light.
41. The method of item 40, wherein the step a) comprises the administration of the compound to a subject.

42. The method of item 41, wherein said administration is local.
43. The method of item 41, wherein said administration is topical.
44. The method of item 41, wherein said administration is systemic.
45. The method of any one of items 40 to 44, wherein said cells under oxidative stress conditions are cancer cells.
46. The method of any one of items 40 to 44, wherein said cells under oxidative stress conditions are infected cells.
47. The method of item 46, wherein said cells are infected by a bacterium, a virus, a parasite or a fungus.
48. The method of any one of items 40 to 44, wherein said cells under oxidative stress conditions are bacterial cells.
49. The method of item 48, wherein said bacterial cells are infecting a tissue in a subject.
50. The method of item 48 or 49, wherein said bacterial cells are drug resistant bacteria treated with a bactericidal treatment.
51. The method of any one of items 40 to 44, wherein said cells under oxidative stress conditions are skin cells affected by a skin condition.
52. The method of item 51, wherein said skin condition is vitiligo.
53. The method of item 51, wherein said skin condition is acne.
54. The method of item 51, wherein said skin condition is psoriasis.

DETAILED DESCRIPTION OF THE INVENTION

Figure 1:
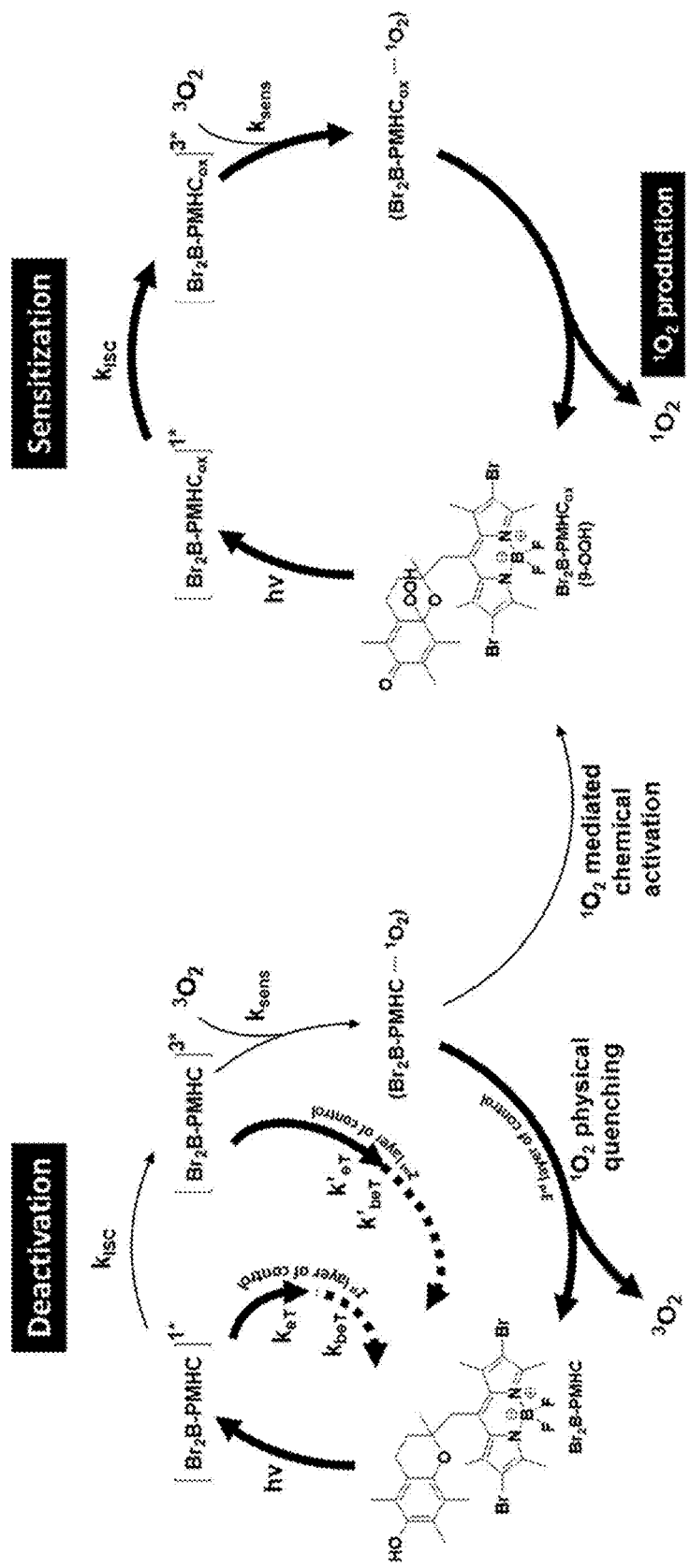
FIG. 1 shows the proposed mechanism for autocatalytic $^1O_2$ amplification.
Figure 2:
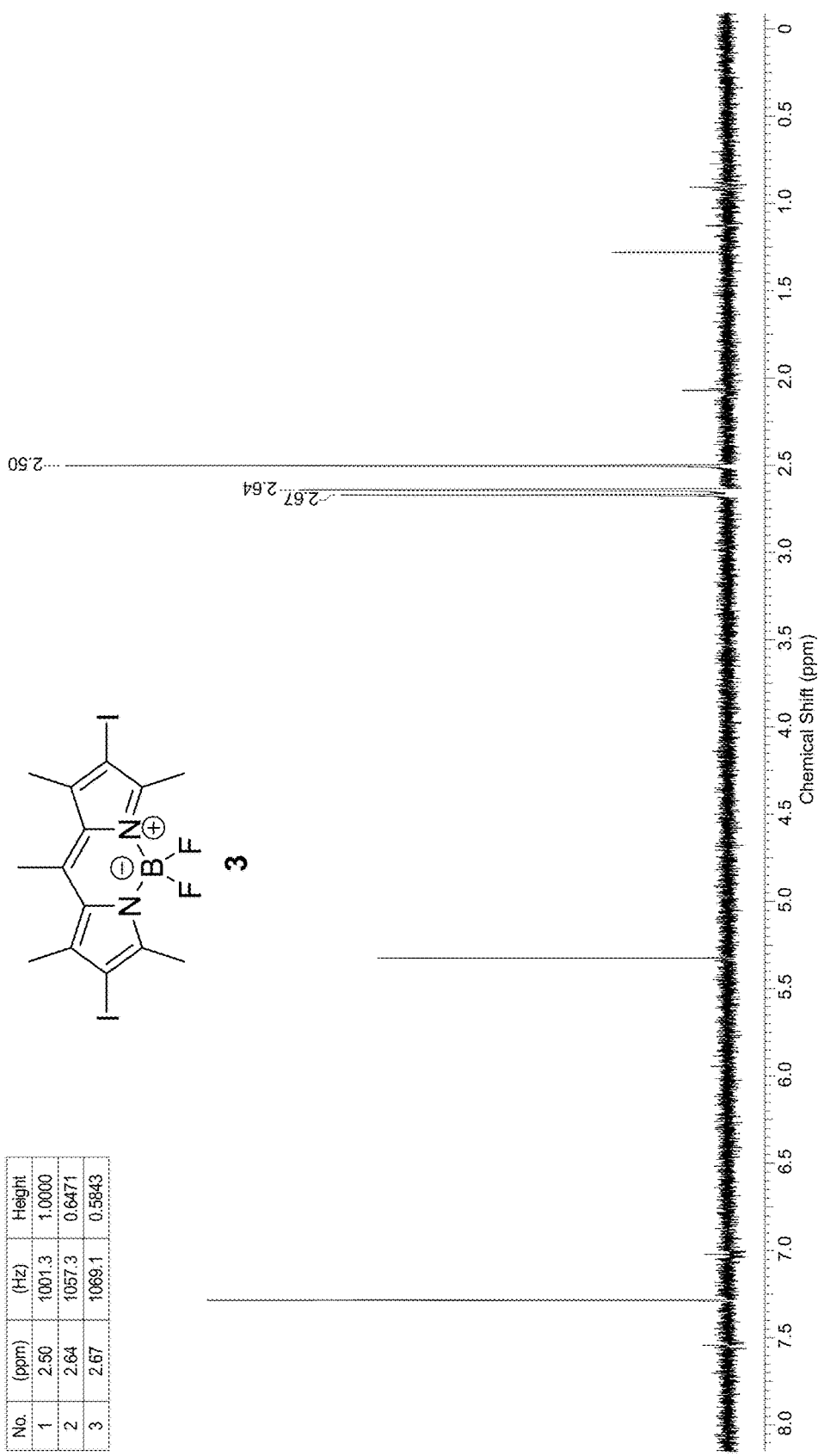
FIG. 2 shows the $^1H$ NMR spectrum of compound 3.
Figure 3:
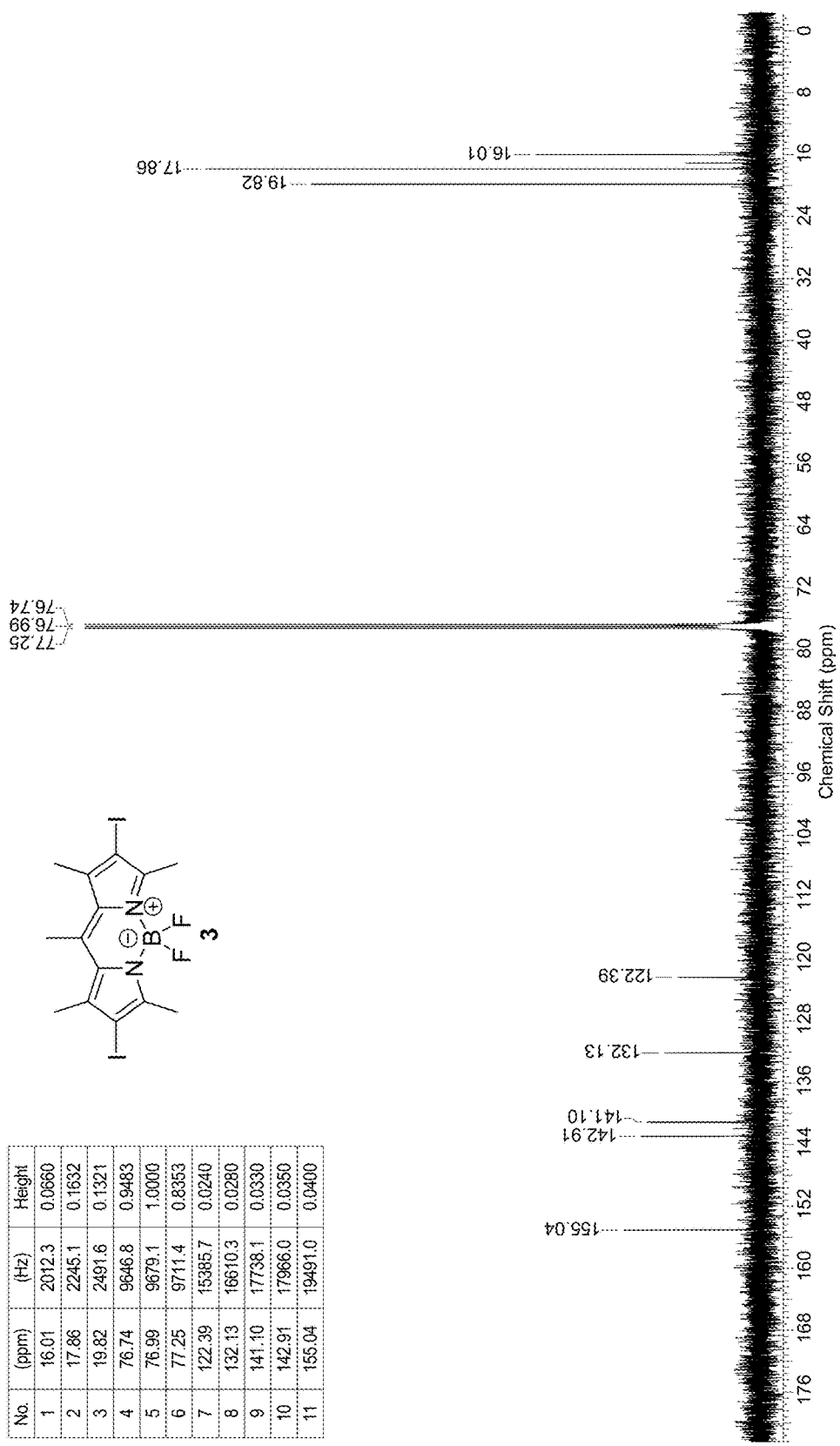
FIG. 3 shows the $^{13}C$ NMR spectrum of compound 3.
Figure 4:
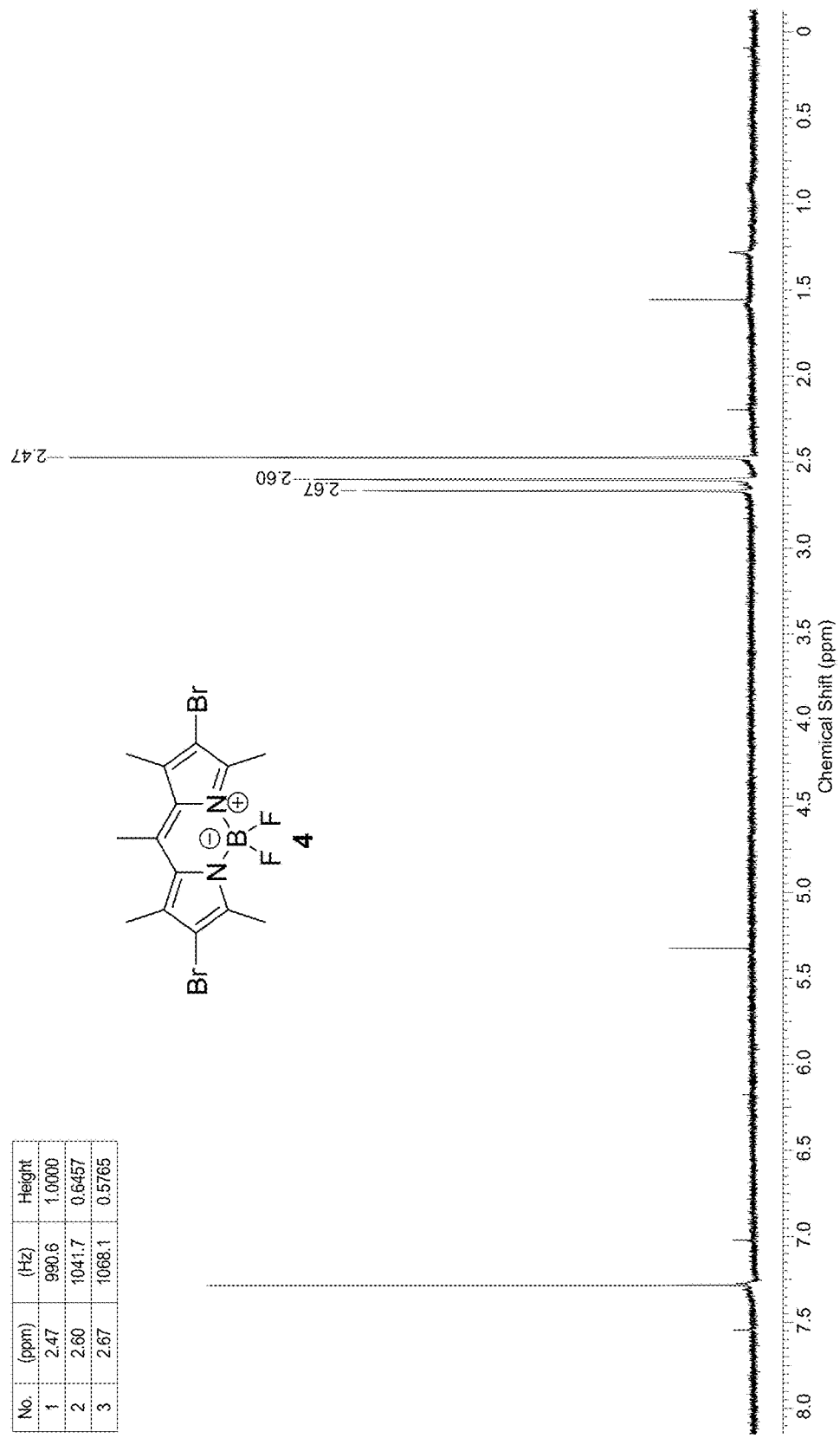
FIG. 4 shows the $^1H$ NMR spectrum of compound 4.
Figure 5:
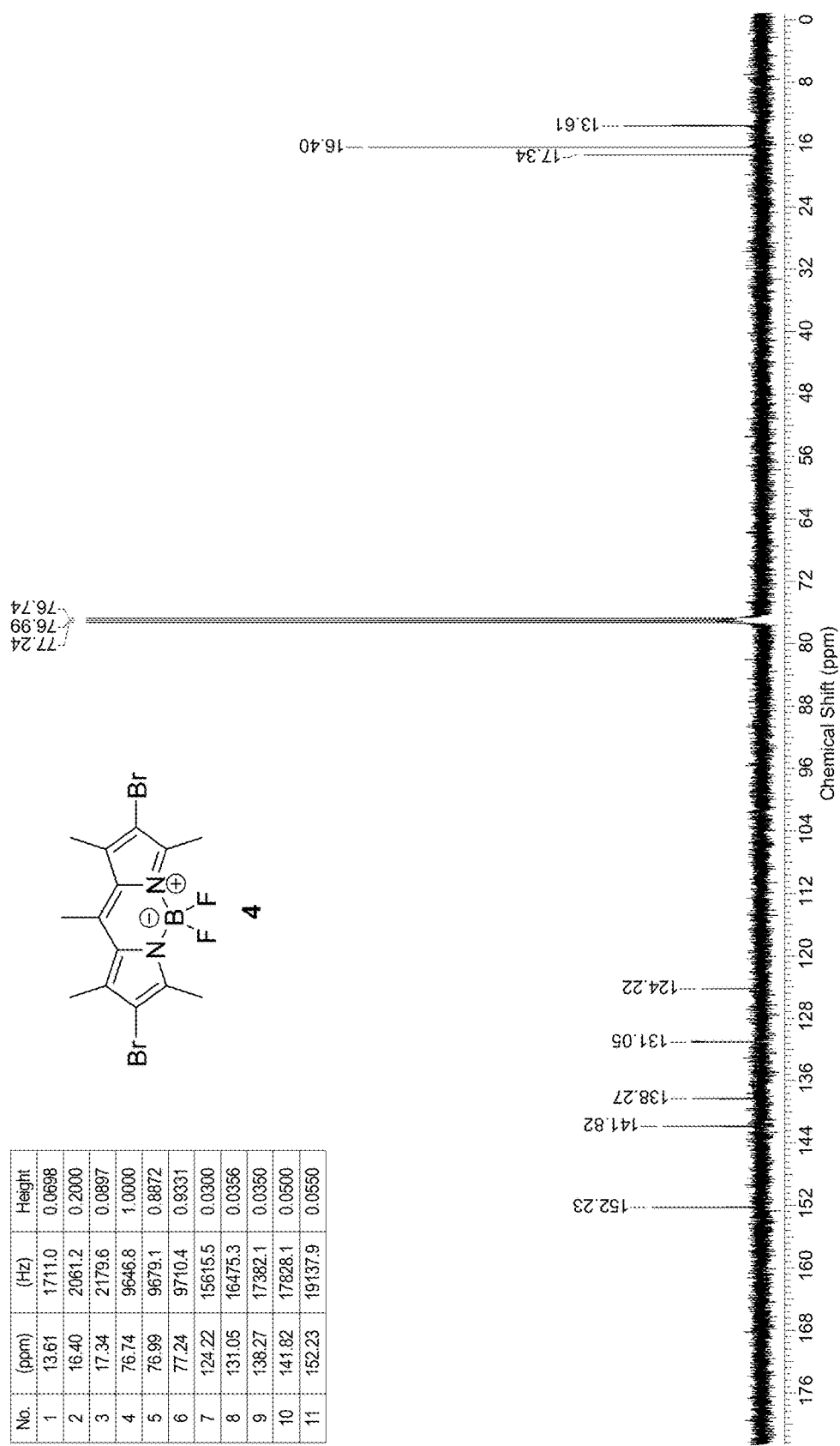
FIG. 5 shows the $^{13}C$ NMR spectrum of compound 4.
Figure 6:
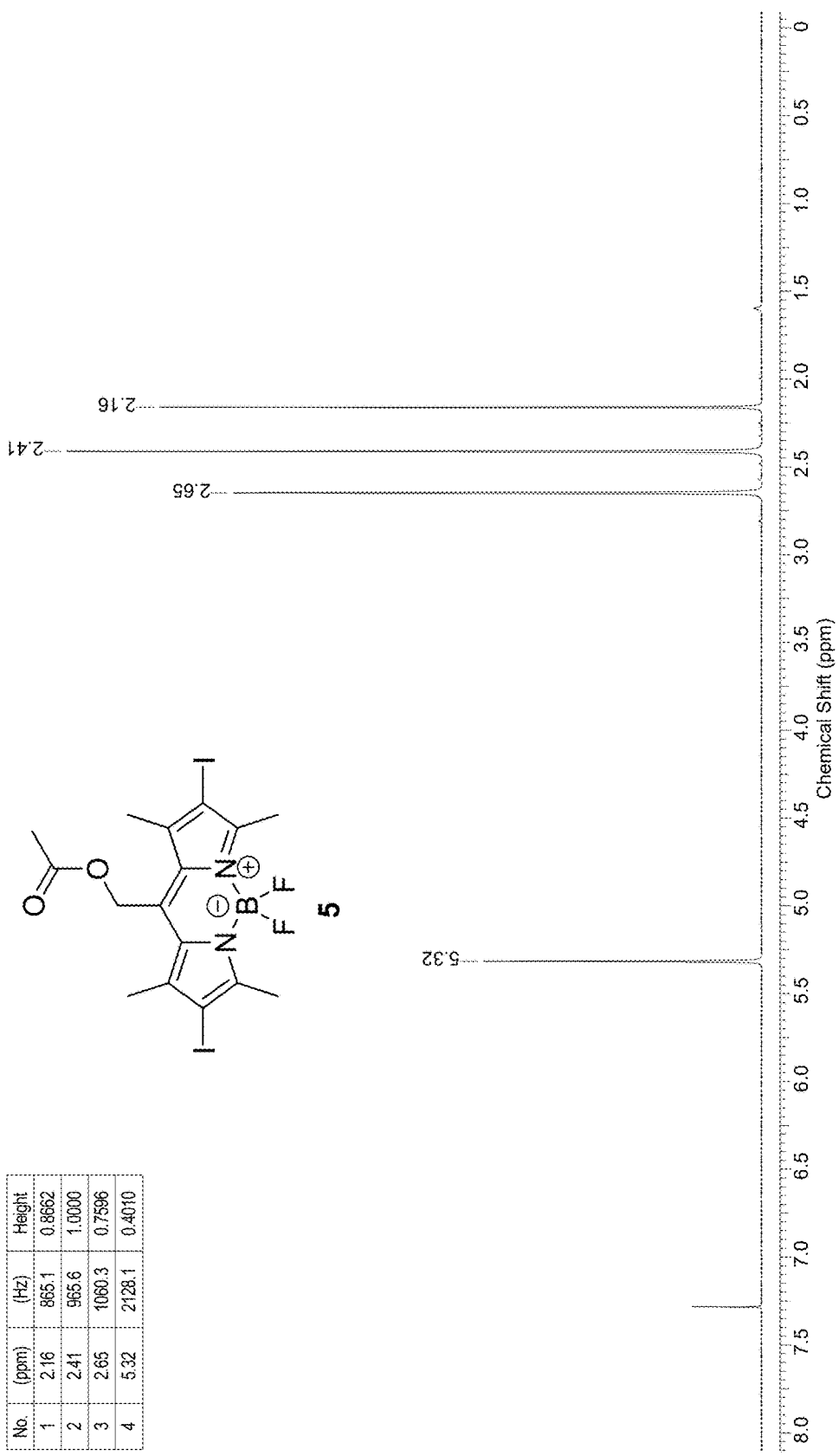
FIG. 6 shows the $^1H$ NMR spectrum of compound 5.
Figure 7:
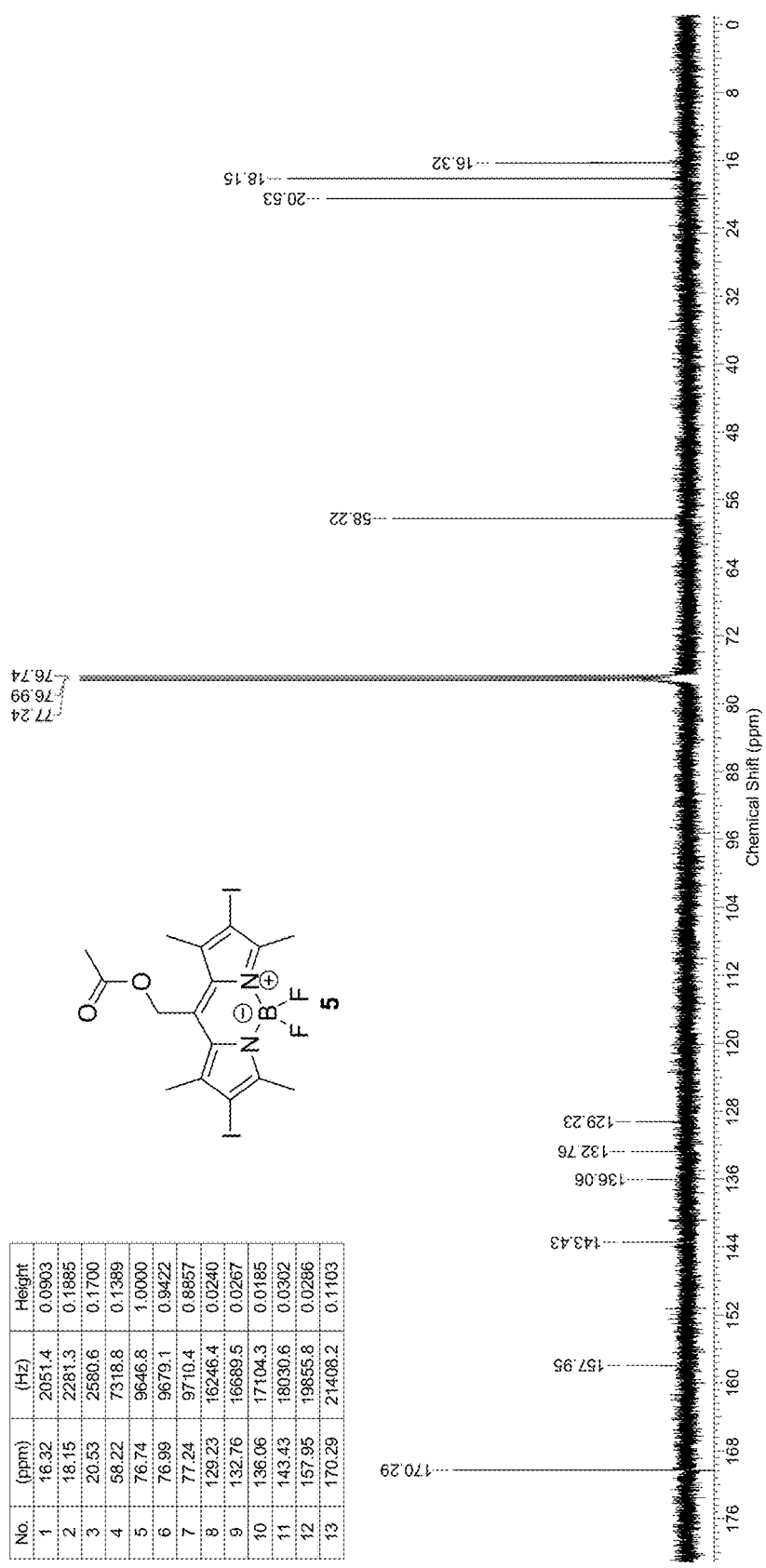
FIG. 7 shows the $^{13}C$ NMR spectrum of compound 5.
Figure 8:
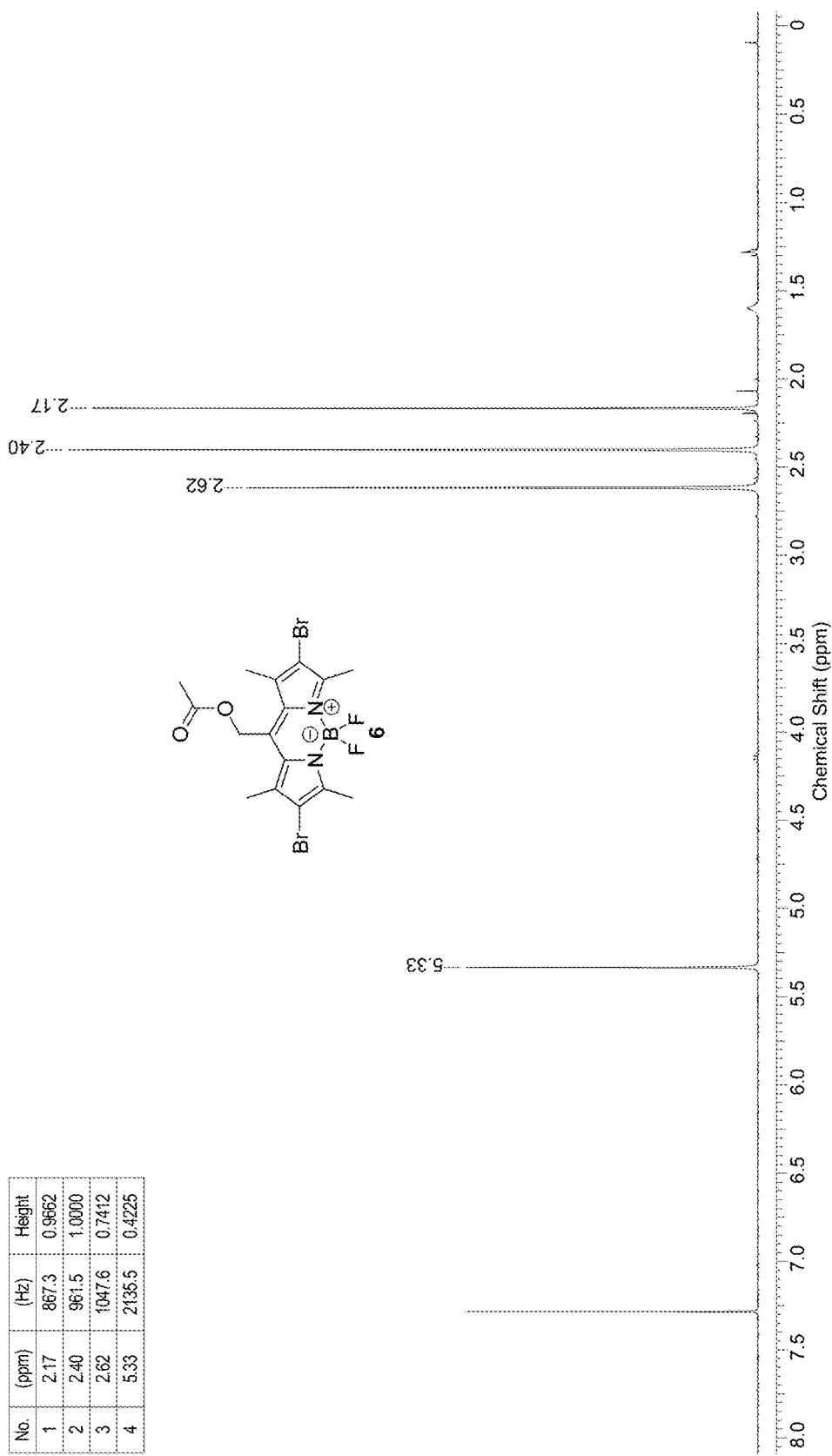
FIG. 8 shows the 1H NMR spectrum of compound 6.
Figure 9:
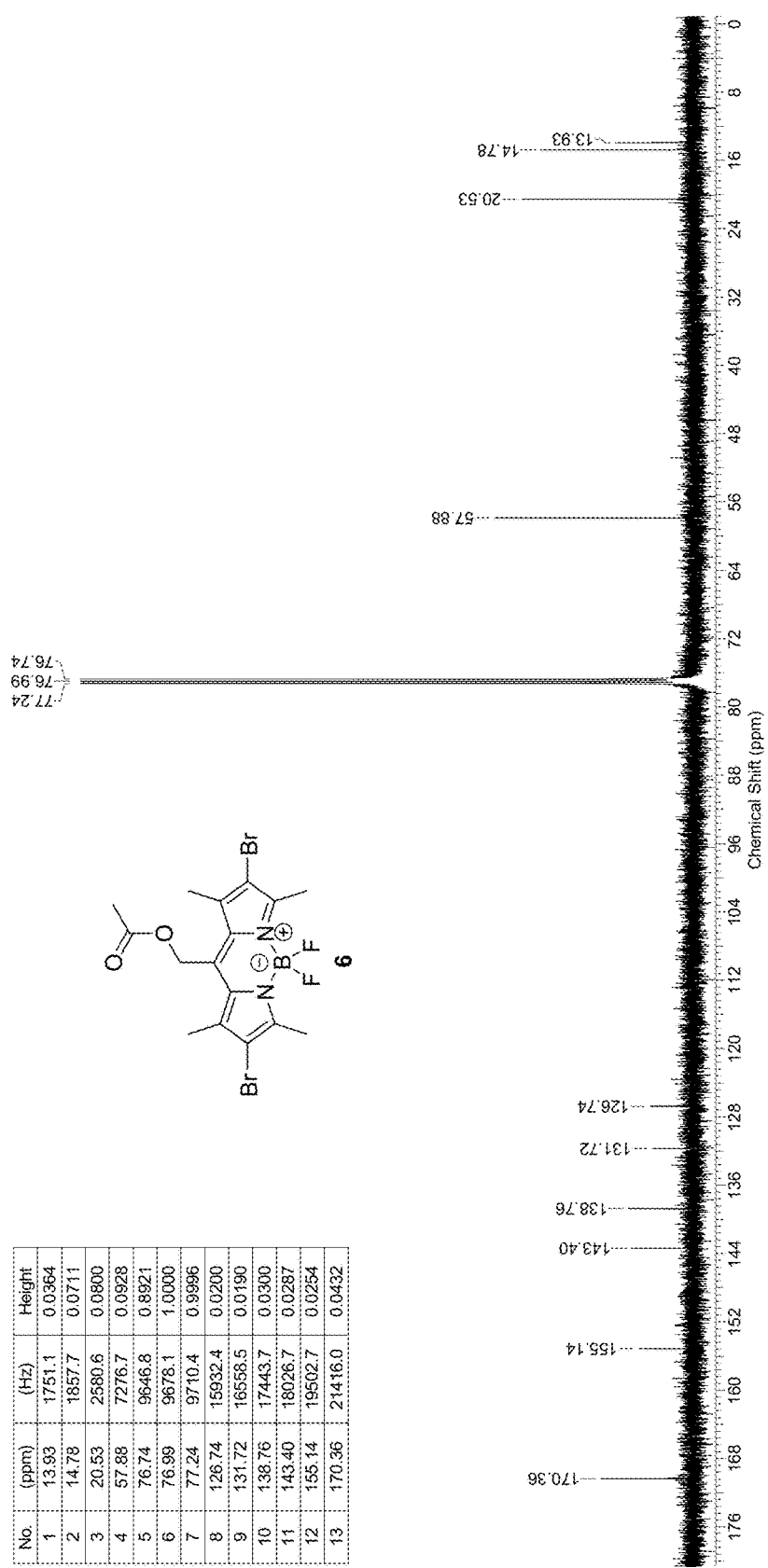
FIG. 9 shows the $^{13}C$ NMR spectrum of compound 6.
Figure 10:
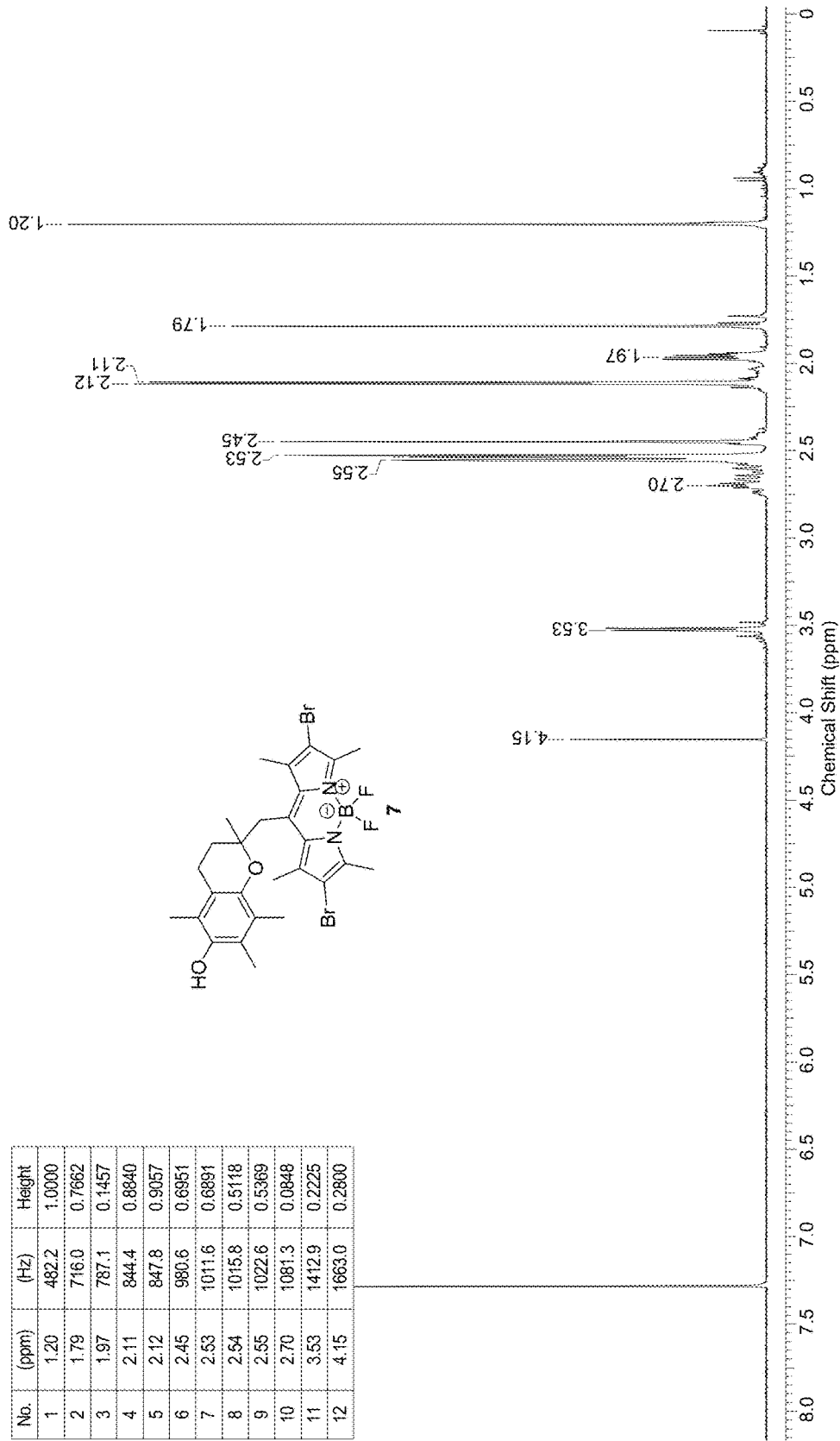
FIG. 10 shows the $^1H$ NMR spectrum of compound 7.
Figure 11:
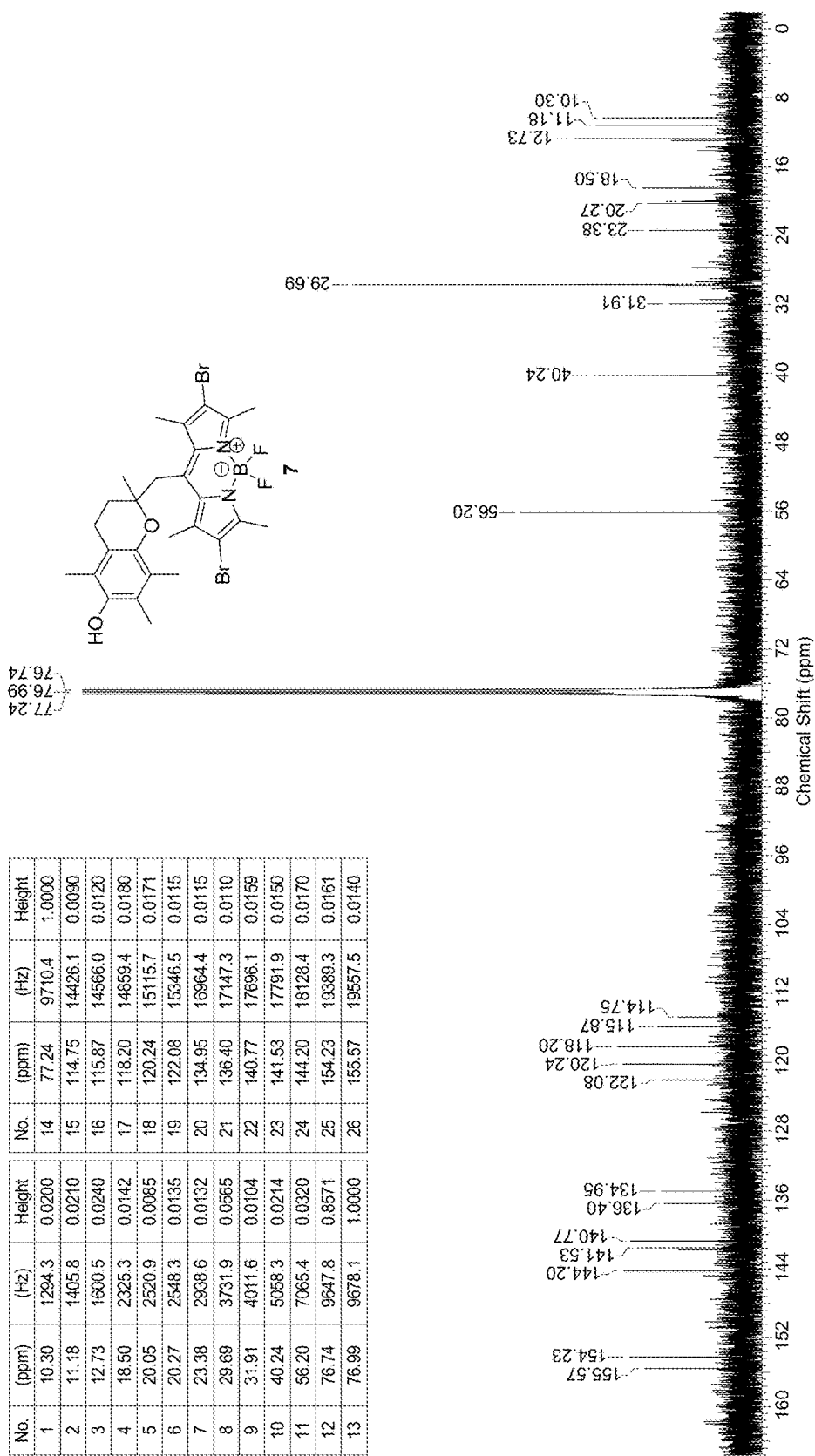
FIG. 11 shows the $^{13}C$ NMR spectrum of compound 7.
Figure 12:
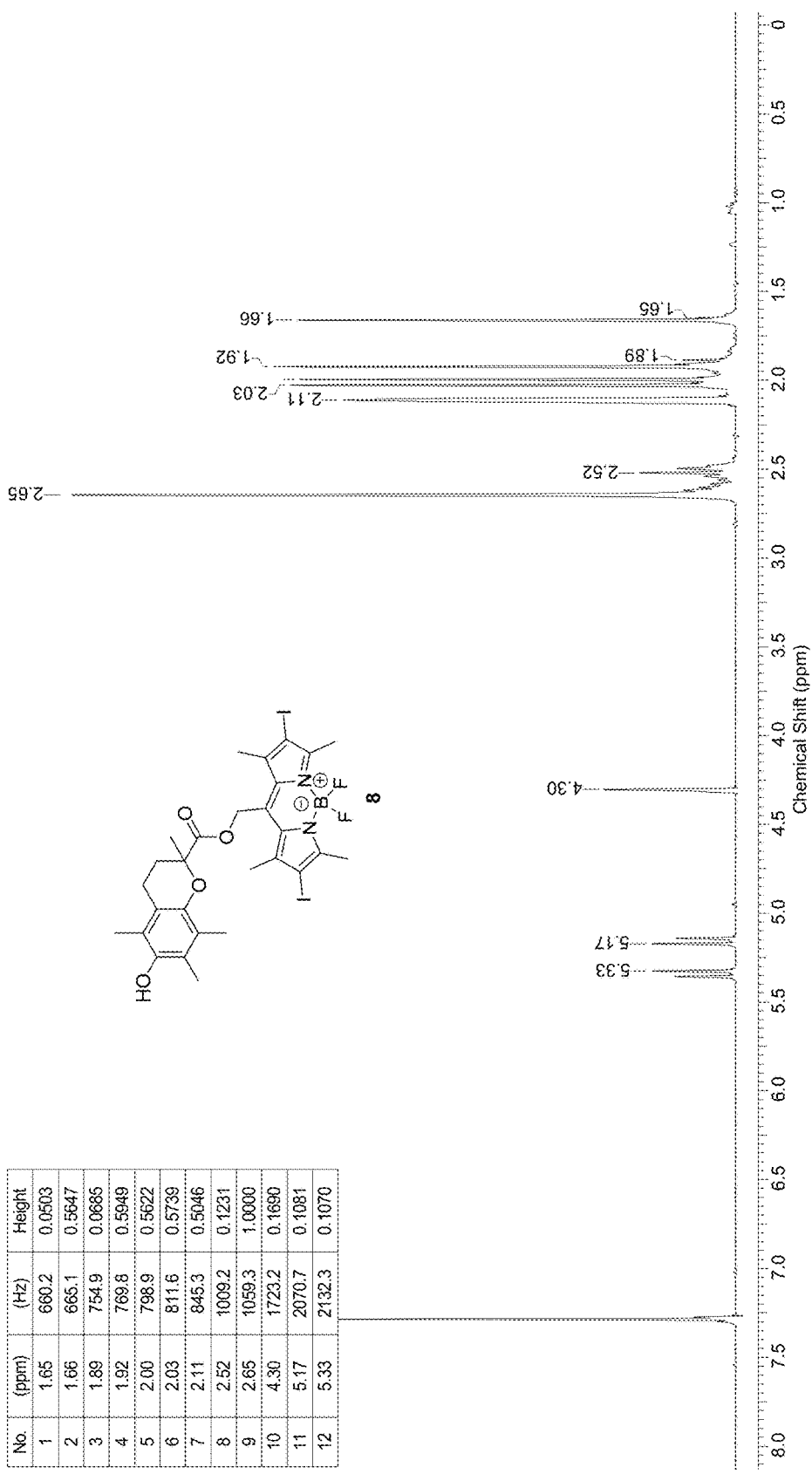
FIG. 12 shows the $^1H$ NMR spectrum of compound 8.
Figure 13:
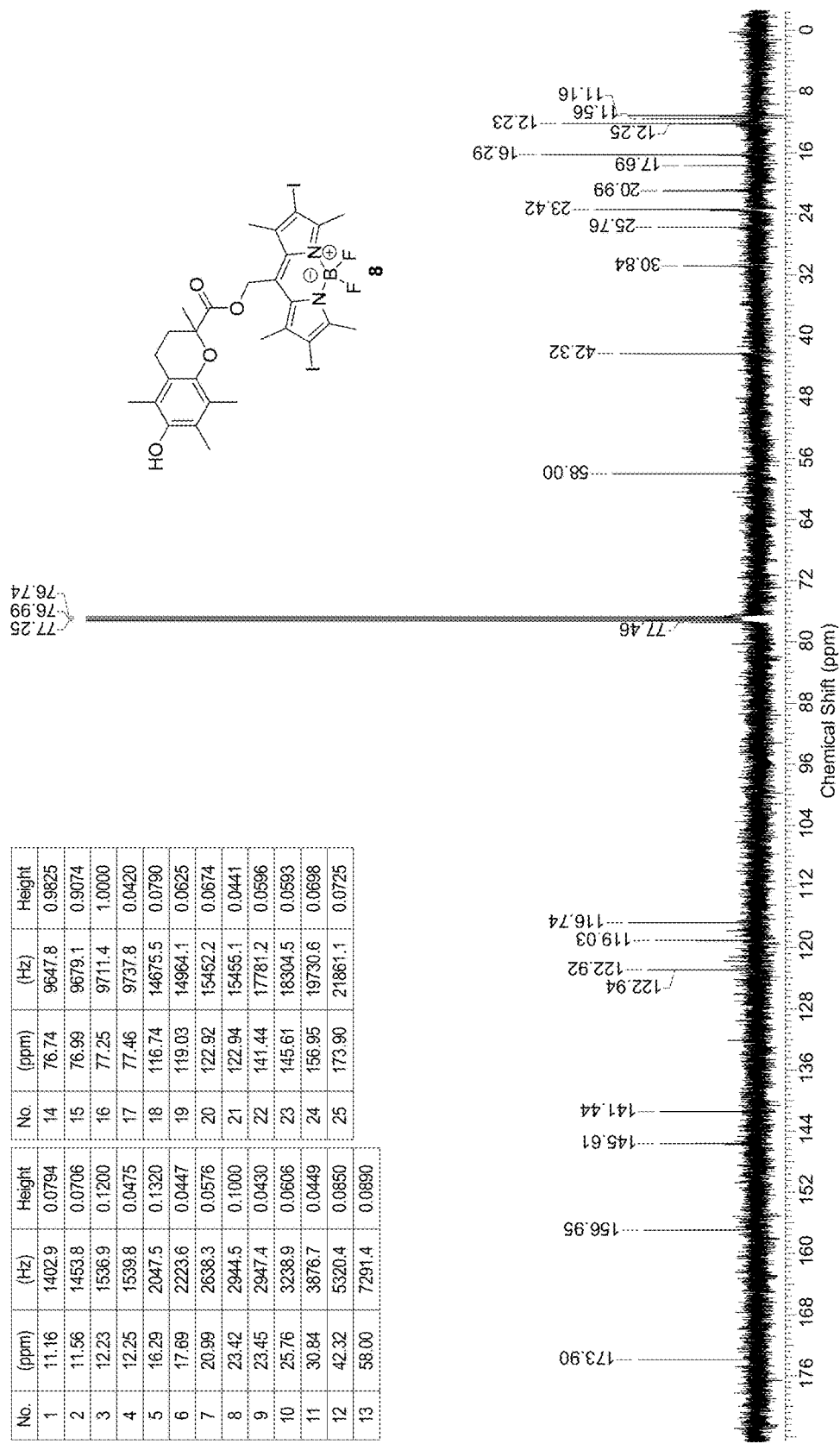
FIG. 13 shows the $^{13}C$ NMR spectrum of compound 8.

Turning now to the invention in more details, there is provided a compound of formula (I):

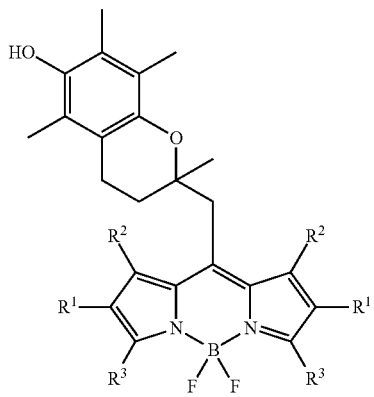

(I)

wherein
both $R^1$ groups are the same and represent —Br or —I,
both $R^2$ groups are the same or different and represent —H or an alkyl group, and
both $R^3$ groups are the same or different and represent an alkyl or a haloalkyl group.

In preferred embodiments, both $R^1$ are —Br, which yield a compound of formula (II):

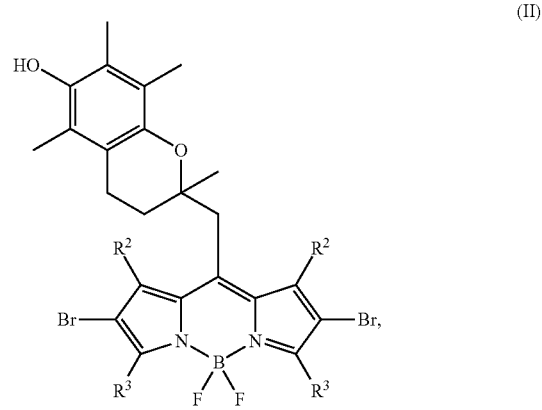

(II)

wherein $R^2$ and $R^3$ are as defined above and below.

In other embodiments, both $R^1$ groups are —I, which yield a compound of formula (III):

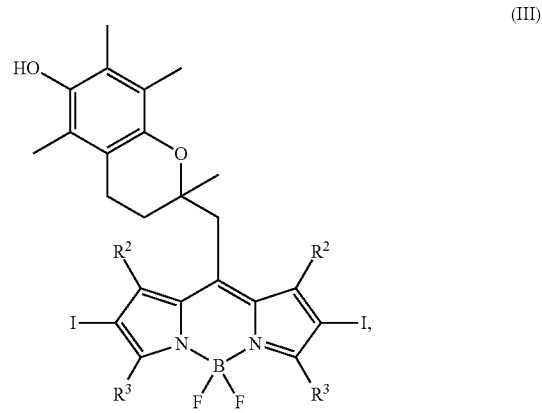

(III)

wherein $R^2$ and $R^3$ are as defined above and below.

The alkyl in $R^2$ may be, for example, a $C_{1-12}$ alkyl group, a $C_{1-6}$ alkyl group, a $C_{1-4}$ alkyl group, a $C_{1-3}$ alkyl group, a $C_{1-2}$ alkyl group, or preferably a $C_1$ alkyl group (i.e. methyl).

The alkyl in $R^3$ may be, for example, a $C_{1-12}$ alkyl group, a $C_{1-6}$ alkyl group, a $C_{1-4}$ alkyl group, a $C_{1-3}$ alkyl group, a $C_{1-2}$ alkyl group, or preferably a $C_1$ alkyl group (i.e. methyl).

Herein, a haloalkyl is an alkyl group substituted with one or more, preferably, one, halogen atom selected from Cl, Br, and I. The alkyl group in the haloalkyl may be, for example, a $C_{1-12}$ alkyl group, a $C_{1-6}$ alkyl group, a $C_{1-4}$ alkyl group, a $C_{1-3}$ alkyl group, a $C_{1-2}$ alkyl group, or preferably a $C_1$ alkyl group (i.e. methyl).

In embodiments, the $R^2$ groups are different from one another. For example, one may H and the other may be an alkyl group; or each $R^2$ group may be a different alkyl group.

In preferred embodiments, both $R^2$ groups are the same. In such embodiments, both $R^2$ may preferably be H, which yield a compound of formula (IV):

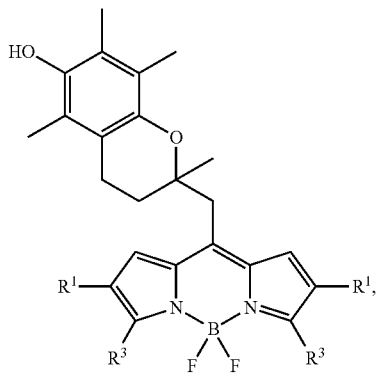

(IV)

wherein $R^1$ and $R^3$ are as defined above and below; or more preferably both $R^2$ groups are a same alkyl group, for example both $R^2$ groups are methyl.

In embodiments, the $R^3$ groups are different from one another. For example, each $R^3$ group may be a different alkyl group, each $R^3$ group may be a different haloalkyl group, or one $R^3$ may be an alkyl group and the other may be a haloalkyl group.

In preferred embodiments, both $R^3$ groups are the same. In such embodiments, both $R^3$ may preferably be methyl.

Preferred embodiments include those where both $R^2$ are —H, both $R^3$ are methyl, and both $R^1$ are —Br or —I, more preferably —Br.

Other preferred embodiments include those where both $R^2$ and both $R^3$ are methyl, and both $R^1$ are —Br or —I, more preferably —Br.

A preferred compound is

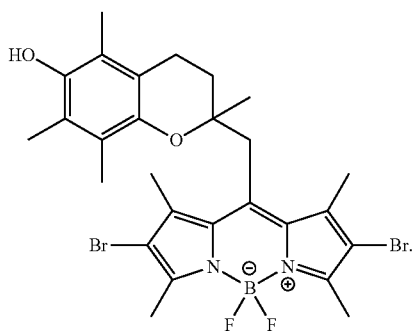 [SMILES: CC1=C(Br)C(C)=[N+]2C1=C(CC1(C)CCc3c(C)c(O)c(C)c(C)c3O1)c1c(C)c(Br)c(C)n1[B-]2(F)F]

It will be apparent to the skilled person that, in this compound (as well as other compounds of the invention) one of the N atoms is positively changed as it bears 4 bonds. However, the boron atom is negatively charged as it bears 4 bonds. Thus, the compound is overall neutral.

Use in Photodynamic Therapy

In a second related aspect of the invention, there is provided the use of the above compounds as photosensitizers, more specifically singlet oxygen ($^1O_2$) photosensitizers, in photodynamic therapy. Herein, a "singlet oxygen ($^1O_2$) photosensitizer" is a compound that produces singlet oxygen ($^1O_2$) when excited by light.

The new compounds are two-segment photosensitizer-trap molecules. The photosensitizer segment consists of a halogen substituted boron-dipyrromethene (BODIPY) dye. The trap segment consists of the chromanol ring of α-tocopherol, which acts as an intramolecular quenching switch and as a reactive oxygen species (ROS) scavenger.

In use, the above compounds are first dormant (non-active). Indeed, the trap segment ensures that the photosensitizer segment will be dormant until activated—details on the mechanism involved are provided in Example 1 below.

Then, the above compounds are activated to become active singlet oxygen ($^1O_2$) photosensitizers. More specifically, the compounds are activated in response to a chemical cue, more precisely reactive oxygen species (ROS), that is specific to the targeted cells/tissues to be treated. In fact, these ROS will oxidize the trap segment. Oxidation of the trap segment with ROS restores the ability of the compound to sensitize $^1O_2$ and render it unable to scavenge $^1O_2$, effectively activating the otherwise dormant photosensitizer.

Then, the above compounds are exposed to light and, as a result, the dye segment will photosensitize $^1O_2$ i.e. produce the desired $^1O_2$, that will effect the desired local treatment of the targeted cells/tissues. The substitution of the boron-dipyrromethene (BODIPY) dye by halogen atoms ensures that rapid and efficient intersystem crossing to the triplet manifold will take place upon photoexcitation of the chromophore. This results in at least ~40-fold enhancement in $^1O_2$ production. The juxtaposed antioxidant-pro-oxidant antagonistic chemistry of these compounds enables the autocatalytic ROS ($^1O_2$) amplification under continuous photoexcitation as ROS (including $^1O_2$) consumption triggers the photosensitization of $^1O_2$.

In summary, the trap segment is an intramolecular switch that provides a control layer to ensure the photosensitizer compound is active only in the right cells/tissues (those containing ROS that activate the compounds of the invention). This switch, together with the temporal and spatial control of light exposure, allows to selectively and specifically target the tissue to be treated.

The compounds of the invention are thus versatile ROS-activatable photosensitizers with potential application in tissues where metabolic imbalance leads to a rather large ROS production. These dormant singlet oxygen photosensitizers, that activate upon scavenging of ROS, should indeed be of use in the targeted delivery of $^1O_2$ to cells/tissues that are under oxidative stress associated with increased metabolic activity and ROS generation. This will enable treating tissues and/or cells characterized by their overproduction of reactive oxygen species (ROS) in a selective manner. Indeed, exacerbated ROS production in these tissues/cells will lead to selective activation of the otherwise dormant photosensitizer, enabling photosensitized inactivation of the tissue/cell made susceptible to the photosensitizer by ROS. Therefore, the compounds of the invention can potentially be used as photosensitizer in the photodynamic treatment of diseases or conditions in which the killing/destruction of cells exhibiting increased levels of ROS (relative to normal cells), thus cells under oxidative stress. Oxidative stress reflects an imbalance between the systemic manifestation of reactive oxygen species and a biological system's ability to readily detoxify the reactive intermediates or to repair the resulting damage. Example of disease and conditions to be treated with the compounds of the invention include e.g.:

Pathogenic infections, such as viral, parasitic, fungal or bacterial infection, e.g. in wounds, which are known to produce ROS upon infecting/inflaming cells/tissues in a subject, skin conditions, such as psoriasis, vitiligo and acne;

drug resistant bacteria—bactericidal treatment of bacteria is known to stimulate generation of ROS in these bacteria, making them susceptible to the dormant photosensitizer action. While non-resistant bacteria will be eliminated by the bactericidal, drug resistant populations will be selectively inactivated (with no or minimal collateral tissue damage) by the combined action of the activated photosensitizer and light; and cancer cells, which are known to have an exacerbated production of ROS as they are under oxidative stress associated with increased metabolic activity and ROS generation Thus, there is provided method for the selective delivery of singlet oxygen ($^1O_2$) to cells having an increased reactive oxygen species (ROS) concentration (such as those noted above), the method comprising the steps of:

a) contacting said cells having an increased ROS concentration with a compound of the invention, thereby allowing the reactive oxygen species to locally activate said compound, and b) exposing the activated compound to light, thereby producing and selectively delivering singlet oxygen to the cells having an increased ROS concentration.

There is also provided a method for killing cells under oxidative stress conditions (such as those noted above), the method comprising the steps of:

a) contacting said cells with a compound of the invention, and b) exposing the cells to light.

In these methods, as noted above, ROS activate the compound of the invention and exposition of the activated compound to light produces singlet oxygen, which damages the treated cells thus killing/inactivating/destroying them. The normal cells (not under oxidative stress, not having an increase ROS concentration) are untouched, even if they are exposed to light and are in contact with the compound because they are devoid of ROS to activate the compound. In other words, in normal tissues, the compound remains dormant.

In embodiments of these methods, step a) comprises the administration of the compound to a subject. Said administration may be systemic or local (for example topical).

There is also provided a photosensitizing composition for use in photodynamic therapy, the composition comprising the above compound, optionally together with biological acceptable carrier. The composition may be for systemic or local (for example topical) administration. It may be a cosmeceutical or pharmaceutical composition.

Definitions

The use of the terms "a" and "an" and "the" and similar referents in the context of describing the invention (especially in the context of the following claims) are to be construed to cover both the singular and the plural, unless otherwise indicated herein or clearly contradicted by context.

The terms "comprising", "having", "including", and "containing" are to be construed as open-ended terms (i.e., meaning "including, but not limited to") unless otherwise noted.

Recitation of ranges of values herein are merely intended to serve as a shorthand method of referring individually to each separate value falling within the range, unless otherwise indicated herein, and each separate value is incorporated into the specification as if it were individually recited herein. All subsets of values within the ranges are also incorporated into the specification as if they were individually recited herein.

Similarly, herein a general chemical structure with various substituents and various radicals enumerated for these substituents is intended to serve as a shorthand method of referring individually to each and every molecule obtained by the combination of any of the radicals for any of the substituents. Each individual molecule is incorporated into the specification as if it were individually recited herein. Further, all subsets of molecules within the general chemical structures are also incorporated into the specification as if they were individually recited herein.

All methods described herein can be performed in any suitable order unless otherwise indicated herein or otherwise clearly contradicted by context.

The use of any and all examples, or exemplary language (e.g., "such as") provided herein, is intended merely to better illuminate the invention and does not pose a limitation on the scope of the invention unless otherwise claimed.

No language in the specification should be construed as indicating any non-claimed element as essential to the practice of the invention.

Herein, the term "about" has its ordinary meaning. In embodiments, it may mean plus or minus 10% or plus or minus 5% of the numerical value qualified.

Unless otherwise defined, all technical and scientific terms used herein have the same meaning as commonly understood by one of ordinary skill in the art to which this invention belongs.

Other objects, advantages and features of the present invention will become more apparent upon reading of the following non-restrictive description of specific embodiments thereof, given by way of example only with reference to the accompanying drawings.

DESCRIPTION OF ILLUSTRATIVE EMBODIMENTS

The present invention is illustrated in further details by the following non-limiting examples.

Example 1—ROS-Mediated Activation of a Dormant Singlet Oxygen Photosensitizer ($Br_2B$-PMHC, Compound 7)

Here we show the design, preparation, and characterization of a dormant singlet oxygen ($^1O_2$) photosensitizer that is activated upon its reaction with reactive oxygen species (ROS), including $^1O_2$ itself, in what constitutes an autocatalytic process. The compound is based on a two segment photosensitizer-trap molecule where the photosensitizer segment consists of a Br-substituted BODIPY dye. The trap segment consists of the chromanol ring of α-tocopherol, the most potent naturally occurring lipid soluble antioxidant.

Time-resolved absorption, fluorescence, and $^1O_2$ phosphorescence studies together with fluorescence and $^1O_2$ phosphorescence emission quantum yields collected on $Br_2B$-PMHC and related bromo and iodo-substituted BODIPY dyes show that the trap segment provides a total of three layers of intramolecular suppression of $^1O_2$ production. Oxidation of the trap segment with ROS restores the sensitizing properties of the photosensitizer segment resulting in ~40-fold enhancement in $^1O_2$ production.

The juxtaposed antioxidant (chromanol) and prooxidant (Br-BODIPY) antagonistic chemical activities of the two-segment compound enable the autocatalytic, and in general ROS-mediated, activation of $^1O_2$ sensitization providing a chemical cue for the spatiotemporal control of $^1O_2$. The usefulness of this approach to selectively photoactivate the production of singlet oxygen in ROS stressed vs regular cells was successfully tested via the photodynamic inactivation of ROS stressed Gram negative *E. coli* strain.

Introduction

We aimed to produce a dormant singlet oxygen photosensitizer that activates upon scavenging of ROS and could thus potentially be utilized towards the controlled delivery of $^1O_2$ specifically in cells/tissues, such as cancer cells that are under oxidative stress associated with increased metabolic activity and ROS generation. Here we show the design of the compound Br$_2$B-PMHC (compound 7) that operates under this premise (see FIG. 1).

The new compound is based on a two-segment photosensitizer-trap molecule. The photosensitizer segment consists of a Br substituted boron-dipyrromethene (BODIPY) dye, where substitution by heavy atoms ensures that rapid and efficient intersystem crossing to the triplet manifold will take place upon photoexcitation of the chromophore. The trap segment consists of the chromanol ring of α-tocopherol, the most potent naturally occurring lipid soluble antioxidant and an efficient ROS scavenger.

Photoinduced electron transfer (PeT) from the chromanol segment to the BODIPY segment is shown to effectively compete with intersystem crossing effectively reducing the yield of triplet state. Photoinduced electron transfer is also shown to quench any residual triplet excited state formed. Combined, singlet and triplet quenching of the excited photosensitizer segment by the chromanol ring of α-tocopherol is shown to give two layers of prevention of $^1O_2$ production. Importantly, α-tocopherol, known to be an efficient physical quencher of $^1O_2$, provides a third layer of suppression of $^1O_2$ production.

Oxidation of the trap segment with ROS restores the ability of the compound to sensitize $^1O_2$ and aborts its ability to scavenge $^1O_2$ effectively activating the otherwise dormant photosensitizer (FIG. 1).

More specifically, FIG. 1 shows the proposed mechanism for autocatalytic $^1O_2$ amplification: Following photoexcitation of Br$_2$B-PMHC, its singlet excited state rapidly deactivates via intramolecular photoinduced electron transfer (PeT). PeT is also proposed to take place from the triplet excited state if at all formed. Any Br$_2$B-PMHC in the triplet manifold ([Br$_2$B-PMHC]$^{3*}$) that eludes the previous two decay pathways will sensitize $^1O_2$ that will next be scavenged through a physical process by the trap segment in Br$_2$B-PMHC (geminate reaction). The improbable occurrence of a chemical quenching pathway of $^1O_2$ by Br$_2$B-PMHC will yield an oxidized, active form Br2B-PMHCox that will sensitize additional $^1O_2$.

The photophysical and reactivity studies described herein show that Br$_2$B-PMHC is a versatile ROS-activatable photosensitizer of potential application in tissues where metabolic imbalance leads to a large ROS production, such as in cancer cells[17-21] and wounded tissue.[38-40] The juxtaposed antioxidant-pro-oxidant antagonistic chemistry of Br$_2$B-PMHC enables the autocatalytic ROS ($^1O_2$) amplification under continuous photoexcitation as ROS (including $^1O_2$) consumption triggers the photosensitization of $^1O_2$.

Experimental Section

More details will be provided in the <<Supporting Information>> section below.

Materials

HPLC grade solvents for spectroscopy experiments and column chromatography purifications were purchased from Fisher Scientific. All other chemicals were supplied by Sigma-Aldrich, Co. and used without further purification.

Synthesis of Compounds 1-8

Compound 1

1,3,5,7,8-pentamethyl-Pyrromethene Fluoroborate (H$_2$B—CH$_3$) was prepared as described in the literature: (82) Nepomnyashchii, A. B.; Broring, M.; Ahrens, J.; Bard, A. J. J. Am. Chem. Soc. 2011, 133, 8633 and (83) Nepomnyashchii, A. B.; Bard, A. J. Acc. Chem. Res. 2012, 45, 1844, which are included herein by incorporation.

Compound 2

8-Acetoxymethyl-1,3,5,7-tetramethyl Pyrromethene Fluoroborate (H$_2$B—OAc) was prepared as described in the literature: Krumova, K.; Cosa, G. J. Am. Chem. Soc. 2010, 132, 17560, which is included herein by incorporation.

Compound 3:
2,6-diiodo-1,3,5,7,8-pentamethyl-pyrromethene fluoroborate (I$_2$C—CH$_3$)

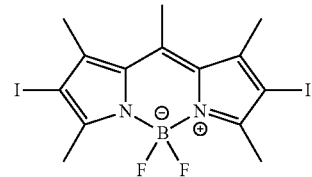

3

Iodic acid (2.0 equiv) dissolved in a minimum amount of water was added dropwise over 20 min to a solution of 1 (1.0 equiv) and iodine (2.5 eq.) in 6 ml of EtOH. This mixture was then warmed for 2 hours at 25° C. After cooling, the mixture was evaporated under reduced pressure. The crude product was purified by silica gel chromatography using 10% ethyl acetate/hexane as the eluent and recrystallized from chloroform and n-hexane to afford I$_2$B—OAc as bright red needles (yield 72%). $^1$H NMR (CDCl$_3$, 400 MHz) δ ppm 2.67 (s, 3H), 2.64 (s, 6H), 2.50 (s, 6H); $^{13}$C NMR (CDCl$_3$, 126 MHz): δ ppm 155.04, 142.91, 141.10, 132.13, 122.39, 19.82, 17.86, 16.01; HRMS (ESI) for C$_{16}$H$_{17}$BI$_2$F$_2$N$_2$O$_2$Na (M$^+$+Na) calcd 536.9287. found 536.9453.

Compound 4: 2,
6-dibromo-1,3,5,7,8-pentamethyl-pyrromethene fluoroborate (Br$_2$C—CH$_3$)

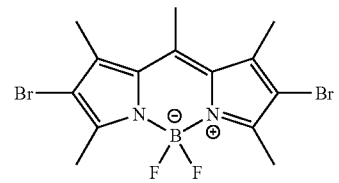

4

To 1 (1 equiv) in 40 mL of dry CH$_2$Cl$_2$ was added dropwise liquid bromine (3 equiv) in CH$_2$Cl$_2$ (5 mL) over a period of 1 h. The mixture was left stirring for an additional 2 h under Ar at room temperature, washed with an aqueous solution of sodium thiosulfate, and extracted with $CH_2Cl_2$. Organic layers were combined, dried over $Na_2SO_4$, and evaporated to dryness. Purification was performed by column chromatography on silica gel using 10% ethyl acetate/hexane as eluent, from which the desired product $Br_2B$—OAc was obtained as red solid in 88% yield. $^1H$ NMR ($CDCl_3$, 400 MHz) δ ppm 2.67 (s, 3H), 2.60 (s, 6H), 2.47 (s, 6H); $^{13}C$ NMR ($CDCl_3$, 126 MHz): δ ppm 152.23, 141.28, 138.27, 131.05, 124.22, 17.34, 16.40, 13.61; HRMS (ESI) for $C_{14}H_{15}BBr_2F_2N_2Na$ ($M^+$+Na) calcd 442.8921. found 442.9235.

Compound 5:
8-Acetoxymethyl-2,6-diiodo-1,3,5,7-tetramethyl Pyrromethene Fluoroborate ($I_2B$—OAc)

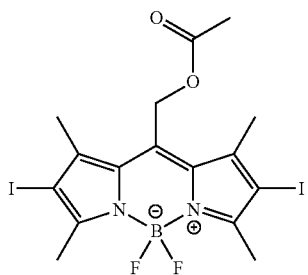

5

5 was obtained following the same procedure used to synthesize 3 with 2 as starting material. The product was afforded as bright red needles in 79% yield: $^1H$ NMR ($CDCl_3$, 400 MHz) δ ppm 5.32 (s, 2H), 2.65 (s, 6H), 2.41 (s, 6H), 2.16 (s, 3H); $^{13}C$ NMR ($CDCl_3$, 126 MHz): δ ppm 170.29, 157.95, 143.43, 136.06, 132.76, 129.23, 58.22, 20.53, 18.15, 16.32; HRMS (ESI) for $C_{16}H_{17}BI_2F_2N_2O_2Na$ ($M^+$+Na) calcd 594.9298. found 594.9334.

Compound 6:
8-Acetoxymethyl-2,6-dibromo-1,3,5,7-tetramethyl Pyrromethene Fluoroborate ($Br_2B$—OAc)

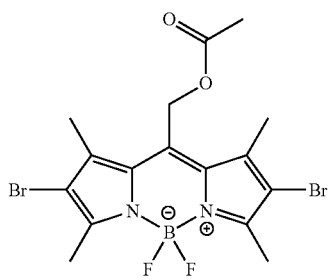

6

6 was obtained following the same procedure used to synthesize 3 with 2 as starting material. The desired product $Br_2B$—OAc was obtained as red solid in 93% yield: $^1H$ NMR ($CDCl_3$, 400 MHz,) δ ppm 5.33 (s, 2H), 2.62 (s, 6H), 2.40 (s, 6H), 2.17 (s, 3H); $^{13}C$ NMR ($CDCl_3$, 126 MHz) δ ppm 170.36, 155.14, 143.40, 138.76, 131.72, 57.88, 20.53, 14.78, 13.93 ppm; HRMS (ESI) for $C_{16}H_{17}BBr_2F_2N_2O_2Na$ ($M^+$.Na) calcd 498.9614. found 498.9613.

Compound 7: 8-((6-Hydroxy-2,5,7,8-tetramethyl-chroman-2-yl)-methyl)-2,6-dibromo-1,3,5,7-tetramethyl ($Br_2B$-PMHC)

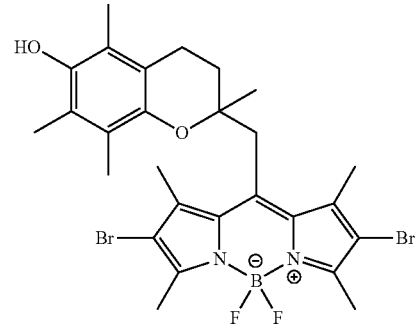 [SMILES: CC1=C(Br)C(C)=[N+]2C1=C(CC1(C)CCc3c(C)c(O)c(C)c(C)c3O1)c1c(C)c(Br)c(C)n1[B-]2(F)F]

7

8-((6-Hydroxy-2,5,7,8-tetramethylchroman-2-yl)-methyl)-1,3,5,7-tetramethyl Pyrromethene Fluoroborate ($H_2B$-PMHC) was prepared as describe in the literature: (85) Krumova, K.; Friedland, S.; Cosa, G. J. Am. Chem. Soc. 2012, 134, 10102, which is included herein by reference. The bromine atoms were added to $H_2B$-PMHC following the procedure described above to obtain $Br_2B$—OAc. $Br_2B$-PMHC was obtained as a red solid in 15% yield.

$^1H$ NMR (400 MHz, $CDCl_3$) δ ppm 4.15 (s, 1H), 3.47-3.53 (m, 2H), 2.60-2.76 (m, 2H), 2.55 (s, 3H), 2.54 (s, 3H), 2.53 (s, 3H), 2.45 (s, 3H), 2.12 (s, 3H), 2.11 (s, 3H), 1.90-1.98 (m, 3H), 1.79 (s, 3H), 1.20 (s, 3H); $^{13}C$ NMR ($CDCl_3$, 126 MHz): δ ppm 155.57, 154.23, 144.20, 141.53, 140.77, 136.40, 134.95, 122.08, 120.24, 118.20, 115.87, 114.75, 77.24, 76.99, 76.74, 56.20, 40.24, 31.91, 29.69, 23.68, 20.27, 20.05, 18.50, 12.73, 11.18, 10.30; HRMS (ESI) for $C_{27}H_{31}BBr_2F_2N_2O_2$ ($M^-$) calcd 622.0821. found 621.0743.

Compound 8: 8-((±)-6-Hydroxy-2,5,7,8-tetramethyl-chromane-2-carbonyloxy)-2,6-diiodo-methyl-1,3,5,7-tetramethylpyrromethene Fluoroborate ($I_2B$-TOH)

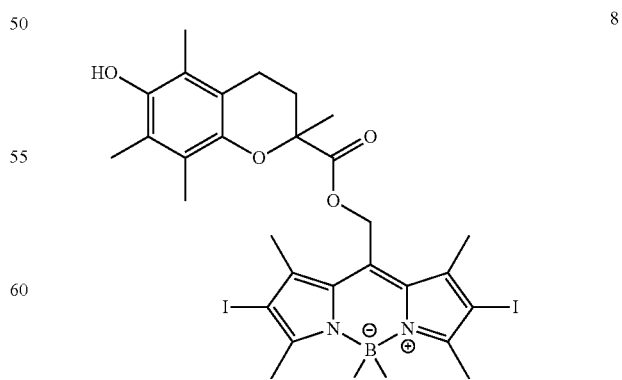

8

Hydrolysis of 2 was conducted as described in the literature.[4] The iodine atoms were added to $H_2B$—OH following the procedure described above to obtain I$_2$B—OAc. 8-Hydroxymethyl-2,6-diiodo-1,3,5,7-tetramethyl Pyrromethene Fluoroborate (I$_2$B—OH) was obtained in 94% yield. Trolox (1.5 equiv), I$_2$B—OH (1 equiv), and 4-(N,N-dimethylamino)pyridine (DMAP) (0.2 equiv) were dissolved in 1.5 mL of dry THF under argon. 1-ethyl-3-(3-dimethylaminopropyl)carbodiimide (EDC) (1 equiv) was added dropwise to the solution. The reaction was left stirring at room temperature for 2 h. The crude product was loaded onto a silica gel flash column and eluted with 30% ethyl acetate/hexane (60% yield): $^1$H NMR (CDCl$_3$, 400 MHz) δ ppm 5.33 (d, J=5 MHz, 1H), 5.17 (d, J=4.8 MHz, 1H), 4.30 (s, 1H), 2.65 (s, 7H), 2.46-2.54 (m, 2H), 2.11 (s, 6H), 2.03 (s, 3H), 2.00 (s, 3H), 1.92 (s, 3H), 1.90-1.92 (m, 1H), 1.66 (s, 3H); $^{13}$C NMR (CDCl$_3$, 126 MHz): δ ppm 173.9, 156.9, 145.6, 141.4, 122.9, 122.9, 119.0, 116.7, 77.5, 77.3, 77.0, 76.7, 58.0, 42.3, 30.8, 25.8, 23.4, 23.4, 21.0, 17.7, 16.3, 12.2, 12.2, 11.6, 11.2; HRMS (ESI) for C$_{28}$H$_{31}$BF$_2$I$_2$N$_2$O$_4$ (M$^-$) calcd 762.0401. found 761.0367.

The $^1$H NMR and $^{13}$C NMR spectra of compounds 3-8 are provided in FIGS. 2 to 13.

Instrumentation

Absorption spectra were recorded using a Hitachi U-2800 UV-vis-NIR spectrophotometer. Luminescence spectra were recorded using a PTI QuantaMaster spectrofluorimeter using 10×10 mm quartz cuvettes and corrected for detector sensitivity.

Fluorescence lifetime measurements were carried out using a Picoquant Fluotime 200 time correlated single photon counting (TCSPC) setup employing an LDH-P-C-470 picosecond diode laser (Picoquant) with an excitation wavelength at 466 nm as the excitation source. The laser was controlled by a PDL 800 B picosecond laser driver from Picoquant. $^1$HNMR spectra were recorded on a Bruker AV 400 instrument at 400 MHz. $^{13}$CNMR spectra were recorder on a Varian VNMRS 500 instrument at 125 MHz. ESI mass spectra were measured on a Bruker maXis impact. Laser Flash Photolysis (LFP) experiments were carried out in a commercially available Luzchem 212 LFP setup provided with a Tektronix TDS 2000 digitizer for signal capture. A Nd:Yag laser (Continuum model Surelite I-10 using a second harmonic generators, model number SL-SHG-T1) was used for excitation at a wavelength of 532 nm. Phosphorescence experiments were recorded using a Cary Eclipse Fluorescence Spectrophotometer. Singlet Oxygen phosphorescence was recorded with a Hamamatsu NIR detector (peltier cooled at −62.8° C. operating at 800 V, coupled to a grating monochromator) upon excitation with a 532 nm Nd:YAG laser. A customized Luzchem Research LFP-111 system was employed to collect and process the data.

Steady-State and Time-Resolved Fluorescence Studies

The steady-state fluorescence spectra were recorded between 500-800 nm (depending on each compound) upon exciting at the wavelength of the absorbance maxima. The excitation and emission slits were tuned according to the fluorescence quantum yield of each BODIPY (i.e. for compound 7 excitation slits were 5 nm and for compound 4 we used 2 nm). Fluorescence was recorded every 1 nm using 0.1 s integration time. For the Fluorescence lifetime measurements, the excitation rate was 10 MHz, and the detection frequency was less than 100 kHz. Photons were collected at the magic angle. The fluorescence decay traces were fit using FluoFit (Picoquant) software. For steady-state and time-resolved fluorescence measurements a quartz cuvette with a 10 mm path length was used and all the solutions were prepared in air equilibrated acetonitrile.

Fluorescence Quantum Yield

Quantum yields of fluorescence were measured using PM605 in acetonitrile as a reference. Absorption and emission spectra of PM605 and the dye of interest were measured in acetonitrile at five different concentrations. The integrated intensity versus absorbance were then plotted and fitted linearly. Relative quantum yields of fluorescence for the unknown with respect to the standard were obtained from equation 1, where φ, Δ, and n refer, respectively, to the quantum yield, the slope obtained from the above-mentioned plot, and the solvent refractive index for the unknown (x) or standard (st).

$$\Phi_x = \Phi_{st} \times \frac{\Delta_x}{\Delta_{st}} \times \frac{n_x^2}{n_{st}^2} \quad \text{(Equation 1)}$$

Laser Flash Photolysis Studies

The 500 mJ/pulse laser output was attenuated yielding 10 mJ laser pulses of 6 ns in duration. Samples were prepared in acetonitrile. The final absorbance of the BODIPY dyes was 0.1. The concentration was kept low to avoid triplet-triplet annihilation. Each sample was de-oxygenated by purging with argon gas for at least 30 min. Quartz cells containing 10×10 mm path length were used. The decay of the BODIPYs was monitored between 420-440 and 520-550 nm (depending the BODIPY) following the laser excitation. Samples were irradiated with a total of 6 laser shots to acquire the temporal evolution of ΔOD.

Electrochemical Studies

Electrochemical measurements were performed using a three-electrode system. The working electrode was a Pt wire, a Pt mesh wire was used as the counter electrode, and a Ag/AgCl electrode was used as the reference. A 0.1 M solution of tetrabutylammonium hexafluorophosphate in dry acetonitrile was used as the electrolyte solvent in which the compounds were dissolved to 1 mM or to saturation when the latter occurred before reaching a 1 mM concentration. Concentration was determined from their absorption and calculated extinction coefficient. Solutions also contained ferrocene with a concentration of 1 mM as an internal standard. The solutions were equilibrated with argon, and all measurements were conducted under inert atmosphere, with a minimum scan rate of 0.2 V s$^{-1}$. When the acquired cyclic voltammograms were not reversible the scan rate was increased up to 1 V s$^{-1}$. Formal redox potentials were calculated from the midpoint of the cathodic and anodic peak potentials observed in the cyclic voltammograms. All values were reported vs ferrocene, with the oxidation of ferrocene measured and corrected to zero for all experiments.

Phosphorescence Studies of Compounds 3-6

Phosphorescence from compounds 3-6 was observed cooling a 4:1 EtOH:MeOH solution to 77 K with liquid nitrogen. Dilute sample solutions (Abs<0.1) were prepared in NMR tubes and suspended in a coldfinger Dewar (custom-made by Ace Glass) filled with liquid nitrogen.

Determination of $^1$O$_2$ Quantum Yield ($^1$O$_2$ Phosphorescence, Direct Method)

The generation of singlet oxygen and its lifetime were determined from $^1$O$_2$ phosphorescence decay curves recorded at 1270 nm upon excitation with a 532 nm Nd:YAG laser. A total of 3 laser shots were applied to acquire a trace. Compounds 3-10 were dissolved in air equilibrated acetonitrile solution. Quantum yield of $^1$O$_2$ production ($\varphi_A^D$) were calculated comparing the intensity of $^1$O$_2$ phosphorescence at 1270 nm for the corresponding photosensitizer with that recorded for Rose Bengal ($\varphi_\Delta=0.54$).[81]

Determination of $^1O_2$ Quantum Yield (Photooxidation of DMA, Indirect Method)

Solutions of 9,10-dimethylanthracene (DMA, 50 µM) and photosensitizers (compound 3-10) in air equilibrated acetonitrile were irradiated in 10 mm path length quartz cell (3 ml) with a Nd:Yag laser exciting at 532 nm. Laser excitation was performed at 10 Hz, providing one laser output for every discharge of the flashlamp. An irradiation time of 1 s is equivalent to 10 laser pulses. The energy of each pulse was 10 mJ. The kinetics of DMA photooxidation were studied by following the decrease of the absorbance at $\lambda=377$ nm. The observed rate constant ($k_{obs}$) was obtained by a linear least-squares fit of the semilogarithmic plot of ln [DMA]$_0$/[DMA] (see FIG. 14). Quantum yields of $^1O_2$ production ($\varphi_\Delta^I$) were calculated comparing the $k_{obs}=k_q$ [$^1O_2$] for the corresponding photosensitizer with that for Rose Bengal, which was used as a reference ($\varphi_\Delta=0.54$).[1] Measurements of the sample and the reference under the same conditions afforded $\varphi_\Delta^I$ for compounds (3-10) by direct comparison of the slope in the linear region of the plots.

Figure 15:
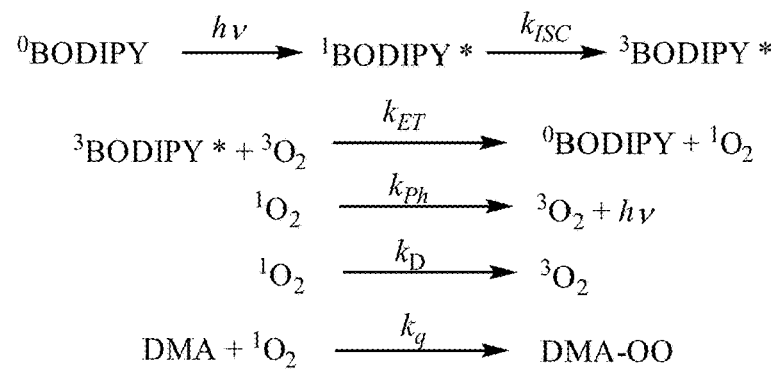
FIG. 15 shows the photosensitized oxidation of DMA in presence of the different BODIPYs.

FIG. 15 shows the mechanism of $^1O_2$ generation after a laser pulse and the $^1O_2$ deactivation by either a chemical reaction with DMA, phosphorescence, or a non-radiative decay pathway. In FIG. 15, $k_{ET}$ is the rate constant for the quenching of excited BODIPY by $^3O_2$ to produce $^1O_2$, $k_{Ph}$ is the rate constant of phosphorescence, $k_D$ is the rate constant for the non-radiative decay of $^1O_2$ and $k_q$ is the rate constant of chemical quenching of $^1O_2$ in presence of DMA.

For the indirect detection of $^1O_2$, it is possible to determine the $k_q$ value considering that the production of $^1O_2$ is constant compare with the initial concentration of DMA. According to these, a pseudo first-order kinetic for this reaction is proposed (equations 2 to 5):

$$-\frac{d[DMA]}{dt} = k_q \times [DMA] \times [^1O_2] = k_{obs} \times [DMA] \quad \text{(Equation 2)}$$

$$k_{obs} = k_q \times [^1O_2] \quad \text{(Equation 3)}$$

$$[DMA]_t = [DMA]_0 \times e^{-k_{obs}t} \quad \text{(Equation 4)}$$

$$\ln\frac{[DMA]_0}{[DMA]_t} = k_{obs} \times t \quad \text{(Equation 5)}$$

Figure 14:
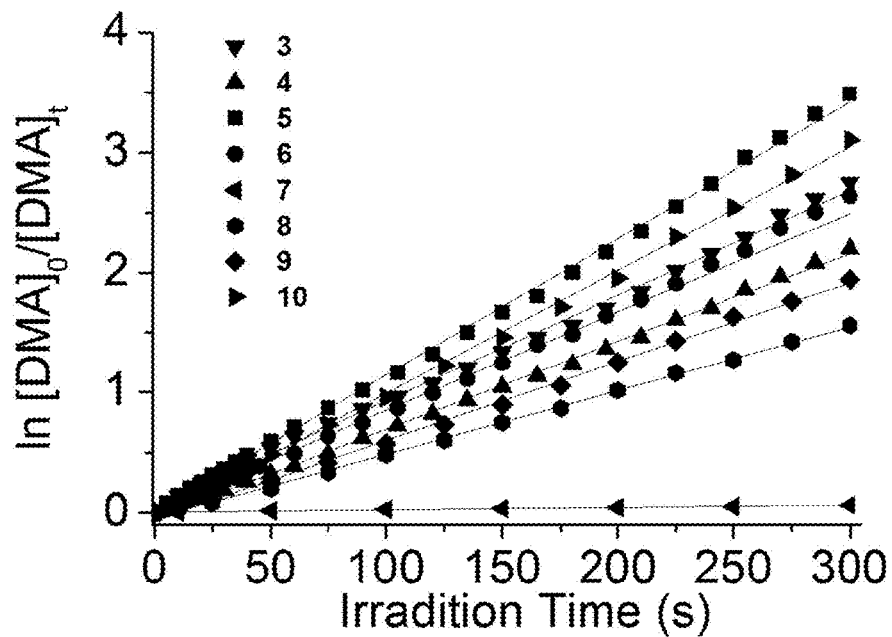
FIG. 14 shows the pseudo first-order kinetic data fitting for compounds 3-10 in air equilibrated acetonitrile.

The conversion of DMA followed pseudo-first order kinetics with the different photosensitizers (see FIG. 14). From equation 5, it was possible to determine $k_{obs}$ and $^1O_2$.

Activation of Compounds 7 and 8 with Dicumyl Peroxide

Compounds 7 and 8 were oxidized/activated in air equilibrated acetonitrile solution upon photolysis of a 100 µM dicumyl peroxide. Irradiation was performed within a fluorimeter to generate ROS upon exciting with ultraviolet light at 263 nm (2.4 mW/cm$^2$). The fluorescence intensity at the emission maxima of the probes was monitored over time. UV irradiation was stopped when the fluorescence intensity enhancement reached its maximum (see FIG. 16, which shows the fluorescence intensity-time profile for compound 7 and 8).

Autocatalytic Activation of Compound 7 (Monitoring $^1O_2$ Phosphorescence)

$^1O_2$ phosphorescence (1270 nm) was monitored with a Hamamatsu NIR detector after different irradiation periods with a Nd:YAG laser operating at 10 Hz. The energy of each laser pulse was 10 mJ exciting at 532 nm. Using the same procedure as described above (Determination of $^1O_2$ Quantum Yield), a total of 3 laser shots were applied to acquire a trace at different time intervals following the continuous irradiation by a second Nd:YAG laser setup. Laser excitation was performed at 10 Hz, providing one laser output for every discharge of the flashlamp. The energy of each laser pulse was 10 mJ. To prepare the samples with PMHC, we first added to the solvent (acetonitrile, air equilibrated) the desired amount of PMHC from a stock solution. Then, compound 7 was dissolved until reaching Abs=0.3 ([7]=5.8 µM). For the samples containing compound 4, we first dissolved 4 in a stock solution of acetonitrile containing 0.12 µM of PMHC and then the desired volume of this solution was added to the solution containing 7 and same concentration of the antioxidant (0.12 µM of PMHC).

Autocatalytic Activation of Compound 7 (Monitoring Fluorescence)

The increase in the fluorescence emission due to autocatalytic activation of compound 7 was followed by continuous irradiation at 532 nm and 1.6 mW/cm$^2$ in air equilibrated acetonitrile using a PTI QuantaMaster spectrofluorimeter. The emission at 557 nm was measured as a function of the irradiation time. Samples were prepared as described above (see Autocatalytic Activation of Compound 7 (Monitoring $^1O_2$ Phosphorescence)).

Biological Assays (Bacterial Strain Conditions)

The microorganism used for this study is E. coli ATCC 25922. Stock cultures were preserved at −70° C. using glycerol 10% (v/v) as the cryoprotectant, and the strain was grown in Luria Bertania broth (LB). Bacterial culture was prepared inoculating a single colony from a pure culture. After overnight incubation at 37° C. for 18 h, the culture reached a density of approximately 1×10$^9$ CFU/mL and it was diluted to 10$^6$ CFU/mL.

Biological Assays (Antibacterial Photodynamic Inactivation Studies in E. coli ATCC 25922)

We carried out PDI in vitro studies with E. coli. Cells (10$^6$ CFU/mL) were incubated with 2-fold diluted solutions of compounds 7 and 9 (activated form of 7) in buffer PBS and LB at a proportion of 70:30% (v/v), to obtain concentrations between 40-0.078 µM. Stock solutions of BODIPY 7 and 9 (400 µM) were prepared in acetonitrile. First, the photodynamic minimal inhibitory concentration (PD-MIC) was determined as the lowest compound concentration at which growth was completely inhibited after overnight incubation of the plate at 37° C. PD-MIC was 40 µM for compounds 7 and 9 in dark conditions. Under light irradiation the PD-MIC was 40 µM and 10 µM for 7 and 9 respectively.

In order to evaluate the minimal bactericidal concentration (PD-MBC, (defined as the lowest concentration leading to death of 99.9% of the initial inoculum), we assayed two conditions, one involving regular E. coli and the other involving E. coli incubated for 2 hours with 500 nM hydrogen peroxide at 37° C. to elicit stress in bacteria. Strain suspensions (10$^6$ CFU/mL) were treated with compounds 7 and 9 for 1 hour under irradiated and non-irradiated conditions. PD-MIC was 10 µM for 7 activated in the stressed bacterial suspension and 9 pre-activated with dicumyl peroxide. Controls of both strains for each condition were run in parallel.

At the end of the irradiation time, 100 µL aliquots were placed in 96 wells from each tube and serially diluted 10-fold in PBS to obtain dilutions of 10$^1$ to 10$^4$ fold, in addition to the original concentration, on agar plates to determine CFU. Viability counts were performed at 0 and 1 hour in either dark or light conditions from each dilution, 10 µL aliquots were plated on LB agar. Plates were streaked in triplicate and incubated for 18 h at 37° C. Each experiment was performed at least three times on different days.

Results and Discussion

Design and Preparation of an Activatable Photosensitizer.

Figure 17:
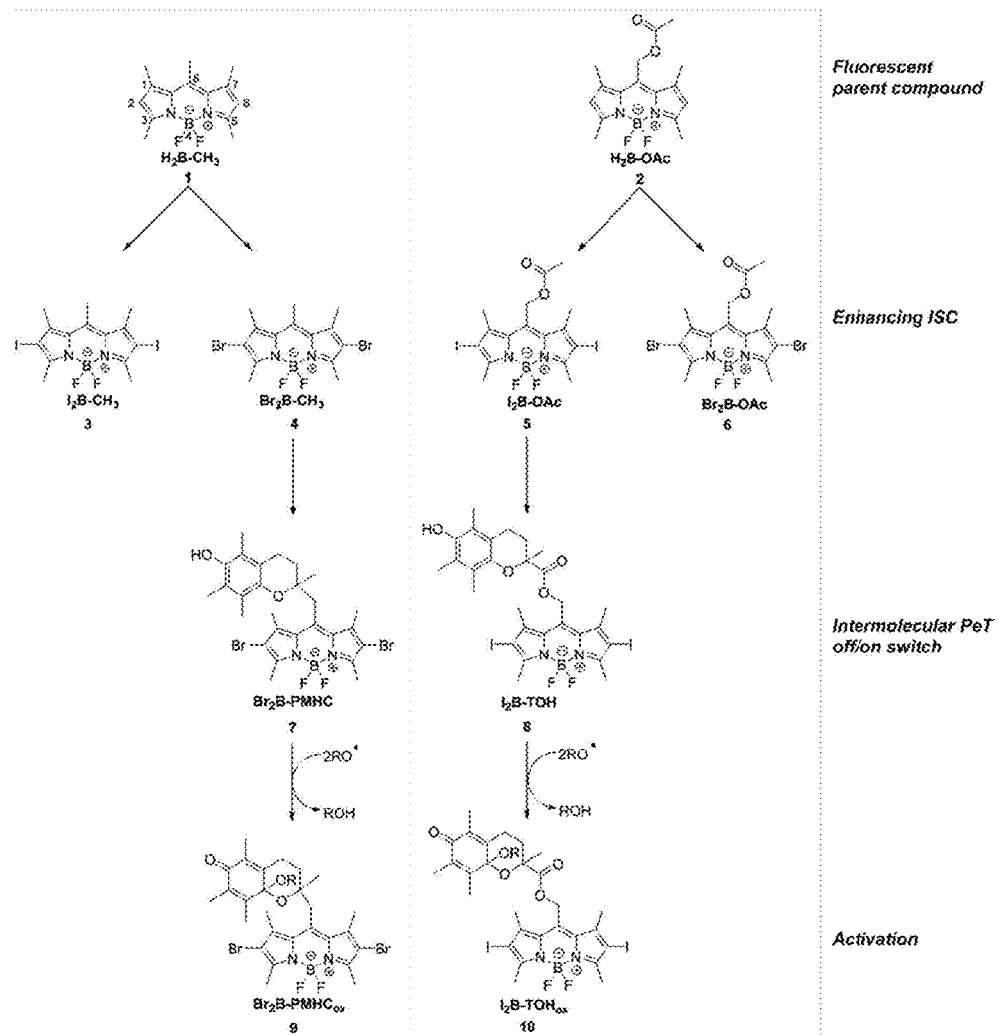
FIG. 17 shows the compounds prepared and studied in Example 1. Compounds 1 and 2 are fluorescent controls for compounds 3-4 and 5-6, respectively. Compounds 3-4 and 5-6 are photosensitizer controls for compounds 7 and 8, respectively.

We selected BODIPY dyes bearing heavy atoms such as I or Br at positions C2 and C6 for the photosensitizing segment (see FIG. 17).

As seen from our results, BODIPY dyes are lipophilic ensuring the partition of the new compound within the lipid membrane. This partition enables rapid reaction of $^1O_2$ with unsaturated lipids, a target in PDT. BODIPY dyes additionally have desirable spectroscopic properties including large extinction coefficients and small internal conversion decay rate constants, minimizing wasteful decay pathways. BODIPY dyes are further relatively robust and inert towards $^1O_2$. These dyes are easy to prepare and functionalize, enabling the substitution with halogens at positions C2 and C6 either before or after coupling the chromophore segment to the trap segment. Decoration with either I or Br substituents ensured rapid ISC to the triplet manifold following photoexcitation of the chromophore. Energy transfer from the BODIPY triplet excited state may then sensitize $^1O_2$. Intramolecular PeT may then be implemented as a molecular switch to turn off/on a desired photophysical or photochemical outcome, e.g. emission in fluorogenic probes or $^1O_2$ sensitization, as shown in this work.

We selected the chromanol moiety of α-tocopherol as the trap segment for the ROS activatable photosensitizer compound.

As seen from our results, the rapid PeT from the chromanol segment to the excited singlet or triplet manifold of either a 2,6 dibromo or a 2,6 diiodo BODIPY photosensitizer segment inactivates the sensitizing properties of the latter. Secondly, the electron rich chromanol ring is additionally an efficient $^1O_2$ quencher operating through both physical (93%) and chemical (7%) pathways. The chromanol thus acts as a molecular switch suppressing $^1O_2$ production at three different levels. Finally, oxidation of the chromanol following reaction with ROS activates the photosensitizer as both PeT and $^1O_2$ scavenging processes are terminated (FIG. 1). Of note, our choice of chromanol coupled to a hydrophobic BODIPY dye ensured high specificity towards photosensitizer activation by lipid peroxyl radicals, the dominant ROS species encountered in lipid membranes under oxidative stress.

We considered two different short linkers to connect the trap and photosensitizer segments. One linker was based on a methylene linker connecting the chromanol and BODIPY moieties. An alternative strategy rested on an ester coupling, providing for a relatively simple synthetic route albeit in detriment of antioxidant activity as a result of the electron withdrawing effect on the chromanol trap of the carbonyl moiety. Altogether two compounds (7 and 8) were conceived bearing either Br or I at positions C2 and C6, respectively, and a linker based on a methylene (7) vs an ester (8) moiety (FIG. 17).

Fluorescent control BODIPY dyes bearing either an ester or a methylene moiety and no halogen (1 and 2, FIG. 17) and BODIPY dyes undergoing ISC but no PeT (controls bearing two Br or two I substitutions with either a methylene or an ester moiety yet lacking the chromanol segment) were also prepared and studied (compounds 3-6, FIG. 17).

H$_2$B—CH$_3$ (compound 1) and H$_2$B—OAc (compound 2) were synthesized from the condensation of 2,4-dimethylpyrrole with acetyl or acetoxyacetyl chloride. Halogenation of 1 and 2 via electrophilic aromatic substitution was used to introduce either I or Br specifically at positions C2 and C6 of the BODIPY. These positions are most susceptible to electrophilic attack given the electronic density of the BODIPY core. We modified literature procedures (Yogo, T.; Urano, Y.; Ishitsuka, Y.; Maniwa, F.; Nagano, T. *J. Am. Chem. Soc.* 2005, 127, 12162, incorporated herein by reference) to introduce I, obtaining I$_2$B—CH$_3$ (compound 3) and I$_2$B—OAc (compound 5) in 72% and 79% yield, respectively, upon reaction of their respective precursors 1 and 2 with I$_2$ and HIO$_3$. Br$_2$B—CH$_3$ (compound 4) and Br$_2$B—OAc (compound 6) where obtained in 84% and 82% yield, respectively, upon direct halogenation of 1 or 2 using a slow addition of Br$_2$. Br$_2$B-PMHC (compound 7) was obtained in 15% yield from the carefully controlled addition of Br$_2$ to our previously prepared H$_2$B-PMHC. I$_2$B-TOH (compound 8) was obtained by coupling trolox to the halogenated BODIPY alcohol via a Mitsunobu reaction yielding the desired compound in 60% yield (since the newly formed compound 5 did not undergo hydrolysis under standard conditions, we hydrolyzed 2 and next halogenated the resulting alcohol following the procedure described above).

Photophysical Studies

In order to evaluate the rate of ISC, we initially compared the fluorescence parameters recorded for compounds 3-4 and 5-6, bearing Br and I atoms, with those recorded for their unsubstituted fluorescent analogues 1 and 2, respectively.

Table 1 lists the emission quantum yields ($\varphi_f$) and the fluorescence decay rate constants (k$_{dec}$) recorded for compounds 1-8. A 27-fold drop in $\varphi_f$ was recorded following inclusion of I atoms in compound 1 (compare values for 1 and 3). A ca. 44-fold drop was recorded when comparing 2 and its I-substituted analogue 5. When BODIPYs were substituted with Br rather than I, smaller drops in $\varphi_f$, ~4-fold, were recorded in going from 1 to 4 and ~6-fold in going from 2 to 6. The drop in $\varphi_f$ and concomitant increase in k$_{dec}$ can be attributed to the heavy atom effect that facilitates ISC processes. The drop underscores the potential of these halogenated BODIPYs to be used as photosensitizer segments. Also listed in Table 1 are the values for the radiative rate constant estimated (k$_{rad}$=$\varphi_f$×k$_{dec}$) for compounds 1-8. The values are consistent with those expected for the BODIPY core, in the range of 10×10$^7$ s$^{-1}$. Values for the decay rate constant associated to non-radiative processes were also estimated (k$_{nr}$=(1−$\varphi_f$)×k$_{dec}$) and are likewise listed in Table 1. We recorded a 1 and 2 order of magnitude increase in k$_{nr}$ upon substituting the parent BODIPY compound with Br and I, respectively (compare compound 1 with 3 and 4; and compound 2 with 5 and 6). The increase in k$_{nr}$ in going from 1-2 to 3-6 may be safely assigned to the addition of a new decay pathway relying on ISC. Given the negligible contribution of k$_{nr}$ to the decay of 1 and 2, one may then assign the measured values of k$_{nr}$ for compounds 3-6 to k$_{ISC}$. ISC is significantly more pronounced for iodo-bearing BODIPY dyes than for their brominated counterparts, resulting in k$_{ISC}$ being one order of magnitude larger for the former than for the later (iodo vs bromo).

Figure 18:
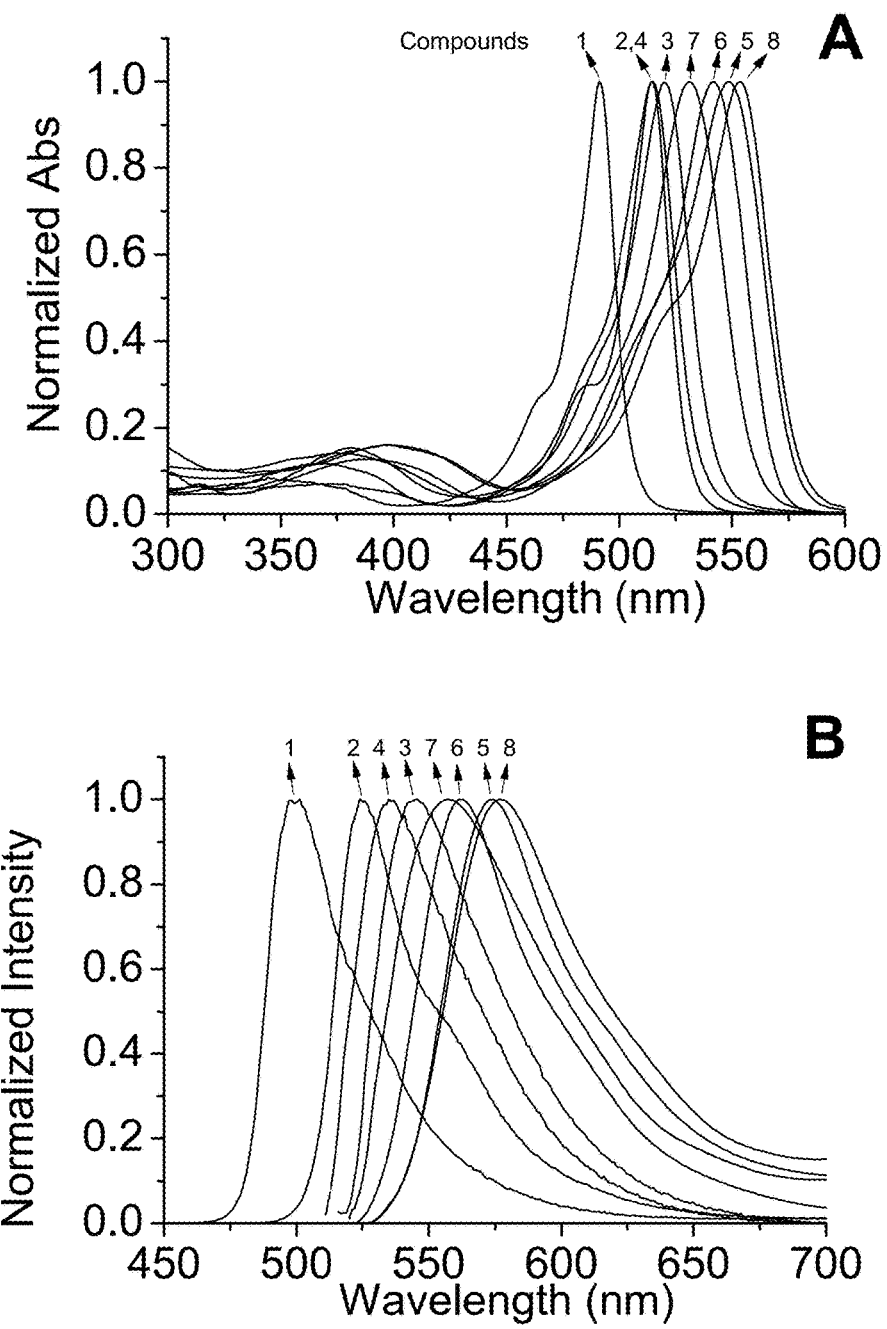
FIG. 18 shows A) normalized absorption spectra and B) normalized fluorescence emission spectra of compounds 1-8 in acetonitrile. Fluorescence spectra were obtained exciting each compound at the first vibronic shoulder of the $S_0$-$S_1$ transition.

Table 1 further lists the absorption and emission maxima and extinction coefficients for the new compounds (see also FIG. 18). All of the dyes showed strong absorption bands between 490-555 nm. Consistent with the stabilizing effect that electron withdrawing groups in the meso position have on BODIPY in its first excited singlet state, a red shift in absorption and emission is observed in going from a methylene moiety to an acetate moiety (compare e.g. 1 vs 2, 3 vs 5, or 4 vs 6) at the meso position. I- or Br-substitution also resulted in a bathochromic shift in the absorbance and emission spectra, indicating that the resonance donating effect of I and Br at positions C2 and C6 of the BODIPY core dominate over the inductive effect, where the effect is more pronounced for I than Br (compare 1 with 3 and 4, and 2 with 5 and 6).

TABLE 1

Photophysical Properties of Compounds 1-8 in Acetonitrile at Room Temperature

| | $k_{dec} \times 10^7$ (s$^{-1}$) | $k_{rad} \times 10^7$ (s$^{-1}$) | $k_{nr} \times 10^7$ (s$^{-1}$) | $\varepsilon \times 10^3$ (M$^{-1}$cm$^{-1}$) | $\Phi_f$ | abs $\lambda_{max}$ (nm) | em $\lambda_{max}$ (nm) |
|---|---|---|---|---|---|---|---|
| [a]1 | 17.8 ± 0.1 | 14.4 ± 0.1 | 3.3 ± 0.1 | 97 | 0.81 ± 0.02 | 491 | 498 |
| [a]2 | 15.0 ± 0.2 | 13.1 ± 0.2 | 2.0 ± 0.1 | 81 | 0.87 ± 0.02 | 515 | 530 |
| 3 | 476.2 ± 0.7 | 13.1 ± 0.2 | 463.0 ± 0.7 | 83 | 0.03 ± 0.01 | 521 | 545 |
| 4 | 55.3 ± 0.2 | 11.0 ± 0.2 | 44.2 ± 0.2 | 79 | 0.20 ± 0.02 | 515 | 535 |
| 5 | 625.0 ± 0.7 | 12.5 ± 0.2 | 582.0 ± 0.7 | 96 | 0.02 ± 0.01 | 550 | 572 |
| 6 | 66.7 ± 0.3 | 9.3 ± 0.1 | 57.4 ± 0.2 | 81 | 0.14 ± 0.02 | 543 | 562 |
| 7 | N.A. | N.A. | N.A. | 56 | ≤0.008 ± 0.002 | 532 | 557.4 |
| 8 | 555.6 ± 0.6 | 5.0 ± 0.1 | 551.0 ± 0.5 | 63 | 0.009 ± 0.002 | 552 | 576 |

[a]Values obtained from reference[31]. Errors reported represent standard deviation of three separate experiments.

Figure 19:
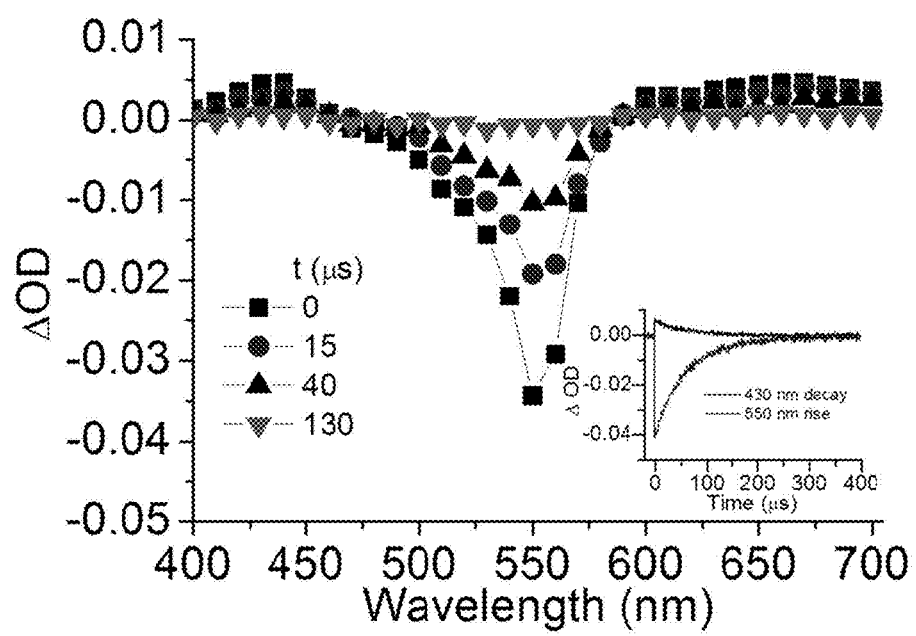
FIG. 19 shows the transient absorption spectra of compound 5 in Ar saturated acetonitrile upon 532 nm laser excitation. The inset shows the time profile for ΔOD recorded at 430 nm (top) and 550 nm (bottom).
Figure 20:
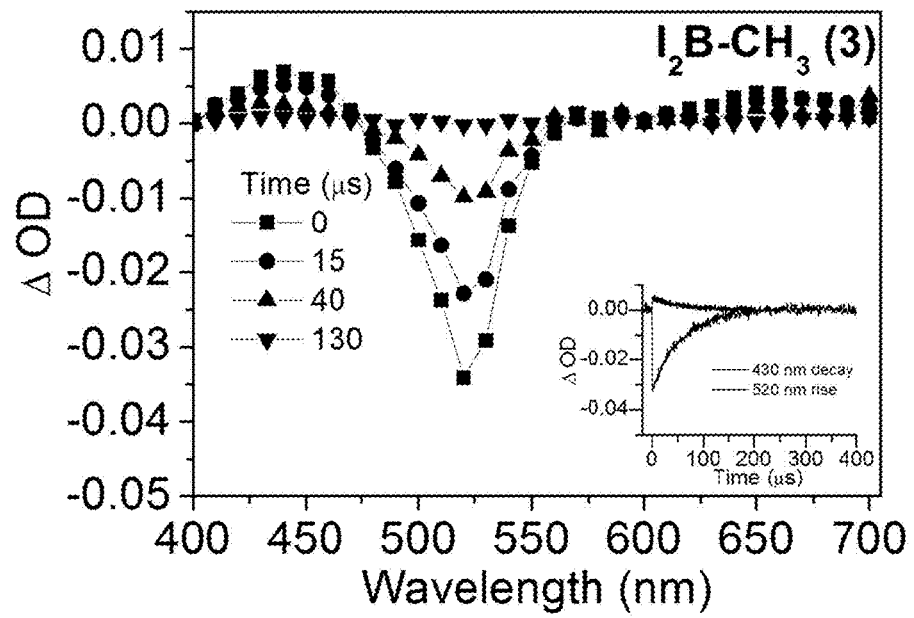
FIG. 20 shows the transient absorption spectra of compounds 3-8 (in A) to F), respectively) in Ar saturated acetonitrile upon 532 nm laser excitation. The inset shows the time profile for ΔOD recorded at 430 nm (top) and 520, or 530, or 550 nm (bottom).
Figure 20:
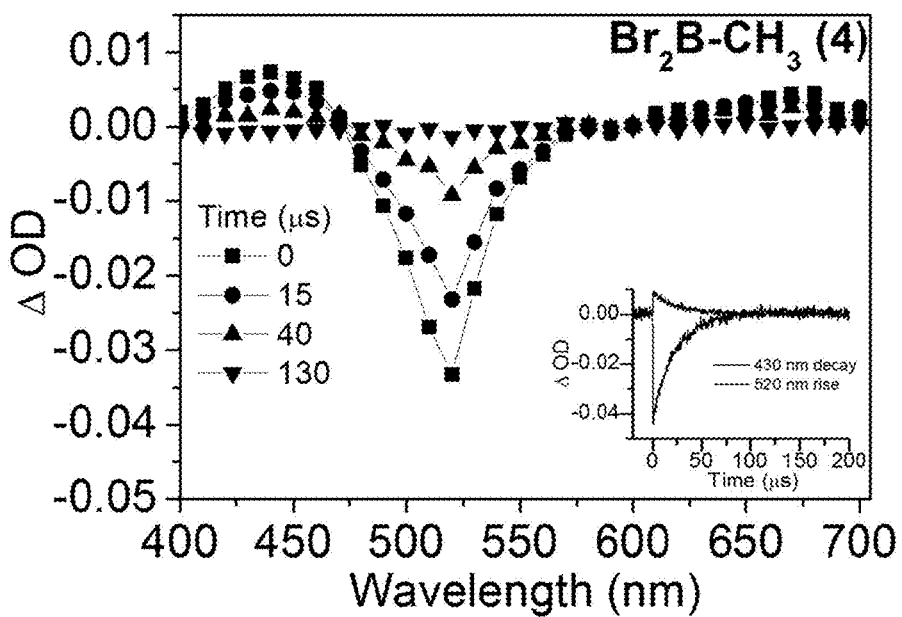
Figure 20:
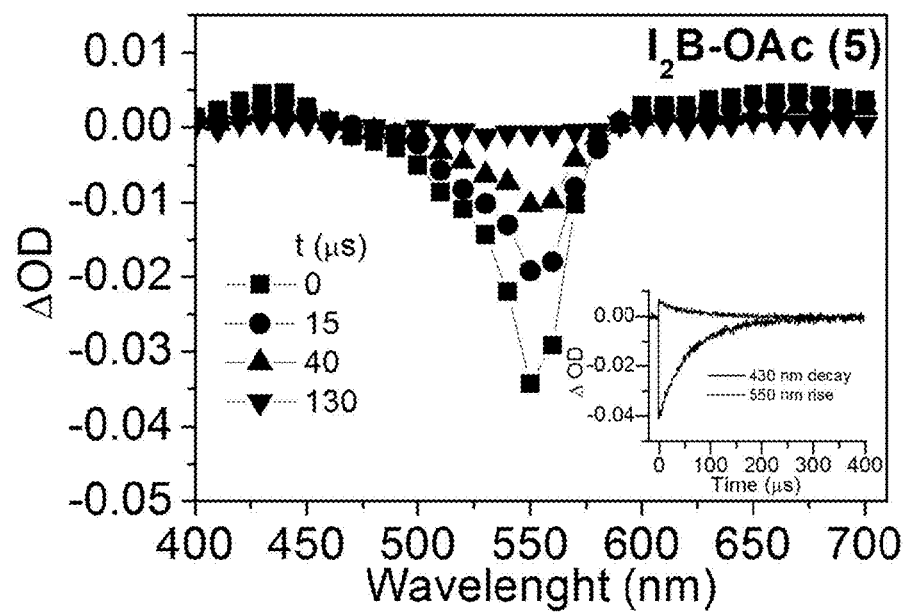
Figure 20:
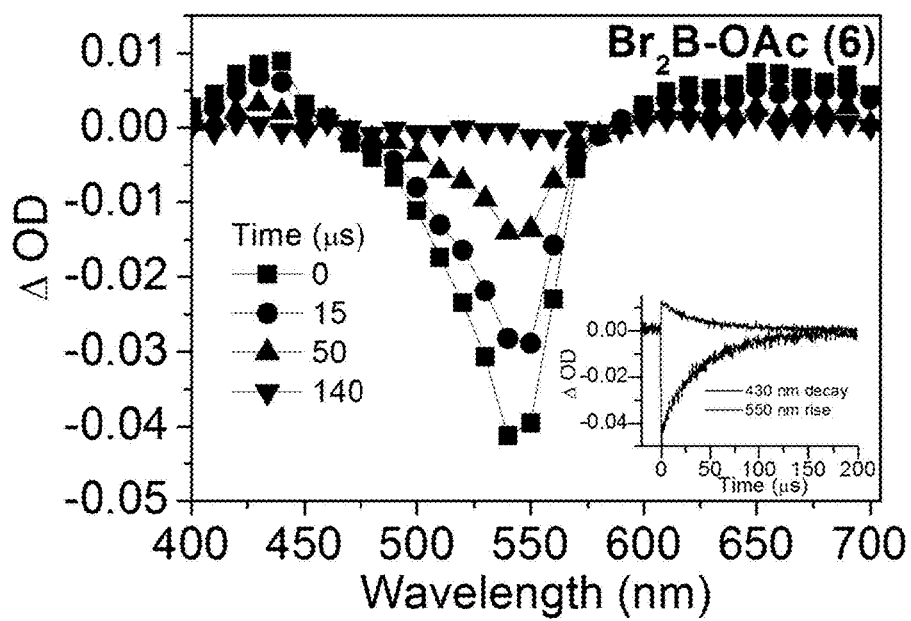
Figure 20:
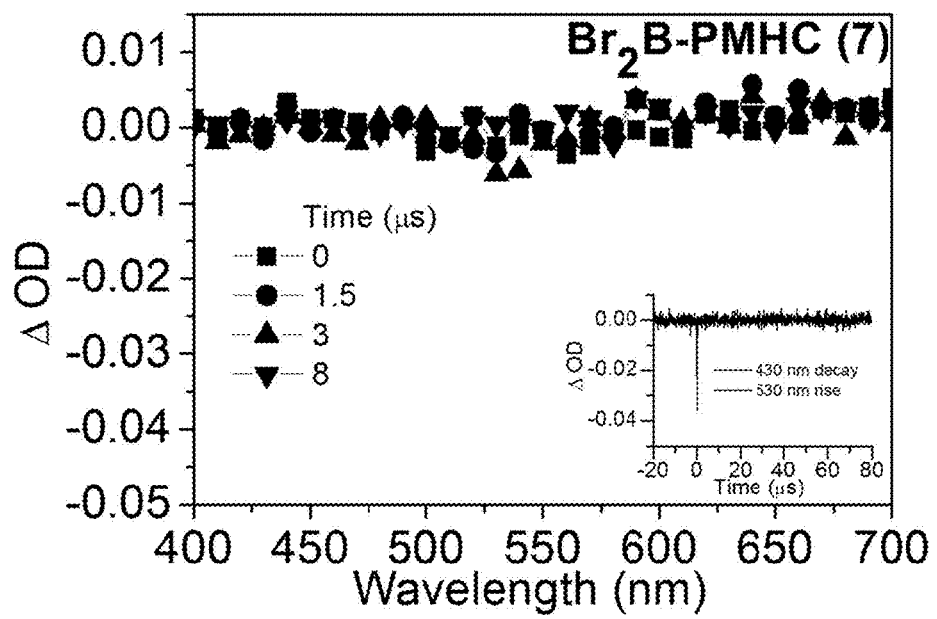
Figure 20:
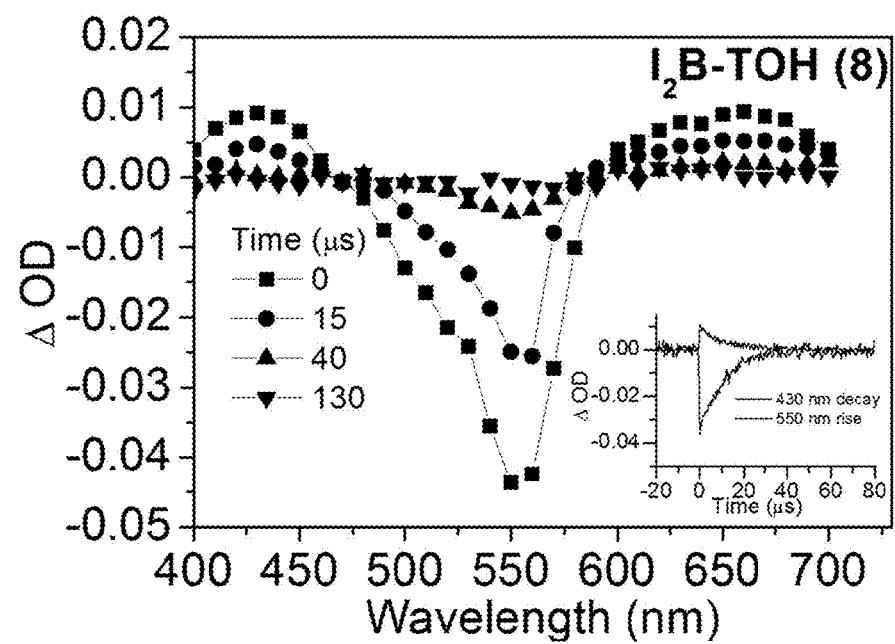

Consistent with intersystem crossing taking place in compounds 3-6, nanosecond laser flash photolysis (LFP) studies on these compounds showed the appearance of a long lived transient species that was not detected with either control compounds 1 and 2 (see FIG. 19 and also FIG. 20 A) to F), which shows the transient absorption spectra of compounds 3-8). The transient spectra were assigned to the triplet-triplet (T-T) absorption of compounds 3-6.[68-70] Two peaks were observed in the regions between 420-440 and 600-700 nm. A negative band was also observed in the range from 460-570 nm, corresponding to the depletion of ground state BODIPY. Triplet decay rate constant $k_T$ values of $1.7 \times 10^4$ s$^{-1}$ and $2.7 \times 10^4$ s$^{-1}$ were recorded for the iodo substituted BODIPYs (compounds 3 and 5) and their bromo-substituted analogues (4 and 6), respectively, upon monitoring the T-T absorption time profile at either 430 nm or 550 nm in argon saturated solutions (see also Table 2). Consistent with the triplet assignment, the transients were readily quenched by molecular oxygen with quenching rate constant ($k_q$) values in the range of $2-3 \times 10^9$ M$^{-1}$s$^{-1}$, one order of magnitude smaller than the diffusion controlled rate constant in acetonitrile (Table 2).

TABLE 2

Triplet excited state properties and singlet oxygen quantum yields for compounds 3-10 in acetonitrile

| | $k_T \times 10^4$ (s$^{-1}$) Argon Purged | $k_T \times 10^6$ (s$^{-1}$) Air equilibrated | [a]$k_q \times 10^9$ (M$^{-1}$s$^{-1}$) Q = $^3O_2$ | $k_q \times 10^8$ (M$^{-1}$s$^{-1}$) Q = PMHC | [b]$\Phi_\Delta^I$ | [c]$\Phi_\Delta^D$ |
|---|---|---|---|---|---|---|
| 3 | 1.68 ± 0.02 | 4.35 ± 0.02 | 1.82 ± 0.03 | 1.20 ± 0.05 | 0.75 ± 0.04 | 0.81 ± 0.02 |
| 4 | 2.70 ± 0.02 | 4.55 ± 0.03 | 1.91 ± 0.02 | 1.29 ± 0.04 | 0.64 ± 0.03 | 0.72 ± 0.02 |
| 5 | 1.64 ± 0.02 | 7.14 ± 0.04 | 3.01 ± 0.01 | 3.95 ± 0.07 | 0.95 ± 0.03 | 0.98 ± 0.03 |
| 6 | 2.72 ± 0.03 | 6.67 ± 0.04 | 2.80 ± 0.02 | 2.23 ± 0.05 | 0.79 ± 0.02 | 0.84 ± 0.02 |
| 7 | N.A. | N.A. | N.A. | N.A. | N.A. | N.A. |
| 8 | 9.16 ± 0.05 | 4.55 ± 0.02 | 1.88 ± 0.02 | 5.90 ± 0.09 | 0.46 ± 0.03 | 0.57 ± 0.02 |
| 9 | 3.12 ± 0.02 | N.A. | N.A. | N.A. | 0.57 ± 0.03 | 0.68 ± 0.02 |
| 10 | 1.58 ± 0.02 | N.A. | N.A. | N.A. | 0.87 ± 0.02 | 0.92 ± 0.03 |

[a]Values calculated considering that the solubility of oxygen in acetonitrile is 2.42 mM according to reference [72].

[b]Singlet oxygen quantum yields calculated from the consumption of dimethylantracene using Rose Bengal as a standard, $\Phi_\Delta$(RB) = 0.54,[73] $k_{obs}^{DMA}$ = 6.3 × 10$^{-3}$ (s$^{-1}$).

[c]Singlet oxygen quantum yield determined directly from phosphorescence studies. Data were represented as the mean ± standard deviation of each group.

Control Layer for $^1O_2$ Production.

We subsequently tested via steady-state and time-resolved emission and LFP studies the extent to which the trap segment deactivates the production of $^1O_2$.

A first layer of control at the level of the singlet excited state was confirmed by the significant intramolecular quenching of fluorescence by the trap segment (Table 1).

Thus for compound 7 (methylene linker), we recorded a ca. 25-fold drop in $\varphi_f$ compared to the reference compound 4. A ca. 2-fold drop in $\varphi_f$ was recorded for 8 when compared to 5. The larger fluorescence sensitivity to insertion of the chromanol moiety recorded for 7 vs 8 arises from the slower rate of ISC and the faster rate of competing PeT for 7 (Br-BODIPY bearing a methylene linker) vs 8 (see also Table 1 for ISC and Table 3 and text below for PeT). Essentially, $k_{dec}$ for the control compound 5 is an order of magnitude larger than for control 4, and a new deactivation pathway (PeT in 8) results in little changes to $\varphi_f$ in going from 5 to 8. Ultimately, the intramolecular switch introduced by the trap segment offers a better control/prevention of $^1O_2$ sensitization in 7 than 8. Importantly, the measured fluorescence decays were too fast for 7 and 8 to obtain a reliable value for $k_{dec}$ in our setup. Based however on the $\varphi_f$ value recorded for 7 $\varphi_f \leq 0.008$, we may safely place the value for the intramolecular electron transfer rate constant from the singlet state ($k_{eT}$) in compound 7 at $k_{eT} \geq 1 \times 10^{10}$ s$^{-1}$.

Figure 21:
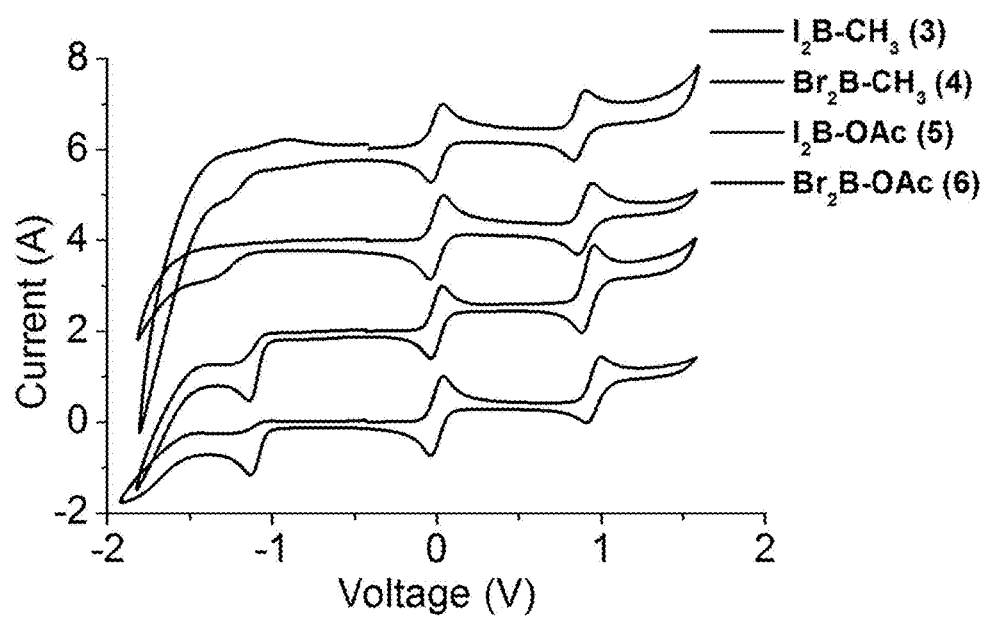
FIG. 21 shows the cyclic voltammogram for 0.68 mM solution of compounds 3-6 (the voltammogram are shown in the same order as the legend). Voltammograms were acquired in degassed, Ar-saturated acetonitrile (0.1 M tetrabutylammonium hexafluorophosphate) versus 0.40 mM Fc/Fc$^+$. The wave at a potential=0 V corresponds to Fc/Fc$^+$.

Consistent with quenching of the singlet via PeT from the chromanol segment, the Gibbs free energy for photoinduced electron transfer ($\Delta G_{eT}^0$) was exergonic for compounds 7 and 8, in the range of 0.4 eV (see Table 3). This parameter was calculated based on equation 6,[8,71] utilizing the first singlet excited state energies and electrochemical redox potentials for compounds 1-6 listed in Table 3 (see FIG. 21, which shows the cyclic voltammograms of Compounds 3-6).

$$\Delta G_{eT}^0 = [e(E_{D^+/D} - E_{A/A^-}^0) + \omega - \Delta E_{00}] \quad \text{(Equation 6)}$$

where e is the elementary charge, $\omega$ is the electrostatic work term that accounts for the effect of Coulombic interaction of the radical ions formed upon reduction/oxidation, $\Delta E_{00}$ is the vibrational zero electronic energy of the excited fluorophore (either singlet or triplet), $E_{A/A^-}^0$ is the one-electron redox potential for the electron acceptor (BODIPY), and $E_{D^+/D}^0$ is the one-electron redox potential for the electron donor (phenol).

Figure 22:
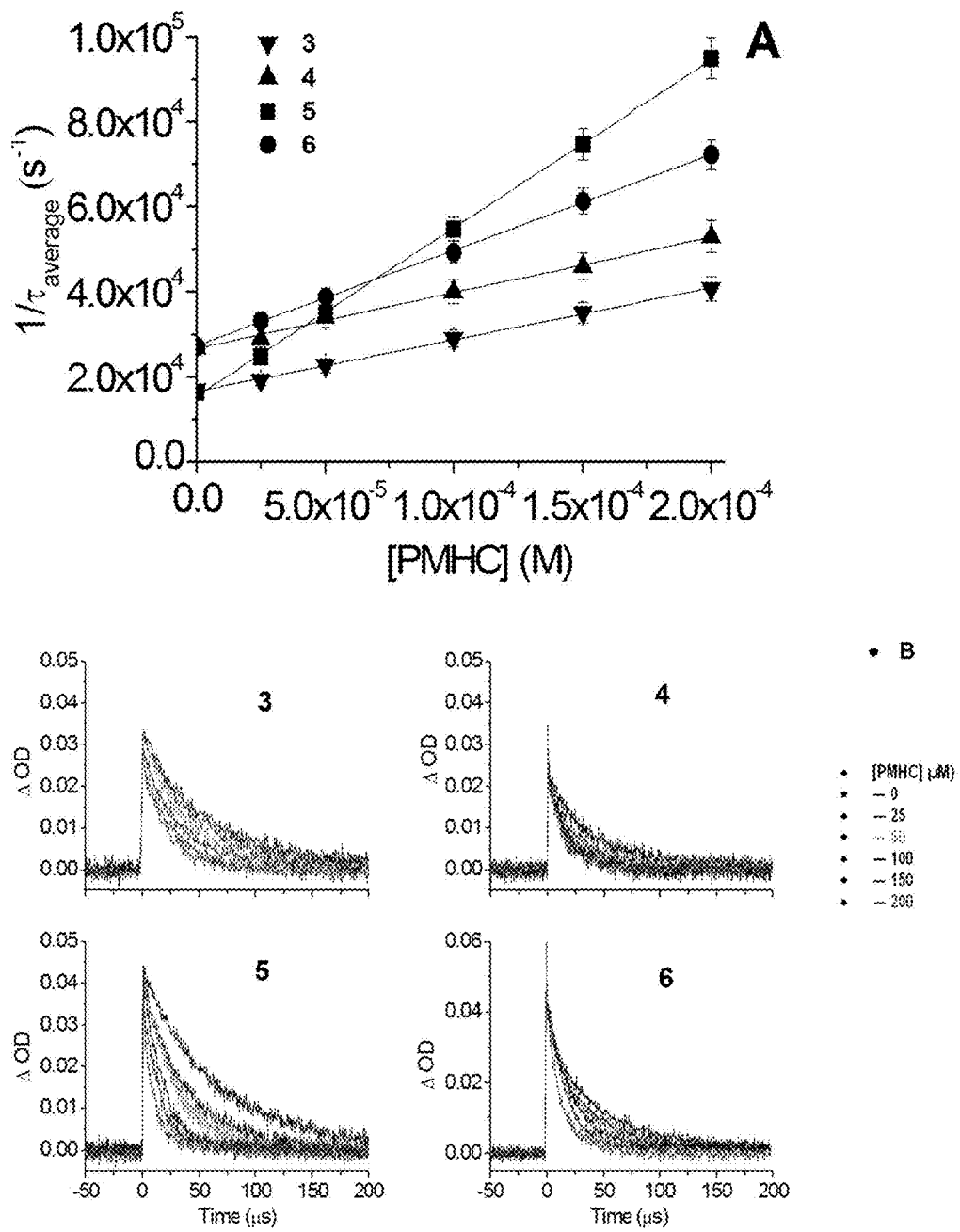
FIG. 22 shows (A) the linear correlation between the experimentally obtained decay rate constants recorded for compounds 3-6 with increasing [PMHC]. Values represent mean±standard deviation of three separate experiments, and (B) the time profile for ΔOD recorded at 520 nm with increasing [PMHC]. Measurements were performed in Ar saturated acetonitrile.

A second layer of control was subsequently tested via LFP studies, to monitor the extent to which the trap segment deactivates the triplet excited state of the photosensitizes. Intermolecular triplet quenching studies were conducted monitoring the decay of the T-T absorbance of compounds 3-6 at 430 nm in the presence of increasing concentrations of either 2,2,5,7,8-pentamethyl-6-hydroxy-chroman (PMHC, see FIGS. 22 A and B), which shows the intermolecular triplet quenching studies of compound 3-6 with PMHC) or 6-Hydroxy-2,5,7,8-tetramethylchromane-2-carboxylic acid (trolox). The two quenchers emulate the trap segments utilized in 7 and 8, respectively. Quenching rate constants $k_q$ values in the order of $1 \times 10^8$ to $4 \times 10^8$ M$^{-1}$s$^{-1}$ were obtained for PMHC and compounds 3-6 (see also Table 2), no quenching was observed however for trolox, a chromanol like PMHC but bearing an electron withdrawing ester group and characterized by having a slightly higher oxidation potential than PMHC.

The intramolecular PeT quenching of the triplet excited state by the trap segment was next evaluated. Upon covalent attachment of the chromanol moiety to the photosensitizers (compounds 7 and 8), a significant increase in the value of $k_T$ was observed. Specifically, a 6-fold increase was observed for 8 compared to its precursor 5 (Table 2) revealing a moderate quenching by an ester linked chromanol segment. In the case of 7, we were unable to detect any triplet-triplet absorption in contrast to its precursor 4, signaling that little triplet was formed as a result of efficient PeT in the singlet excited state, and/or an extremely rapid intramolecular quenching of the triplet excited state from the methylene-linked chromanol trap segment via PeT (vide infra). The intramolecular PeT quenching is much faster for a chromanol lacking the ester moiety, consistent with the intermolecular quenching studies described above. The intramolecular triplet quenching in 7 and 8 thus provided a second layer of control on the photosensitizers activity, at the level of the precursor triplet state.

Figure 23:
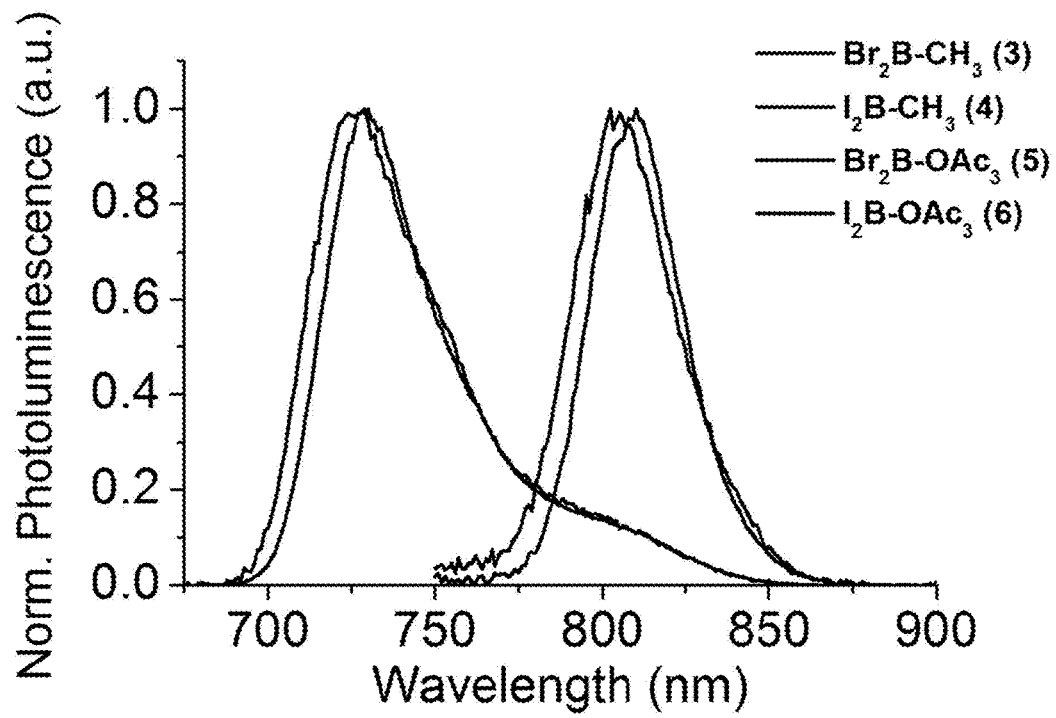
FIG. 23 shows the phosphorescence spectra of compounds 3-6 recorded in 4:1 EtOH:MeOH solution at 77 K (order of the traces from left to right: I$_2$B—CH$_3$ (4), Br$_2$B—CH$_3$ (3), Br$_2$B—OAc$_3$ (5), and I$_2$B—OAc$_3$ (6).

The value of $\Delta G_{eT}^0$ for the first excited triplet state was calculated utilizing equation 6 and the triplet excited state energy obtained from phosphorescence emission of compounds 3-6 (see Table 3 and FIG. 23, which shows the phosphorescence spectra of compounds 3-6). Based on these calculations $\Delta G_{eT}^0$ for PeT from the chromanol to the triplet excited state of 3-6 was endergonic, ca. 0.27 eV, accounting for the small intermolecular rate constant of quenching measured for these compounds in the presence of either PMHC or trolox, and for the long triplet decay rate constant $k_T$ recorded for compound 8. Importantly, the efficiency of PeT also relies in the distance between the trap segment and the photosensitizers a factor that may additionally contribute to the differences observed between compound 7 (methylene linker) and compound 8 (ester linker).

The third layer of control involving geminate quenching of $^1O_2$ by the trap segment was next explored. The chromanol ring in α-tocopherol is an efficient $^1O_2$ quencher where mostly physical (93%) but also chemical (7%) deactivation takes place. The ratio of physical (95%) to chemical (5%) quenching of $^1O_2$ by PMHC is within experimental error the same for α-tocopherol.[34] Both α-tocopherol and PMHC have similar overall singlet oxygen quenching rate constant ($k_q = k_{q(physical)} + k_{q(chemical)}$) with values of $2.06 \times 10^8$ M$^{-1}$ s$^{-1}$ and $1.96 \times 10^8$ M$^{-1}$ s$^{-1}$, respectively (see reference 74). Our experiments showed that the singlet oxygen quenching rate constant by compound 7 has a value of $2 \times 10^8$ M$^{-1}$ s$^{-1}$. The differences between α-tocopherol, PMHC, and our compound rely on their lipophilic tail (phytyl chain, methyl and bodipy respectively, ensuring their partition or lack thereof within the membrane) yet the chromanol moiety, responsible for the chemical reactivity, is preserved intact in all 3 compounds ensuring that within error, their chemical and physical quenching constants of $^1O_2$ are the same. We have previously shown for example that the chemical reactivity of these compounds with peroxyl radicals[29] is the same.

To test whether 7 is equally efficient at deactivating $^1O_2$ as α-tocopherol, we generated $^1O_2$ upon irradiation of compound 5 and monitored the $^1O_2$ phosphorescence lifetime in the presence of increasing amounts of either 7 or PMHC (an α-tocopherol analogue lacking the phytyl tail). We measured similar rate constants (see FIG. 24) for the intermolecular quenching rate constants of $^1O_2$ by 7 and PMHC ($k_q = 2.0 \times 10^8$ M$^{-1}$s$^{-1}$ and $k_q = 4.0 \times 10^8$ M$^{-1}$s$^{-1}$, respectively) indicating that 7 is an efficient $^1O_2$ quencher, on par with α-tocopherol.

TABLE 3

Electrochemical data, HOMO and LUMO orbital energies, singlet excited state and triplet excited state energies, and Gibbs free energies for PeT

| | $^a$E$_{00}$ (eV) | $^b$E (Triplet) | $^c\varepsilon_{LUMO}$ (eV) | $^d\varepsilon_{HOMO}$ (eV) | $^e$E$^o{}_B{}^+$/B | $^f$E$^o{}_{pc}$ | $\Delta G_{eT}$ (Singlet) | $\Delta G_{eT}$ (Triplet) |
|---|---|---|---|---|---|---|---|---|
| 1$^g$ | 2.53 | N.A. | −2.31 ± 0.05 | −5.36 ± 0.01 | 0.77 | N.A. | −0.26 | N.A. |
| 2$^h$ | 2.38 | N.A. | −2.61 ± 0.05 | −5.49 ± 0.01 | 0.75 | −1.44 | −0.24 | N.A. |
| 3 | 2.33 | 1.70 | −2.87 ± 0.05 | −5.81 ± 0.01 | 0.88 | N.A. | −0.37 | 0.262 |
| 4 | 2.37 | 1.71 | −2.94 ± 0.05 | −5.75 ± 0.01 | 0.89 | N.A. | −0.38 | 0.282 |
| 5 | 2.21 | 1.54 | −3.09 ± 0.05 | −5.87 ± 0.01 | 0.91 | −1.14 | −0.4 | 0.269 |
| 6 | 2.25 | 1.53 | −3.15 ± 0.05 | −5.81 ± 0.01 | 0.94 | −1.13 | −0.43 | 0.287 |

$^a$E$_{00}$ = HOMO-LUMO gap obtained from the intercept of the normalized absorption and emission spectra;
$^b$Energy of the lowest triplet state, from phosphorescence emission spectra;
$^c$Energy of the lowest unoccupied molecular orbital derived from Hammett constants and associated errors;
$^d$Energy of the highest occupied molecular orbital derived from Hammett constants and associated errors;
$^e$E$^o{}_B{}^+$/B = reversible oxidation potential;
$^f$E$^o{}_{pc}$ = cathodic peak potential.
$^g$Values obtained from reference [54].
$^h$Values obtained from reference [31].

Figure 25:
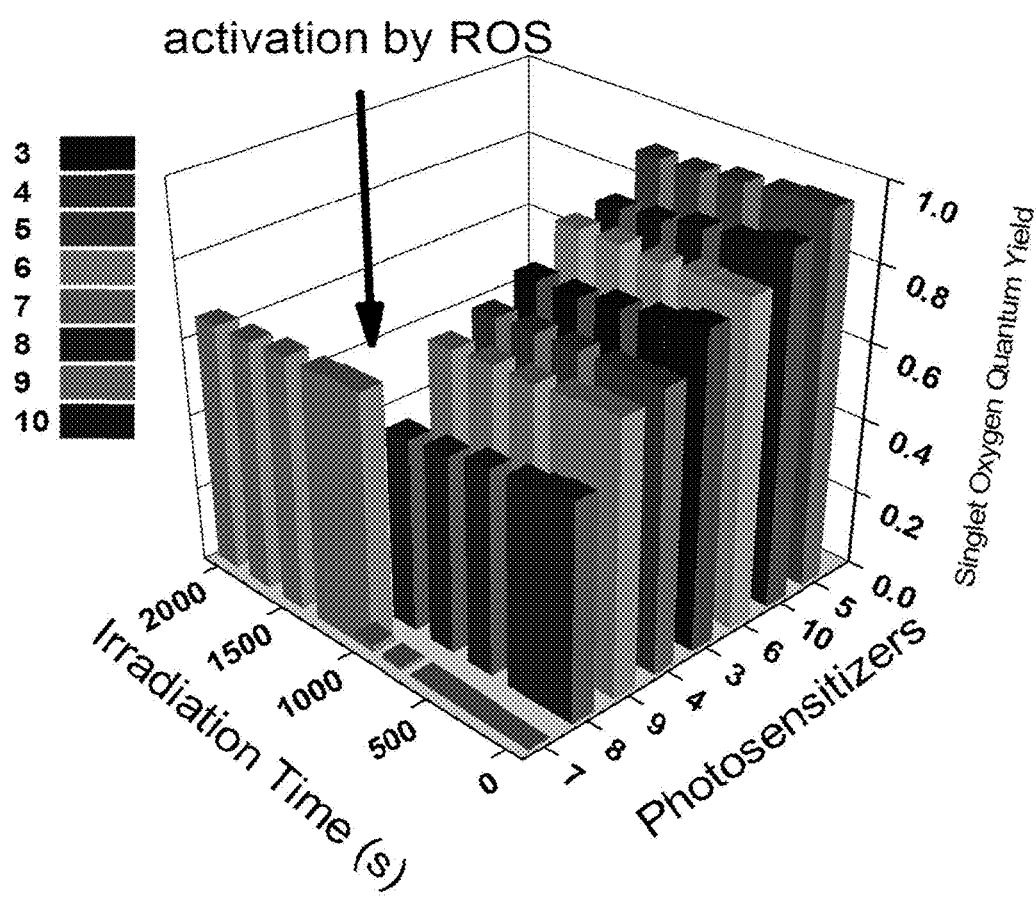
FIG. 25 shows the $^1O_2$ phosphorescence emission intensities ($\lambda_{em}$=1270 nm) as a function of irradiation time for the different photosensitizers in air-equilibrated acetonitrile solutions. Compound 7 was activated following reaction with cumyloxyl radicals. The solution of 7 contained an equimolar amount of sacrificial PMHC to prevent premature oxidation of 7. A pulsed laser operating at a 10 Hz frequency and with a 532 nm output of 10 mJ/pulse was employed to excite the sample.
Figure 26:
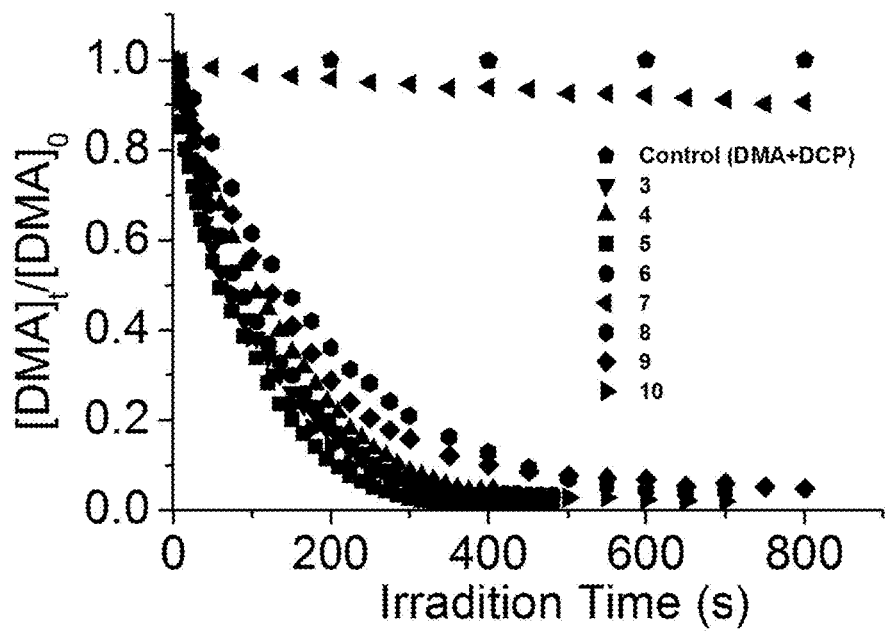
FIG. 26 shows the relative concentration of DMA as a function of the irradiation time for compounds 3-10 in air equilibrated acetonitrile.

In order to quantify the quantum yield of singlet oxygen generation ($\varphi_A$) for the control compounds 3-6, the deactivated compounds 7 and 8, and their activated forms 9 and 10 (vide infra), we measured the phosphorescence of $^1O_2$ at 1270 nm (direct method, FIG. 25). An indirect method based on changes in the absorbance of 9,10-dimethylanthracene upon its oxidation by $^1O_2$ was also applied (see FIG. 14, which shows the pseudo first-order kinetic data fitting for compounds 3-10 (indirect detection of $^1O_2$), and FIG. 26, which shows the relative concentration of DMA as a function of the irradiation time (indirect detection of $^1O_2$)).[76] In both cases, the $\varphi_A$ from Rose Bengal was used as a reference.[73] Similar $\varphi_A$ values were obtained for the compounds under study using either the direct determination or the photooxidation of dimethylanthracene (see Table 2).

Iodo-substituted BODIPYs 3 and 5 showed comparable values of $\varphi_A$ (0.81 and 0.98, respectively) roughly 10% larger than those of their brominated counterparts 4 and 6, respectively. This is consistent with ISC being significantly more pronounced for iodo-bearing BODIPY dyes than for their brominated counterparts. In general, the $\varphi_A$ values for compounds 3-6 also correlate with ISC being the dominant decay pathway in the iodo- or bromo-substituted BODIPYs in comparison to their unsubstituted counterparts 1 and 2. Addition of Br to the BODIPY core is shown to increase the overall singlet excited state decay rate constant $k_{dec}$ in the range 3.1-fold to 4.5-fold (compare 1 vs 4 or 2 vs 6, respectively), i.e., ISC accounts for ⅔ to ⅘ of the overall singlet excited state deactivation. One may thus expect at best a 60%-80% value for $\varphi_A$, consistent with the tabulated values in Table 2. In turn $k_{dec}$ increased ca. 27-fold and 42-fold upon iodo-substitution (compare 1 vs 3 or 2 vs 5, respectively). In this case $\varphi_A$ is expected to be above 95%, as was observed for 5. The slightly smaller $\varphi_A$ recorded for 3 may be the result of $^1O_2$ quenching by the more nucleophilic BODIPY 3 lacking the ester group of 5. In line with this argument, 3 was observed to photodegrade at a slightly larger pace than 5 presumably via photooxidation (see FIG. 25).

We observed no $^1O_2$ generation for freshly prepared solutions of 7. Geminate (static) quenching of $^1O_2$ in compound 8 by the chromanol trap segment was inferred from its $\varphi_A$ value that was ca. ½ that recorded for its control compound 5. This would be consistent with the third control layer of $^1O_2$.

Activation of the Photosensitizer

Figure 16:
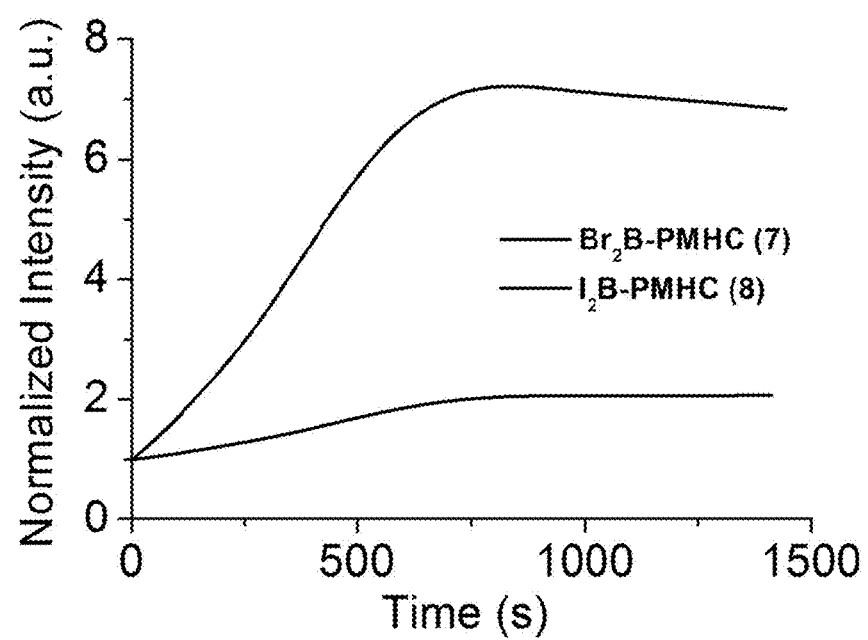
FIG. 16 shows the fluorescence intensity-time profiles for compounds 7 (top trace) and 8 (bottom trace) gradually activated at a constant rate upon photolysis at 263 nm of an air equilibrated 100 μM dicumyl peroxide acetonitrile solution.

Activation of the dormant photosensitizer 7 or 8 (deactivation of PeT) following their reaction with ROS was subsequently tested in the presence of alkoxyl radicals. These ROS were generated at a constant rate upon photolysis at 263 nm of an air equilibrated 100 μM dicumyl peroxide solution in acetonitrile. We followed over time the increase in fluorescence intensity (drop in PeT) to monitor the extent of activation, see FIG. 16. Activation was complete once the intensity reached a plateau.[28,45] At this point, the trap segment in 7 and 8 reacted to completion with alkoxyl radicals to generate 9 and 10, respectively. Consistent with deactivation of PeT in the triplet excited state following ROS scavenging by 7 and 8, values of $k_T$ recorded with the oxidized compounds 9 and 10 were comparable to those obtained for control compounds 3-6 (see Table 2). Deactivation of PeT in the singlet excited state in turn manifested in the ca. 7-fold and 2-fold emission enhancements recorded for 9 vs 7, and 10 vs 8, respectively (FIG. 16).

Figure 24:
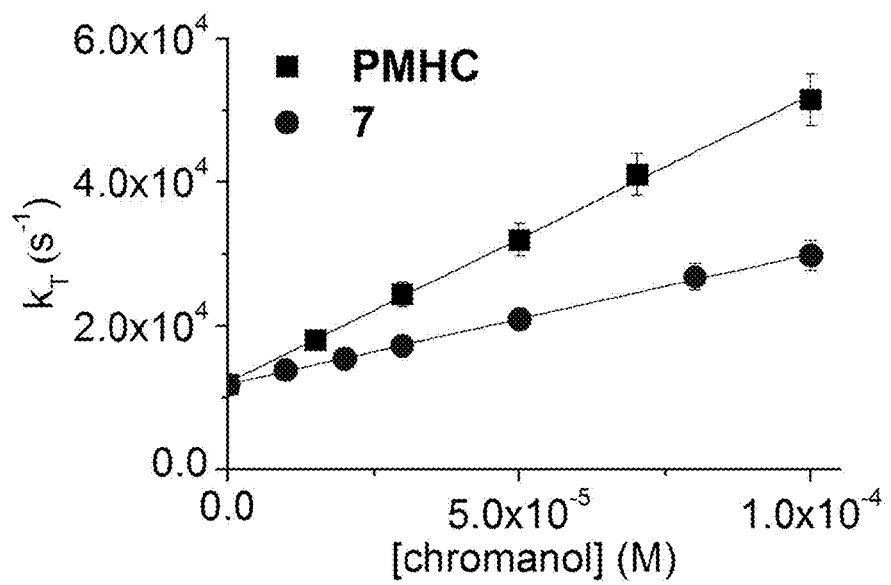
FIG. 24 shows the decay rate constant for $^1O_2$ phosphorescence in the presence of increasing concentration of chromanol rings (either compound 7 or PMHC). $^1O_2$ was generated upon irradiation of compound 5 in air equilibrated acetonitrile solutions. Values represent mean±standard deviation of three separate experiments.

Direct activation of 7 to yield 9 upon reaction with cumyloxyl radicals resulted in a dramatic increase in $^1O_2$ generation. We recorded a ca. 40-fold enhancement in $\varphi_A$ for 9 with respect to 7 (FIG. 24). The $\varphi_A$ recorded for 9 is further comparable to the one achieved for the control compound 4, indicating that the photosensitizing properties of the Br-substituted BODIPY were fully restored. Compounds 10 (activated 8), and 5 had the same $\varphi_A$. Importantly, we recorded a $^1O_2$ phosphorescence decay lifetime of ca. 80 μs upon photosensitization by all compounds but 7 (where $^1O_2$ was not generated) and by 8, where the lifetime dropped to 70 μs, consistent with intermolecular quenching of $^1O_2$ by the chromanol moiety, i.e., $^1O_2$ that was not scavenged by its source was eventually scavenged intermolecularly.

Autocatalytic Activation and $^1O_2$ Amplification.

The juxtaposed antioxidant (chromanol) and prooxidant (Br-BODIPY) antagonistic chemical activities of the two-segment compound paved the way for the autocatalytic activation of $^1O_2$ sensitization (FIG. 1).

Kinetic competition will determine whether the three control layers may or not be avoided following photoexcitation of 7 to yield $^1O_2$. One may set lower bound values for rate constants of electron transfer in the singlet ($k_{eT}$) and triplet ($k'_{eT}$) manifolds relative to competing processes. Assuming then that in the singlet manifold $k_{eT} \sim 25 \times k_{ISC}$ and that in the triplet manifold $k'_{eT} \sim 10 \times k_q[O_2]$, the fraction of photoexcited 7 effectively sensitizing singlet oxygen is <4×10⁻³. Considering next geminate (static) quenching of ¹O₂ by the chromanol trap segment is 100% effective (no escape of ¹O₂) and that 95-97% of quenching is physical, and only 5-3% is chemical quenching, then the fraction of photoexcited 7 undergoing activation through reaction with its own singlet oxygen is smaller than 2×10⁻⁴. However, ¹O₂ may escape the solvent cage upon formation ($k_q$ of singlet oxygen is smaller than diffusion control) so it may activate a second molecule of 7 different to the one that generated it.

Figure 27:
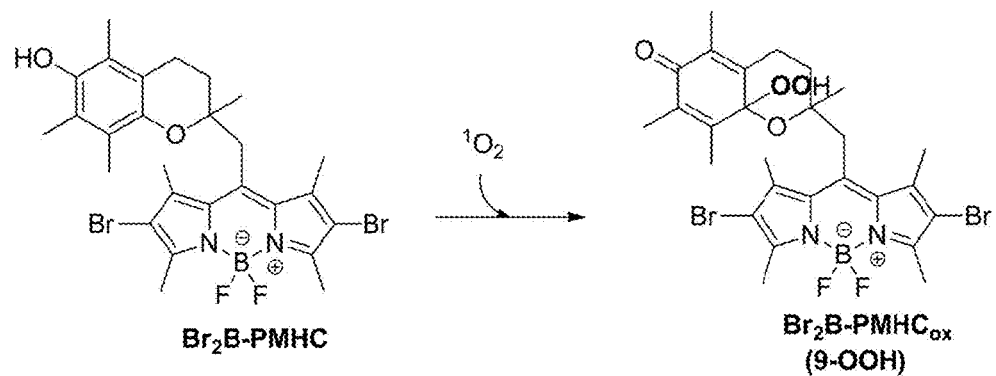
FIG. 27 shows the proposed reaction of 7 with $^1O_2$.
Figure 28:
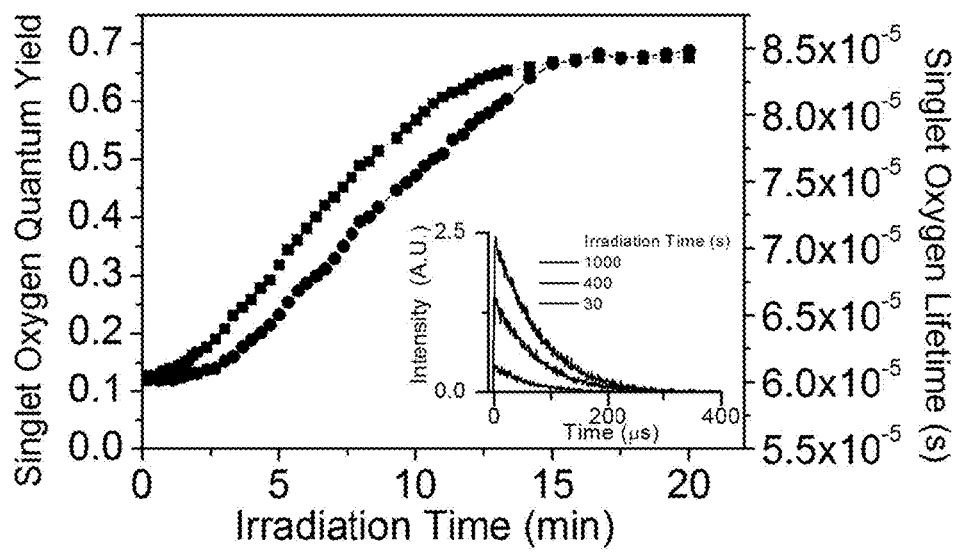
FIG. 28 shows the singlet oxygen quantum yield (■) and singlet oxygen lifetime (●) for compound 7 as a function of the irradiation time. The inset shows $^1O_2$ phosphorescence decay traces recorded at 1270 nm following increasing irradiation times (1000 s top, 400 s middle, 30 s bottom). [7]=5.8 μM in air equilibrated acetonitrile solutions. A pulsed laser operating at a 10 Hz frequency and with a 532 nm output of 10 mJ/pulse was employed to excite the sample.

Photoexcitation of solutions containing trace impurities of oxidized 7, or direct excitation of 7 where the three control layers were avoided (see FIG. 1), resulted in the generation of initially undetectable amounts ¹O₂ that were capable of reacting with the trap segment in 7. Chemical, rather than physical quenching of the trace amounts of ¹O₂ by 7 yielded, we postulate, compound 9-OOH (see FIG. 27), resulting in activation of otherwise dormant 7 and the amplification of ¹O₂ generation. Consistent with an autocatalytic activation mechanism, the $\varphi_A$ recorded following direct 532 nm laser excitation of an air equilibrated acetonitrile solution of 7 was observed to increase over time following a sigmoidal behavior (FIG. 28).[41-44] A ca. 6-fold increase in $\varphi_A$ was initially recorded. The ¹O₂ phosphorescence lifetime also followed a similar sigmoidal behavior with irradiation time, increasing from ca. 60 μs to 85 μs. Both the sigmoidal increase in phosphorescence lifetime and in $\varphi_A$ are consistent with depleting the trap segment in 7 thus reducing the amount of ¹O2 quencher while simultaneously yielding an active sensitizer, presumably compound 9-OOH.

Figure 29:
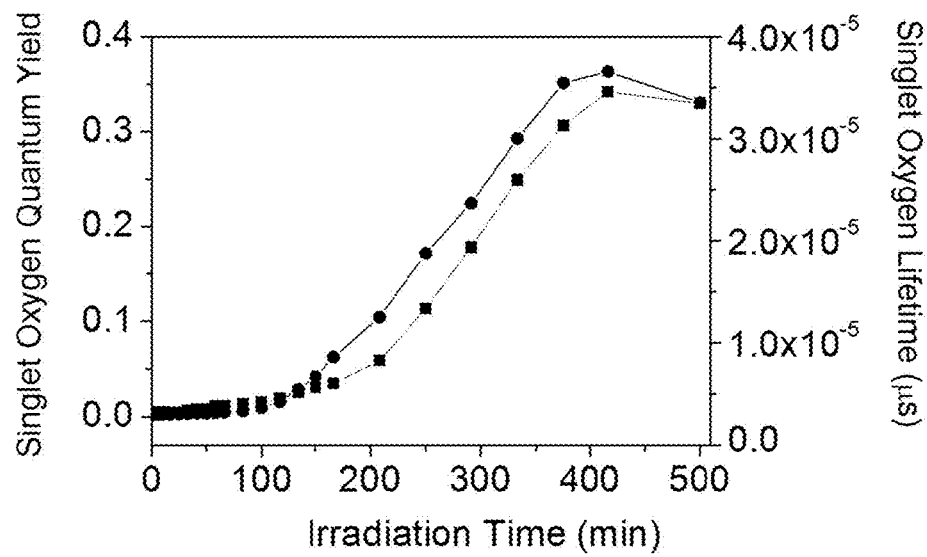
FIG. 29 shows the singlet oxygen quantum yield (■) and singlet oxygen lifetime (●) of compound 7 as a function of the irradiation time. [7]=5.8 μM in air equilibrated acetonitrile solution. [PMHC]=250 μM. Laser excitation was performed at 10 Hz and the energy of each pulse was 10 mJ.

Intrigued by the relatively small enhancement in $\varphi_A$ experimentally observed, we reasoned that some initial reaction may take place upon preparing solutions of 7. Direct activation upon reaction with cumyloxyl radicals yielded 40-fold enhancement (FIG. 25), however sacrificial amounts of PMHC (1 equivalent of PMHC per equivalent of 7) were added in that case to the solvent to prevent premature oxidation of 7. We next monitored $\varphi_A$ and ¹O₂ phosphorescence decay upon adding 250 μM PMHC to the solution prior to addition of compound 7 (FIG. 29, which shows the singlet oxygen quantum yield and singlet oxygen lifetime of compound 7 as a function of the irradiation time). In this case, the ¹O₂ phosphorescence lifetime was within the instrument response, i.e. ~3 μs. The $\varphi_A$ was further undetectable. Prolonged irradiation of this solution (8 hs, ~300,000 laser shots, 10 mJ/pulse) resulted in a ca. 25-fold increase in $\varphi_A$. Importantly, photodegradation of the BODIPY chromophore presumably prevented reaching the maximum possible enhancement in this case.

While monitoring the increase of ¹O₂ phosphorescence and/or lifetime gave a qualitative picture of the autocatalytic activation of 7, we reasoned that monitoring fluorescence increase real-time would provide a means to better analyze the autocatalytic process. Although 7 is sparingly emissive ($\varphi_f \leq 0.008$), the activated form would have similar emission to that of control 4, characterized by a $\varphi_f = 0.20$, thus enabling tracing the activation over time via the increase of fluorescence emission intensity. Continuous irradiation of an air equilibrated solution of 7 in acetonitrile within a fluorimeter exciting at 532 nm displayed a sigmoidal enhancement in emission (see FIG. 30 and FIG. 31, which shows the raw data for the normalized fluorescence intensity corresponding to the autocatalytic activation of compound 7 to generate 9-OOH as a function of irradiation time).[41-44]

The sigmoidal curve steepness depends strongly on the parameter k, the rate constant for autocatalysis, where a larger k determines a steeper curve. The value of the parameter k is determined by the combination of a series of rate constants and among others, it depends directly on the rate of photoexcitation and [O₂].[44]

Figure 30:
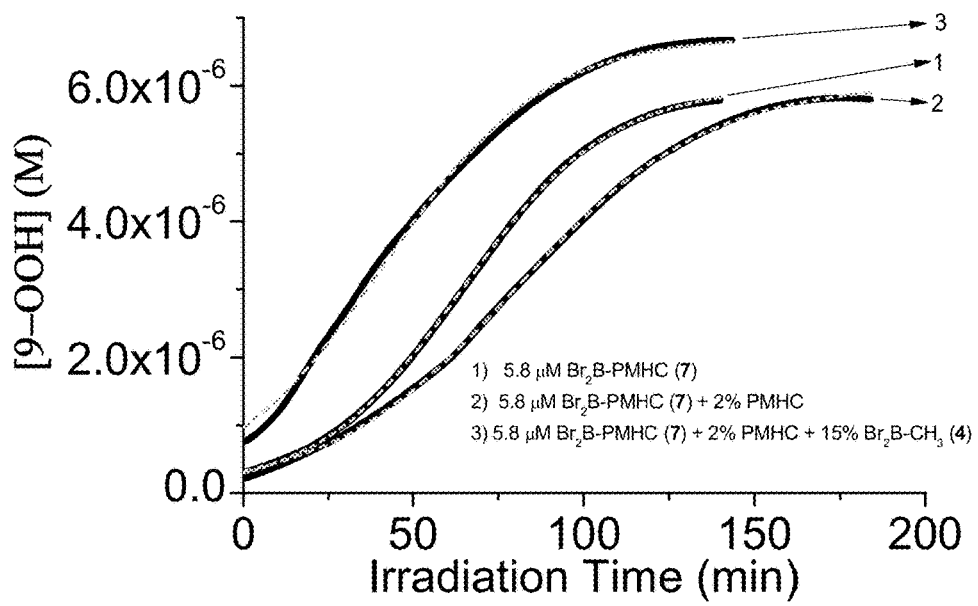
FIG. 30 shows the autocatalytic activation of compound 7 to generate 9-OOH as a function of irradiation time. Experiments were conducted in air equilibrated solutions in acetonitrile containing 5.8 μM of 7 (green trace), 5.8 μM of 7 and 0.12 μM of PMHC (2% equivalents of 7, blue trace), and 5.8 µM of 7, 0.12 µM of PMHC and 0.87 µM of 4 (15% equivalents of 7, black trace). In this latter case please note that the trajectory considers 4 as a surrogate of activated compound 9-OOH. Fitting of the data according to equation 9 are shown by the segment lines. The power of the incident light was 1.6 mW/cm².
Figure 31:
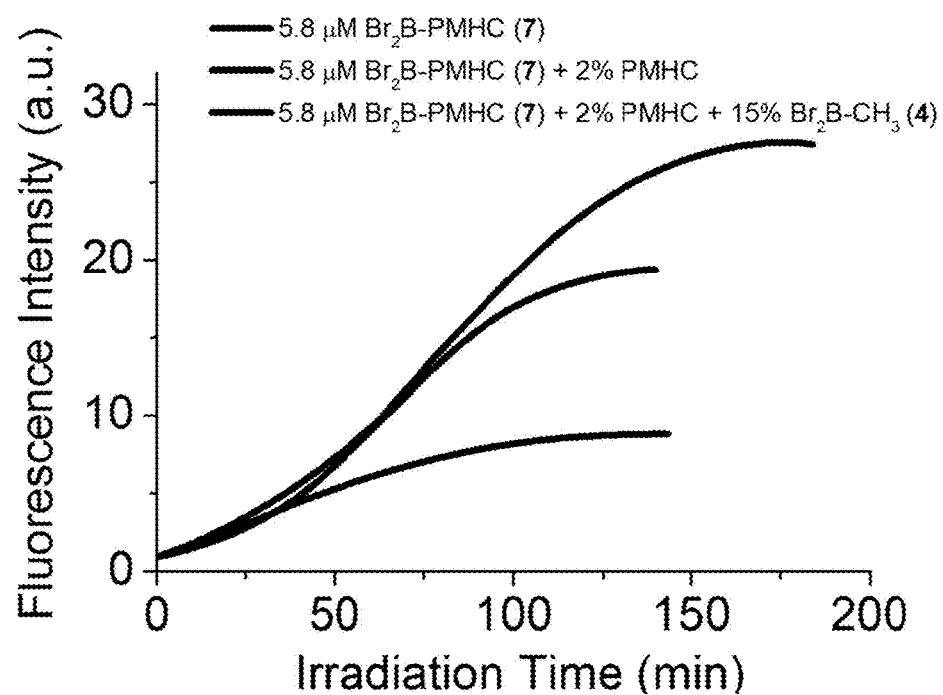
FIG. 31 shows the normalized fluorescence intensity corresponding to the autocatalytic activation of compound 7 to generate 9-OOH as a function of irradiation time. Experiments were conducted in air equilibrated solutions in acetonitrile containing 5.8 µM of 7 (middle trace), 5.8 µM of 7 and 0.12 µM of PMHC (2% equivalents of 7, top trace), and 5.8 µM of 7, 0.12 µM of PMHC and 0.87 µM of 4 (15% equivalents of 7, bottom trace). The power of the incident light was 1.6 mW/cm².

In order to avoid the pre-oxidation of 7, we next added 0.12 μM of sacrificial PMHC (2% equivalents of 7) to the solvent. Fluorescence intensity enhancements of ~30-fold were recorded in the latter case. This sample also displayed a longer induction period than that recorded when no PMHC was added. To emulate conditions of exacerbated pre-oxidation of 7, we next conducted experiments where 0.87 μM of 4 were added to the solution (15% equivalents of 7). Compound 4 was utilized to correctly account for the amount of activated singlet oxygen sensitizer, it is thus a surrogate of compound 9. In this case no induction period was observed (FIG. 30 and FIG. 31). The autocatalytic process (equation 7 below) under conditions of increasing amounts of activated compound follows the rate law given by equation 8, and the experimental results may be fitted according to equations 9 to 12.[41]

$$7 \xrightarrow{k} 9-\text{OOH} \quad \text{(Equation 7)}$$

Given the above reaction scheme the rate equation becomes $$-\frac{d[7]}{dt} = k \times [7] \times [9-\text{OOH}] = \frac{d[9-\text{OOH}]}{dt} \quad \text{(Equation 8)}$$

The solutions for [7] and [9-OOH] given the autocatalytic process are given by:

$$[9-\text{OOH}] = [9-\text{OOH}]_0 + \frac{b \times [7]_0 \times (e^{at} - 1)}{1 + b \times e^{at}} \quad \text{(Equation 9)}$$

$$[7] = [7]_0 - \frac{b \times [7]_0 \times (e^{at} - 1)}{1 + b \times e^{at}} \quad \text{(Equation 10)}$$

where a and b are given by $$a = ([7]_0 + [9-\text{OOH}]_0) \times k \quad \text{(Equation 11)}$$

and $$b = \frac{[9-\text{OOH}]_0}{[7]_0} \quad \text{(Equation 12)}$$

In equations 7 to 12, k is an apparent second order rate constant.[41] Doing a direct correlation between the fluorescence intensity and the initial concentration of 7 and assuming that all 7 is oxidized to yield 9-OOH, it was possible to obtain the concentration vs time profile for the photooxidation of 7 (see FIG. 30 and FIG. 31). The data was fit according to equation 9. The k values retrieved for the autocatalytic activation of 7 under different conditions were in the order of 8.0×10³ M⁻¹ min⁻¹. As previously described, less than 5% of 7 is pre-oxidized during the preparation of our sample. This value is consistent with the initial concentration of 9-OOH obtained from the fitting of the trajectory acquired with 7 only (no PMHC or compound 4).

Photodynamic Inactivation of Bacteria

Figure 32:
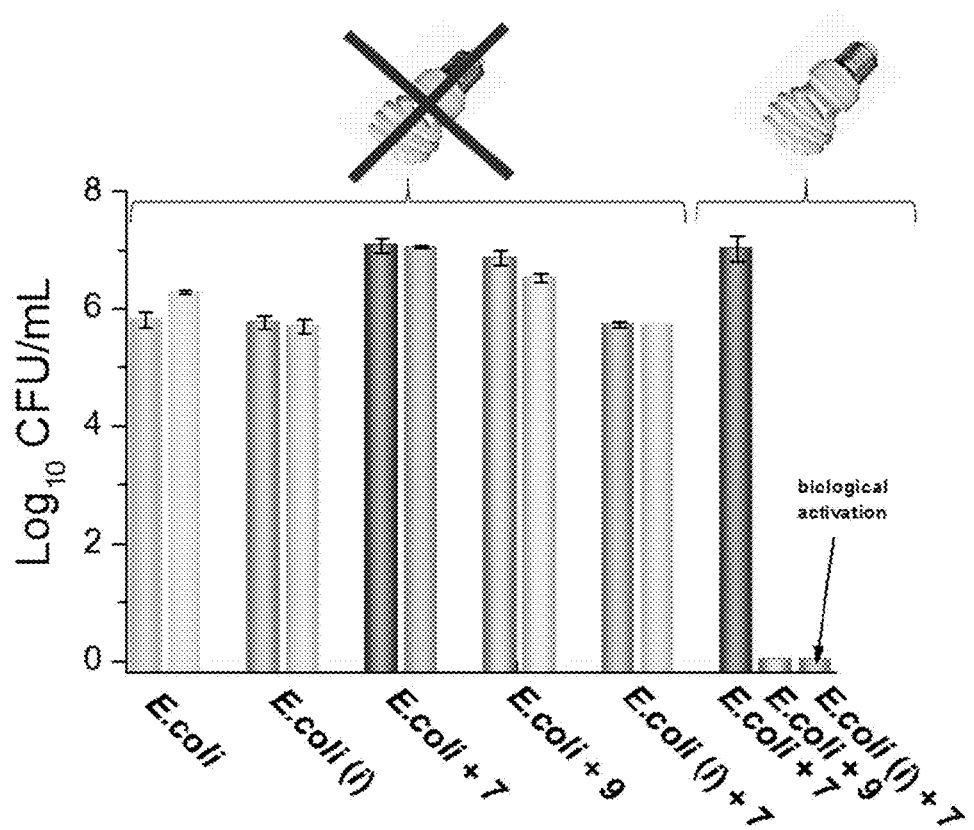
FIG. 32 shows the antibacterial photodynamic inactivation in *E. coli* ATCC 25922. *E. coli* dark controls (from left to right): control; incubated with 500 nM hydrogen peroxide (i); treated with 7; treated with 9; incubated with 500 nM hydrogen peroxide and treated with 7. *E. coli* after 1 hour irradiation (from left to right): *E. coli* treated with 7; *E. coli* treated with 9 (pre-activated 7) and *E. coli* incubated with 500 nM hydrogen peroxide and treated with 7. Light shades (i.e. columns on the right) represent the strain treated for 1 hour with compound 7 or 9 and darker shades (i.e. columns on the left) indicates no incubation period with compound 7 or 9.

We next validated the applicability of compound 7 towards the selective photodynamic inactivation of ROS-stressed vs regular bacteria. To stress the cells we utilized hydrogen peroxide, known to stimulate ROS production in Gram-negative cells.[79,80] We incubated bacteria from the *E. coli* strain ($10^6$ colony forming units (CFU)/mL) with 500 nM hydrogen peroxide for 2 hours at 37° C. Following precipitation and resuspension of this bacteria in media with no $H_2O_2$, we added compound 7. In parallel, compound 7 was also added to bacteria that were not exposed to $H_2O_2$. We next tested the bactericidal capability of compound 7 in both the ROS stressed (*E. coli* (i)+7) vs regular cells (incubated with no $H_2O_2$ (*E. coli*+7)) by counting *E. coli* colony forming units remaining after 1 h of continuous irradiation (2.6 mW/cm² with a maxima at 520 and a FWHM of 31 nm for 5 lamps 10 cm from the target) see FIG. 32.

A drastic drop in colony forming units was recorded following the combined action of compound 7 and irradiation for stressed cells. No inactivation was observed in turn for non-stressed healthy cells. A control experiment where cells were treated with preactivated 7 (compound 9) and light, but no $H_2O_2$ also showed a drastic drop in CFU. Additional control experiments in the dark for cells treated with compound 9 or with compound 7 (with or without $H_2O_2$), or simply with $H_2O_2$ showed no effect in the CFU, see FIG. 32.

CONCLUSION

The juxtaposed antioxidant and prooxidant antagonistic chemical activities of the newly developed dormant photosensitizer $Br_2B$-PMHC (7) enable the autocatalytic, and in general ROS-mediated, activation of $^1O_2$ sensitization providing a chemical cue for the spatiotemporal control of $^1O_2$ production. Kinetic and spectroscopic considerations show that the faster rate of ISC recorded for iodo vs bromo-substituted BODIPY segments, while desirable towards enhancing the yield of $^1O_2$ sensitization, provides a strain on the kinetic control of dormancy, i.e., a faster ISC rate necessitates faster rates of photoinduced electron transfer in order for the photosensitizer to be effectively dormant. This is exemplified by comparing compounds 7 and 8. Dormancy in the former results from a fast rate of PeT (methylene-linked chromanol) and a moderately large rate of ISC (bromo-bearing compound), whereas in the latter, characterized by a smaller rate of PeT (ester-linked chromanol, rather than methylene linked-chromanol) and a larger rate of ISC (iodo-bearing compound), dormancy is not achieved. From a spectroscopic viewpoint, the moderately large rate of ISC observed in bromo-substituted BODIPY dyes results in residual emission ($\varphi_f$~15%) being observed from these compounds, enabling real-time monitoring of the activation of the dormant photosensitizer bearing Br atoms, that will be of particular significance in cell studies. This does not come in major detriment of the quantum yield of $^1O_2$ for the Br-bearing BODIPY, at ca. 80%.

Compound 7 provides a new paradigm towards developing photosensitizers that will enable the controlled delivery of $^1O_2$ specifically in cells/tissues where metabolic imbalance leads to a large production of ROS, acting as a trigger/amplifier for $^1O_2$ photo-sensitization. The usefulness of this approach to selectively photoactivate the production of singlet oxygen in ROS stressed vs. regular cells was successfully tested via the photodynamic inactivation of ROS stressed Gram negative *E. coli* strain.

Example 2—Use of $Br_2B$-PMHC (Compound 7) in the Photodynamic Inactivation of Methicillin-Resistant *Staphylococcus aureus* (MRSA)

We tested the ability of $Br_2B$-PMHC to sensitize a strain of antibiotic resistant bacteria. The strain was a clinical biofilm-producing methicillin-resistant *Staphylococcus aureus* (MRSA). We measured bacterial concentration for the bacteria alone (control, "bact alone"), the bacteria treated with 1 microgram per milliliter of ciprofloxacin (control, "bact+cipro"), the bacteria treated with 10 micromolar of $Br_2B$-PMHC (control, "bact+10 Br"), and finally, the bacteria treated with 1 microgram per milliliter of ciprofloxacin and 5 or 10 micromolar of $Br_2B$-PMHC ("bact+Cipro+5 Br" and "bact+Cipro+10 Br", respectively), as a function of time (0 to 60 minutes) with and without exposure to light. Samples "without exposure to light" were kept wrapped with aluminum foil. Samples "with exposure to light" were irradiated with a LED panel having the following characteristics: 1.6 mW/cm² power output with a maxima (centered) at 520 nm and a full width at half maximum (FWHM) of 31 nm. The LED panel consisted of 5 lamps and was placed 10 cm from the sample.

Of note, the role of the ciprofloxacin in this test was not to kill the bacteria. Indeed, the chosen strain of bacteria is resistant to such antibiotic. Rather, the role of the ciprofloxacin was to stress the bacteria and thus lead to the production of reactive oxygen species (ROS). These ROS will, in turn, activate the dormant $Br_2B$-PMHC allowing it to become excited upon exposure to light and thus produce singlet oxygen ($^1O_2$) that will inactivate the bacteria.

Figure 33:
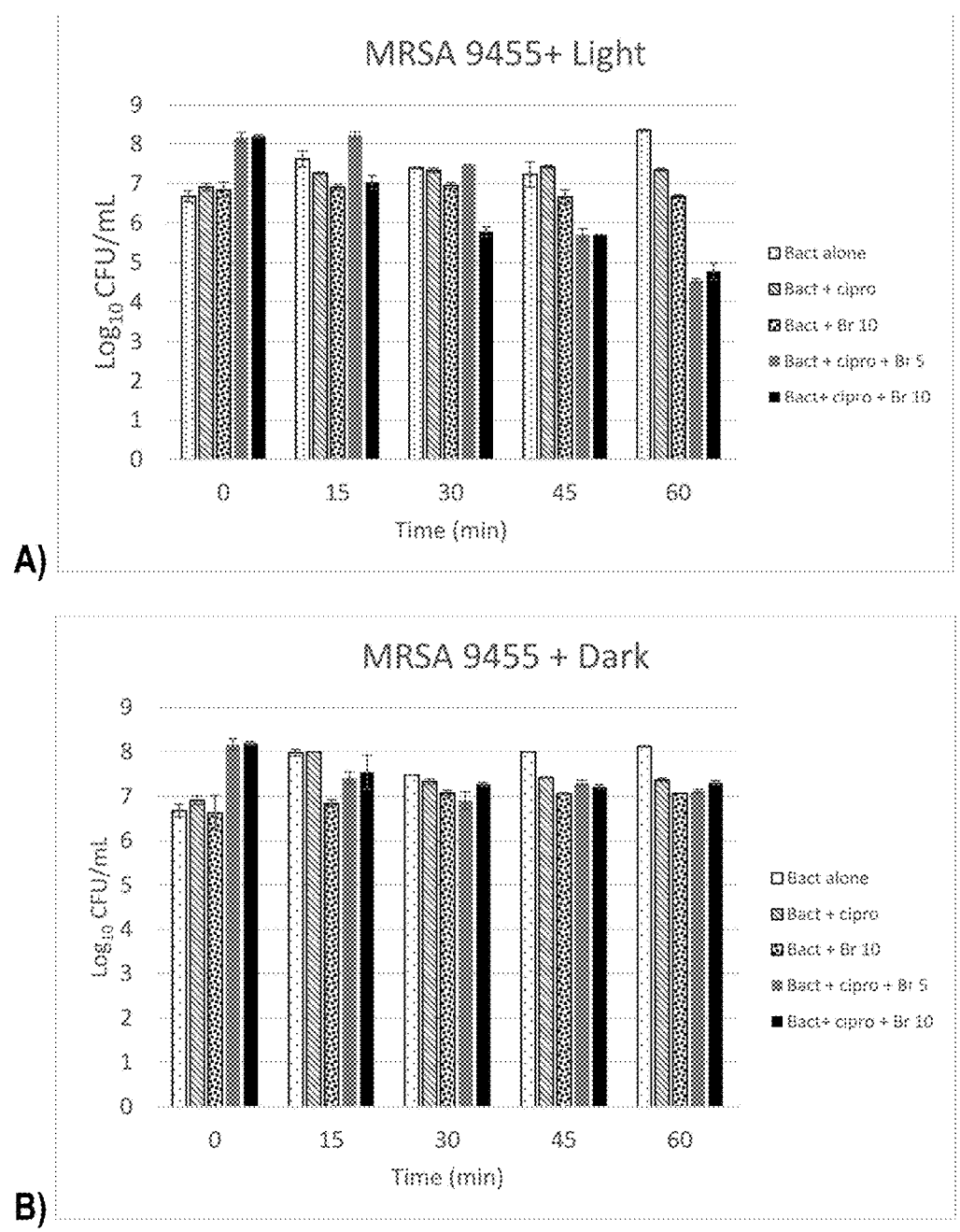
FIG. 33 shows the bacterial concentration A) for increasing light exposure times or B) as a function of time without light exposure.

FIG. 33 A) shows the bacterial concentration, expressed as log 10 CFU (colony forming units) per milliliter, for increasing light exposure times. For the bacteria, alone, those treated with ciprofloxacin only and those treated with $Br_2B$-PMHC only, there was no observed reduction in colony forming units upon prolonged illumination. In contrast, in the presence of both ciprofloxacin and $Br_2B$-PMHC, there was a clear reduction in colony forming units.

FIG. 33 B) shows the bacterial concentration, in the same conditions as FIG. 33A), as a function of time in the absence of light exposure. No reduction in colony forming units was observed for these samples.

These results reveal that $Br_2B$-PMHC is effective for the photodynamic inactivation of bacteria that have been made susceptible via the production of ROS in the presence of an antibiotic. Indeed, while the antibiotic alone failed to kill the bacteria (which was expected as the strain we used was resistant), it made them susceptible to photodynamic inactivation by $Br_2B$-PMHC because it prompted the production of ROS that activated the dormant $Br_2B$-PMHC. The photodynamic inactivation occurred only when the samples were exposed to light as otherwise the $Br_2B$-PMHC was not excited and did not produce the desired singlet oxygen ($^1O_2$).

The scope of the claims should not be limited by the preferred embodiments set forth in the examples, but should be given the broadest interpretation consistent with the description as a whole.

REFERENCES

The present description refers to a number of documents, the content of which is herein incorporated by reference in their entirety. These documents include, but are not limited to, the following:

(1) Dolmans, D. E.; Fukumura, D.; Jain, R. K. *Nat. Rev. Cancer* 2003, 3, 380.
(2) Ogilby, P. R. *Chem. Soc. Rev.* 2010, 39, 3181.
(3) Bonnett, R. Chemical aspects of photodynamic therapy; CRC Press, 2000.
(4) Lou, P. J.; Jones, L.; Hopper, C. *Technol. Cancer Res. Treat.* 2003, 2, 311.

(5) Bressler, N. M.; Bressler, S. B. *Invest. Ophthalmol. Vis. Sci.* 2000, 41, 624.
(6) Agostinis, P.; Berg, K.; Cengel, K. A.; Foster, T. H.; Girotti, A. W.; Gollnick, S. O.; Hahn, S. M.; Hamblin, M. R.; Juzeniene, A.; Kessel, D.; Korbelik, M.; Moan, J.; Mroz, P.; Nowis, D.; Piette, J.; Wilson, B. C.; Golab, J. *C. A. Cancer J. Clin.* 2011, 61, 250.
(7) Hamblin, M. R.; Hasan, T. *Photochem. Photobiol. Sci.* 2004, 3, 436.
(8) Turro, N. J.; Ramamurthy, V.; Scaiano, J. C. *Modern Molecular Photochemistry of Organic Molecules;* University Science Books, 2012.
(9) Schweitzer, C.; Schmidt, R. *Chem. Rev.* 2003, 103, 1685.
(10) Foote, C. S. *Acc. Chem. Res.* 1968, 1, 104.
(11) Zheng, G.; Chen, J.; Stefflova, K.; Jarvi, M.; Li, H.; Wilson, B. C. *Proc. Natl. Acad. Sci. U.S.A.* 2007, 104, 8989.
(12) Lovell, J. F.; Liu, T. W.; Chen, J.; Zheng, G. *Chem. Rev.* 2010, 110, 2839.
(13) Kamkaew, A.; Lim, S. H.; Lee, H. B.; Kiew, L. V.; Chung, L. Y.; Burgess, K. *Chem. Soc. Rev.* 2013, 42, 77.
(14) Huang, L.; Yang, W.; Zhao, J. *J. Org. Chem.* 2014, 79, 10240.
(15) Yogo, T.; Urano, Y.; Mizushima, A.; Sunahara, H.; Inoue, T.; Hirose, K.; Iino, M.; Kikuchi, K.; Nagano, T. *Proc. Natl. Acad. Sci. U.S.A.* 2008, 105, 28.
(16) Chen, J.; Stefflova, K.; Niedre, M. J.; Wilson, B. C.; Chance, B.; Glickson, J. D.; Zheng, G. *J. Am. Chem. Soc.* 2004, 126, 11450.
(17) Trachootham, D.; Zhou, Y.; Zhang, H.; Demizu, Y.; Chen, Z.; Pelicano, H.; Chiao, P. J.; Achanta, G.; Arlinghaus, R. B.; Liu, J.; Huang, P. *Cancer Cell* 2006, 10, 241.
(18) Szatrowski, T. P.; Nathan, C. F. *Cancer Res.* 1991, 51, 794.
(19) Schumacker, P. T. *Cancer Cell* 2006, 10, 175.
(20) Schumacker, P. T. *Cancer Cell* 2015, 27, 156.
(21) Gorrini, C.; Harris, I. S.; Mak, T. W. *Nat. Rev. Drug Discov.* 2013, 12, 931.
(22) Yogo, T.; Urano, Y.; Ishitsuka, Y.; Maniwa, F.; Nagano, T. *J. Am. Chem. Soc.* 2005, 127, 12162.
(23) Kasha, M. *J. Chem. Phys.* 1952, 20, 71.
(24) Niki, E.; Noguchi, N. *Acc. Chem. Res.* 2004, 37, 45.
(25) Burton, G. W.; Ingold, K. U. *Acc. Chem. Res.* 1986, 19, 194.
(26) Khatchadourian, A.; Krumova, K.; Boridy, S.; Ngo, A. T.; Maysinger, D.; Cosa, G. *Biochemistry* 2009, 48, 5658.
(27) Krumova, K.; Oleynik, P.; Karam, P.; Cosa, G. *J. Org. Chem.* 2009, 74, 3641.
(28) Oleynik, P.; Ishihara, Y.; Cosa, G. *J. Am. Chem. Soc.* 2007, 129, 1842.
(29) Krumova, K.; Friedland, S.; Cosa, G. *J. Am. Chem. Soc.* 2012, 134, 10102.
(30) Krumova, K.; Greene, L. E.; Cosa, G. *J. Am. Chem. Soc.* 2013, 135, 17135.
(31) Lincoln, R.; Greene, L. E.; Krumova, K.; Ding, Z.; Cosa, G. *J. Phys. Chem. A* 2014, 118, 10622.
(32) Fragata, M.; Bellemare, F. *Chem. Phys. Lipids* 1980, 27, 93.
(33) Fukuzawa, K.; Matsuura, K.; Tokumura, A.; Suzuki, A.; Terao, J. *Free Radic. Biol. Med.* 1997, 22, 923.
(34) Gorman, A. A.; Gould, I. R.; Hamblett, I.; Standen, M. C. *J. Am. Chem. Soc.* 1984, 106, 6956.
(35) Fukuzawa, K.; Inokami, Y.; Tokumura, A.; Terao, J.; Suzuki, A. *Lipids* 1998, 33, 751.
(36) Fahrenholtz, S. R.; Doleiden, F. H.; Trozzolo, A. M.; Lamola, A. A. *Photochem. Photobiol.* 1974, 20, 505.
(37) Foote, C. S.; Ching, T.-Y.; Geller, G. G. *Photochem. Photobiol.* 1974, 20, 511.
(38) Bryan, N.; Ahswin, H.; Smart, N.; Bayon, Y.; Wohlert, S.; Hunt, J. A. *Eur. Cell. Mater.* 2012, 24, 249.
(39) auf dem Keller, U.; Kumin, A.; Braun, S.; Werner, S. *J. Investig. Dermatol. Symp. Proc.* 2006, 11, 106.
(40) Niethammer, P.; Grabher, C.; Look, A. T.; Mitchison, T. J. *Nature* 2009, 459, 996.
(41) Montalban, A. G.; Meunier, H. G.; Ostler, R. B.; Barrett, A. G. M.; Hoffman, B. M.; Rumbles, G. *J. Phys. Chem. A* 1999, 103, 4352.
(42) Thapaliya, E. R.; Swaminathan, S.; Captain, B.; Raymo, F. M. *J. Am. Chem. Soc.* 2014, 136, 13798.
(43) Gustafson, T. P.; Metzel, G. A.; Kutateladze, A. G. *Photochem. Photobiol. Sci.* 2012, 11, 564.
(44) Bartusik, D.; Minnis, M.; Ghosh, G.; Greer, A. *J. Org. Chem.* 2013, 78, 8537.
(45) Godin, R.; Liu, H. W.; Smith, L.; Cosa, G. *Langmuir* 2014, 30, 11138.
(46) Johnson, I. D.; Kang, H. C.; Haugland, R. P. *Anal. Biochem.* 1991, 198, 228.
(47) Bonnett, R. *Chem. Soc. Rev.* 1995, 24, 19.
(48) Horrobin, D. F. *New Approaches to Cancer Treatment: Unsaturated Lipids and Photodynamic Therapy;* Churchill Communications Europe, 1994.
(49) Rapozzi, V.; Miculan, M.; Xodo, L. E. *Cancer Biol. Ther.* 2009, 8, 1318.
(50) Loudet, A.; Burgess, K. *Chem. Rev.* 2007, 107, 4891.
(51) Wood, T. E.; Thompson, A. *Chem. Rev.* 2007, 107, 1831.
(52) Ulrich, G.; Ziessel, R.; Harriman, A. *Angew. Chem. Int. Ed. Engl.* 2008, 47, 1184.
(53) López Arbeloa, F.; Banuelos, J.; Martinez, V.; Arbeloa, T.; López Arbeloa, I. *Int. Rev. Phys. Chem.* 2005, 24, 339.
(54) Krumova, K.; Cosa, G. *J. Am. Chem. Soc.* 2010, 132, 17560.
(55) Jiao, L.; Pang, W.; Zhou, J.; Wei, Y.; Mu, X.; Bai, G.; Hao, E. *J. Org. Chem.* 2011, 76, 9988.
(56) Krumova, K.; Cosa, G. *Photochemistry:* Volume 41 2013, 41, 279.
(57) Yin, H.; Xu, L.; Porter, N. A. *Chem. Rev.* 2011, 111, 5944.
(58) Girotti, A. W. *J. Lipid Res.* 1998, 39, 1529.
(59) Shahidi, F.; Zhong, Y. *Chem. Soc. Rev.* 2010, 39, 4067.
(60) Porter, N. A. *Acc. Chem. Res.* 1986, 19, 262.
(61) Lu, Z. T.; Zhang, X. G.; Wu, Z. M.; Zhai, T. T.; Xue, Y. A.; Mei, L.; Li, C. X. *RSC Adv.* 2014, 4, 19495.
(62) Ma, J.; Yuan, X. L.; Kucukoz, B.; Li, S. F.; Zhang, C. S.; Majumdar, P.; Karatay, A.; Li, X. H.; Yaglioglu, H. G.; Elmali, A.; Zhao, J. Z.; Hayvali, M. *J. Mater. Chem. C* 2014, 2, 3900.
(63) Guo, S.; Ma, L. H.; Zhao, J. Z.; Kucukoz, B.; Karatay, A.; Hayvali, M.; Yaglioglu, H. G.; Elmali, A. *Chem. Sci.* 2014, 5, 489.
(64) Lai, Y. C.; Chang, C. C. *J. Mater. Chem. C* 2014, 2, 1576.
(65) Adarsh, N.; Avirah, R. R.; Ramaiah, D. *Org. Lett* 2010, 12, 5720.
(66) López Arbeloa, F.; Banuelos, J.; Martinez, V.; Arbeloa, T.; López Arbeloa, I. *Int. Rev. Phys. Chem.* 2005, 24, 339.
(67) Cosa, G.; Scaiano, J. C. *Photochem. Photobiol.* 2004, 80, 159.
(68) Galletta, M.; Campagna, S.; Quesada, M.; Ulrich, G.; Ziessel, R. *Chem. Commun. (Camb.)* 2005, 4222.
(69) Wu, W.; Guo, H.; Wu, W.; Ji, S.; Zhao, J. *J. Org. Chem.* 2011, 76, 7056.

(70) Zhang, X. F.; Yang, X. *J. Phys. Chem. B* 2013, 117, 5533.
(71) Rehm, D.; Weller, A. *Isr. J. Chem.* 1970, 8, 259.
(72) Franco, C.; Olmsted Iii, J. *Talanta* 1990, 37, 905.
(73) Wilkinson, F.; Helman, W. P.; Ross, A. B. *J. Phys. Chem. Ref. Data* 1993, 22, 113.
(74) Mukai, K.; Daifuku, K.; Okabe, K.; Tanigaki, T.; Inoue, K. *J. Org. Chem.* 1991, 56, 4188.
(76) Gomes, A.; Fernandes, E.; Lima, J. L. J. *Biochem. Biophys. Methods* 2005, 65, 45.
(79) Dwyer, D. J.; Belenky, P. A.; Yang, J. H.; MacDonald, I. C.; Martell, J. D.; Takahashi, N.; Chan, C. T. Y.; Lobritz, M. A.; Braff, D.; Schwarz, E. G.; Ye, J. D.; Pati, M.; Vercruysse, M.; Ralifo, P. S.; Allison, K. R.; Khalil, A. S.; Ting, A. Y.; Walker, G. C.; Collins, J. J. *Proc. Natl. Acad. Sci. U.S.A* 2014, 111, E2100.
(80) Imlay, J. A.; Chin, S. M.; Linn, S. *Science* 1988, 240, 640.
(81) Wilkinson, F.; Helman, W. P.; Ross, A. B. *J. Phys. Chem. Ref. Data* 1993, 22, 113.
(82) Nepomnyashchii, A. B.; Broring, M.; Ahrens, J.; Bard, A. J. *J. Am. Chem. Soc.* 2011, 133, 8633.
(83) Nepomnyashchii, A. B.; Bard, A. J. *Acc. Chem. Res.* 2012, 45, 1844.
(84) Krumova, K.; Cosa, G. *J. Am. Chem. Soc.* 2010, 132, 17560.
(85) Krumova, K.; Friedland, S.; Cosa, G. *J. Am. Chem. Soc.* 2012, 134, 10102.

The invention claimed is:

1. A compound of formula (I):

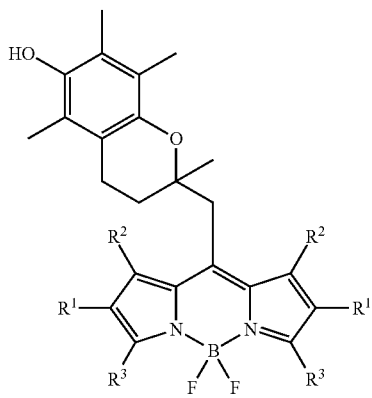

(I)

wherein:
$R^1$ are the same and represent —Br or —I,
$R^2$ are the same or different and represent —H or an alkyl group, and
$R^3$ are the same or different and represent an alkyl group or a haloalkyl group.

2. The compound of claim 1, wherein both $R^1$ groups are —Br.

3. The compound of claim 1, wherein both $R^1$ groups are —I.

4. The compound of claim 1, wherein both $R^2$ groups are the same.

5. The compound of claim 2, wherein both $R^2$ group are methyl.

6. The compound of claim 3, wherein both $R^2$ group are methyl.

7. The compound of claim 4, wherein both $R^2$ group are methyl.

8. The compound of claim 4, wherein both $R^2$ groups are —H.

9. The compound of claim 1, wherein the $R^2$ groups are different from one another.

10. The compound of claim 1, wherein both $R^3$ groups are the same.

11. The compound of claim 7, wherein both $R^3$ group are methyl.

12. The compound of claim 10, wherein both $R^3$ group are methyl.

13. The compound of claim 1, wherein the $R^3$ groups are different from one another.

14. The compound of claim 1 being

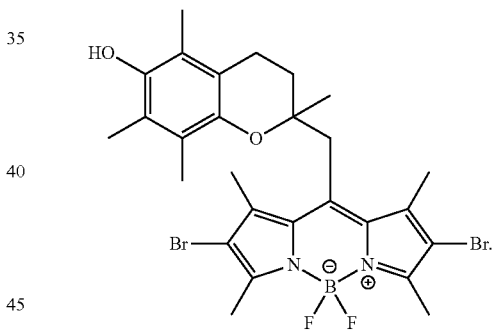

* * * * *